(12) United States Patent
He et al.

(10) Patent No.: US 8,722,691 B2
(45) Date of Patent: May 13, 2014

(54) AZOLOPYRIMIDINES AS INHIBITORS OF CANNABINOID 1 ACTIVITY

(75) Inventors: Xiaohui He, San Diego, CA (US); Kunyong Yang, San Diego, CA (US); Hong Liu, San Diego, CA (US); David Archer Ellis, San Diego, CA (US)

(73) Assignee: IRM LLC, Hamilton (BM)

( * ) Notice: Subject to any disclaimer, the term of this patent is extended or adjusted under 35 U.S.C. 154(b) by 496 days.

(21) Appl. No.: 12/295,555

(22) PCT Filed: Mar. 30, 2007

(86) PCT No.: PCT/US2007/007989
§ 371 (c)(1),
(2), (4) Date: Apr. 6, 2009

(87) PCT Pub. No.: WO2007/120454
PCT Pub. Date: Oct. 25, 2007

(65) Prior Publication Data
US 2009/0247556 A1  Oct. 1, 2009

Related U.S. Application Data

(60) Provisional application No. 60/788,310, filed on Mar. 30, 2006.

(51) Int. Cl.
*C07D 487/04* (2006.01)
*A61K 31/519* (2006.01)
*A61P 3/04* (2006.01)

(52) U.S. Cl.
USPC ........................................ 514/262.1; 544/262

(58) Field of Classification Search
USPC ........................................ 544/262; 514/262.1
See application file for complete search history.

(56) References Cited

U.S. PATENT DOCUMENTS

2009/0247517 A1* 10/2009 Liu et al. .................... 514/234.2

FOREIGN PATENT DOCUMENTS

| RU | 2216542 | 11/2003 |
|---|---|---|
| WO | WO 2004094417 | 11/2004 |
| WO | WO 2004094429 | 11/2004 |
| WO | WO 2005/049615 A1 | 6/2005 |
| WO | WO 2005061505 | 7/2005 |
| WO | WO 2005061509 | 7/2005 |
| WO | WO 2006/047516 A2 | 5/2006 |

* cited by examiner

Primary Examiner — Susanna Moore

(74) Attorney, Agent, or Firm — Chihang Amy Smith; Genomics Institute of the Novartis Research Foundation

(57) ABSTRACT

The invention provides compounds, pharmaceutical compositions comprising such compounds, and methods of using such compounds to treat or prevent diseases or disorders associated with the activity of Cannabinoid Receptor 1 (CB1). The compounds are of the Formulae Ia, Ic, Ig and Ik:

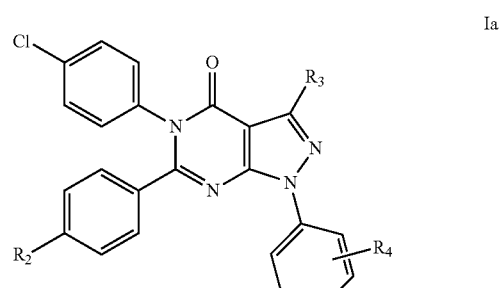

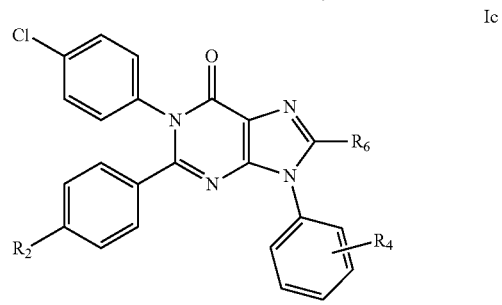

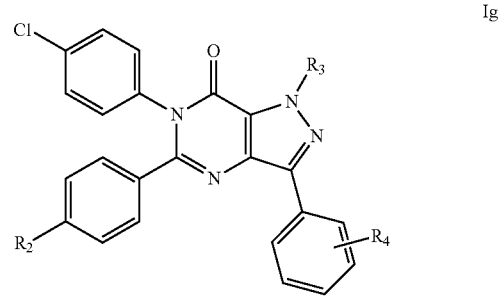

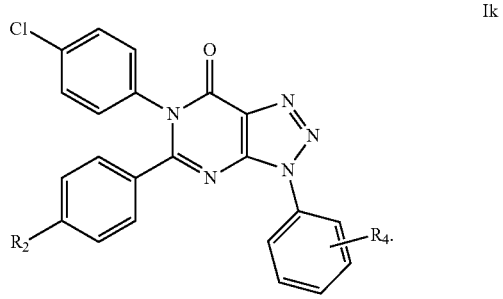

9 Claims, No Drawings

AZOLOPYRIMIDINES AS INHIBITORS OF CANNABINOID 1 ACTIVITY

CROSS-REFERENCE TO RELATED APPLICATIONS

This application is a 371 U.S. national phase application of international application number PCT/US2007/007989 filed 30 Sep. 2007, which application claims priority to U.S. provisional patent application No. 60/788,310, filed 30 Mar. 2006. The full disclosure of these applications is incorporated herein by reference in its entirety and for all purposes.

BACKGROUND OF THE INVENTION

1. Field of the Invention

The invention provides compounds, pharmaceutical compositions comprising such compounds and methods of using such compounds to treat or prevent diseases or disorders associated with the activity of Cannabinoid Receptor 1 (CB1).

2. Background

The cannabinoids are psychoactive ingredients of marijuana, principally delta-9-tetrahydrocannabinol. Two cannabinoid receptors have been cloned, CB1 and CB2. CB1 is predominantly expressed in the central nervous system whereas CB2 is expressed in peripheral tissues, principally in the immune system. Both receptors are members of the G-protein coupled class and their inhibition is linked to adenylate cyclase activity.

The novel compounds of this invention inhibit the activity of CB1 and are, therefore, expected to be useful in the treatment of CB1-associated diseases or disorders such as, but not limited to, psychosis, memory deficit, cognitive disorders, migraine, neuropathy, neuroinflammatory disorders, cerebral vascular accidents, head trauma, anxiety disorders, substance abuse (such as smoking cessation), stress, epilepsy, Parkinson's disease, schizophrenia, osteoporosis, constipation, chronic intestinal pseudo-obstruction, cirrhosis of the liver, asthma, obesity, and other eating disorders associated with excessive food intake.

SUMMARY OF THE INVENTION

In one aspect, the present invention provides compound selected from Formula Ia, Ic, Ig and Ik:

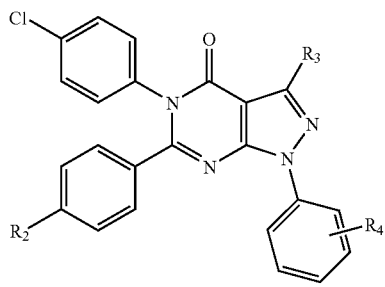

Ia

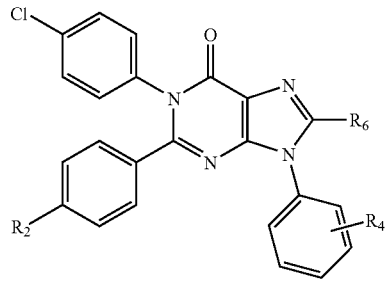

Ic

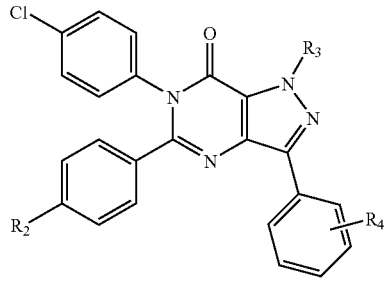

Ig

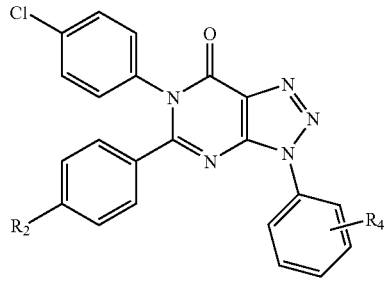

Ik in which:

$R_2$ is selected from halo, pyrazinyl, pyridazinyl, pyrimidinyl, pyridinyl, pyridinyl-N-oxide and phenyl; wherein said pyrimidinyl, pyridinyl, pyridinyl-N-oxide, pyrazinyl and phenyl of $R_2$ is optionally substituted with a radical selected from amino, halo, amino-sulfonyl and phenyl;

$R_3$ is selected from hydrogen, methyl-sulfonyl, methyl-sulfoxide and dimethyl-amino-carbonyl;

$R_4$ is selected hydrogen, cyano, nitro, carbamimidoyl, tetrazolyl, amino-sulfonyl, amino-carbonyl, methyl-sulfonyl-amino, and methyl-sulfonyl;

$R_6$ is selected from hydrogen, hydroxy-ethyl-amino-methyl and methyl-sulfonyl-aminomethyl; and the pharmaceutically acceptable salts, hydrates, solvates and isomers thereof.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of CB1 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which CB1 activity contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-6}$alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl can be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, 1H-pyridin-2-onyl, 6-oxo-1,6-dihydro-pyridin-3-yl, etc. "$C_{6-10}$aryl$C_{0-4}$alkyl" means an aryl as described above connected via a alkylene grouping. For example, $C_{6-10}$aryl$C_{0-4}$alkyl includes phenethyl, benzyl, etc. Heteroaryl also includes the N-oxide derivatives, for example, pyridine-N-oxide derivatives with the following structure:

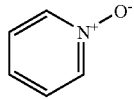

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 1,4-dioxa-8-aza-spiro[4.5]dec-8-yl, 2-oxo-pyrrolidin-1-yl, 2-oxo-piperidin-1-yl, etc.

"Halogen" (or halo) preferably represents chloro or fluoro, but can also be bromo or iodo.

"Treat", "treating" and "treatment" refer to a method of alleviating or abating a disease and/or its attendant symptoms.

Description of the Preferred Embodiments

The present invention provides compounds, compositions and methods for the treatment of diseases in which inhibition of CB1 activity can prevent, inhibit or ameliorate the pathology and/or symptomology of the diseases, which method comprises administering to the animal a therapeutically effective amount of a compound of Formula I.

In one embodiment, compounds of the invention are selected from: 5-[4-(2-amino-pyrimidin-4-yl)-phenyl]-6-(4-chloro-phenyl)-3-phenyl-3,6-dihydro-[1,2,3]triazolo[4,5-d]pyrimidin-7-one; 6-[4-(6-amino-pyridin-3-yl)-phenyl]-5-(4-chloro-phenyl)-3-methanesulfonyl-1-phenyl-1,5-dihydro-pyrazolo[3,4-d]pyrimidin-4-one; 6-[4-(6-amino-1-oxy-pyridin-3-yl)-phenyl]-5-(4-chloro-phenyl)-1-phenyl-1,5-dihydro-pyrazolo[3,4-d]pyrimidin-4-one; 2-(biphenyl-4-yl)-1-(4-chlorophenyl)-8-((2-hydroxyethylamino)methyl)-9-phenyl-1H-purin-6(9H)-one; 3-(6-(4-bromophenyl)-5-(4-chlorophenyl)-4-oxo-4,5-dihydro-1H-pyrazolo[3,4-d]pyrimidin-1-yl)benzenesulfonamide; 3-(6-(4-bromophenyl)-5-(4-chlorophenyl)-4-oxo-4,5-dihydro-1H-pyrazolo[3,4-d]pyrimidin-1-yl)benzenesulfonamide; 5-[4-(6-amino-pyridin-3-yl)-phenyl]-6-(4-chloro-phenyl)-7-oxo-3-phenyl-6,7-dihydro-pyrazolo[4,3-d]pyrimidine-1-carboxylic acid dimethylamide; 6-[4-(6-amino-pyridazin-3-yl)-phenyl]-5-(4-chloro-phenyl)-1-(3-methanesulfonyl-phenyl)-1,5-dihydro-pyrazolo[3,4-d]pyrimidin-4-one; N-[2-[4-(6-amino-pyridin-3-yl)-phenyl]-1-(4-chloro-phenyl)-6-oxo-9-phenyl-6,9-dihydro-1H-purin-8-ylmethyl]-methanesulfonamide; 6-[4-(6-amino-pyridin-3-yl)-phenyl]-5-(4-chloro-phenyl)-3-methanesulfinyl-1-phenyl-1,5-dihydro-pyrazolo[3,4-d]pyrimidin-4-one; 6-(4-(2-aminopyridin-4-yl)phenyl)-5-(4-chlorophenyl)-3-(methylsulfonyl)-1-phenyl-1H-pyrazolo[3,4-d]pyrimidin-4(5H)-one; 3-[6-(4-bromo-phenyl)-5-(chloro-phenyl)-4-oxo-4,5-dihydro-pyrazolo[3,4-d]pyrimidin-1-yl]-benzamide; 3-[6-[4-(6-amino-pyridin-3-yl)-phenyl]-5-(4-chloro-phenyl)-4-oxo-4,5-dihydro-pyrazolo[3,4-d]pyrimidin-1-yl]-benzamide; 6-[4-(6-amino-pyridin-3-yl)-phenyl]-5-(4-chloro-phenyl)-1-(3-methanesulfonyl-phenyl)-1,5-dihydro-pyrazolo[3,4-d]pyrimidin-4-one; 6-(4-Chloro-phenyl)-3-(3-methanesulfonyl-phenyl)-5-(4-pyrazin-2-yl-phenyl)-3,6-dihydro-[1,2,3]triazolo[4,5-d]pyrimidin-7-one; 5-[4-(6-amino-pyridin-3-yl)-phenyl]-6-(4-chloro-phenyl)-3-(3-methanesulfonyl-phenyl)-3,6-dihydro-[1,2,3]triazolo[4,5-d]pyrimidin-7-one; 6-[4-(5-amino-pyridin-2-yl)-phenyl]-5-(4-chloro-phenyl)-3-methanesulfonyl-1-phenyl-1,5-dihydro-pyrazolo[3,4-d]pyrimidin-4-one; 6-[4-(5-amino-pyrazin-2-yl)-phenyl]-5-(4-chloro-phenyl)-3-methanesulfonyl-1-phenyl-1,5-dihydro-pyrazolo[3,4-d]pyrimidin-4-one; 6-[4-(5-amino-pyridin-2-yl)-phenyl]-5-(4-chloro-phenyl)-1-(3-methanesulfonyl-phenyl)-1,5-dihydro-pyrazolo[3,4-d]pyrimidin-4-one; 6-[4-(5-amino-pyrazin-2-yl)-phenyl]-5-(4-chloro-phenyl)-1-(3-methanesulfonyl-phenyl)-1,5-dihydro-pyrazolo[3,4-d]pyrimidin-4-one; 6-[4-(2-amino-pyrimidin-5-yl)-phenyl]-5-(4-chloro-phenyl)-3-methanesulfonyl-1-phenyl-1,5-dihydro-pyrazolo[3,4-d]pyrimidin-4-one; 6-[4-(2-amino-pyrimidin-5-yl)-phenyl]-5-(4-chloro-phenyl)-1-(3-methanesulfonyl-phenyl)-1,5-dihydro-pyrazolo[3,4-d]pyrimidin-4-one; 3-[5-(4-chloro-phenyl)-4-oxo-6-(4-pyrazin-2-yl-phenyl)-4,5-dihydro-pyrazolo[3,4-d]pyrimidin-1-yl]-benzamide; N-{3-[2-[4-(6-amino-pyridin-3-yl)-phenyl]-1-(4-chloro-phenyl)-6-oxo-1,6-dihydro-purin-9-yl]-phenyl}-methane sulfonamide; 3-[2-[4-(6-amino-pyridin-3-yl)-phenyl]-1-(4-chloro-phenyl)-6-oxo-1,6-dihydro-purin-9-yl]-benzene sulfonamide; N-{3-[2-[4-(5-amino-pyridin-2-yl)-phenyl]-1-(4-chloro-phenyl)-6-oxo-1,6-dihydro-purin-9-yl]-phenyl}-methane sulfonamide; 3-(6-(4-(5-aminopyridin-2-yl)phenyl)-5-(4-chlorophenyl)-4-oxo-4,5-dihydro-1H-pyrazolo[3,4-d]pyrimidin-1-yl) benzonitrile; 3-(6-(4-(6-aminopyridin-3-yl)phenyl)-5-(4-chlorophenyl)-4-oxo-4,5-dihydro-1H-pyrazolo[3,4-d]pyrimidin-1-yl)benzonitrile; 3-[6-[4-(6-amino-pyridin-3-yl)-phenyl]-5-(4-chloro-phenyl)-4-oxo-4,5-dihydro-pyrazolo[3,4-d]pyrimidin-1-yl]-benzamidine; 3-[6-[4-(5- amino-pyridin-2-yl)-phenyl]-5-(4-chloro-phenyl)-4-oxo-4,5-dihydro-pyrazolo[3,4-d]pyrimidin-1-yl]-benzamidine; 3-(2-(4-bromophenyl)-1-(4-chlorophenyl)-6-oxo-1H-purin-9(6H)-yl)benzenesulfonamide; 6-[4-(6-amino-pyridin-3-yl)-phenyl]-5-(4-chloro-phenyl)-1-[3-(1H-tetrazol-5-yl)-phenyl]-1,5-dihydro-pyrazolo[3,4-d]pyrimidin-4-one; 6-[4-(5-amino-pyridin-2-yl)-phenyl]-5-(4-chloro-phenyl)-1-[3-(1H-tetrazol-5-yl)-phenyl]-1,5-dihydro-pyrazolo[3,4-d]pyrimidin-4-one; 2-(4-bromophenyl)-1-(4-chlorophenyl)-9-(3-(methylsulfonyl)phenyl)-1H-purin-6(9H)-one; N-(3-(6-(4-(6-aminopyridin-3-yl)phenyl)-5-(4-chlorophenyl)-4-oxo-4,5-dihydro-1H-pyrazolo[3,4-d]pyrimidin-1-yl)phenyl)methanesulfonamide; 2-[4-(6-amino-pyridin-3-yl)-phenyl]-1-(4-chloro-phenyl)-9-(3-methanesulfonyl-phenyl)-1,9-dihydro-purin-6-one; N-(3-(6-(4-(5-aminopyridin-2-yl)phenyl)-5-(4-chlorophenyl)-4-oxo-4,5-dihydro-1H-pyrazolo[3,4-d]pyrimidin-1-yl)phenyl)methanesulfonamide; 2-[4-(5-amino-pyridin-2-yl)-phenyl]-1-(4-chloro-phenyl)-9-(3-methanesulfonyl-phenyl)-1,9-dihydro-purin-6-one; 6-(4-bromo-phenyl)-5-(4-chloro-phenyl)-1-(3-nitro-phenyl)-1,5-dihydro-pyrazolo[3,4-d]pyrimidin-4-one; 3-(6-(4-bromophenyl)-5-(4-chlorophenyl)-4-oxo-4,5-dihydro-1H-pyrazolo[3,4-d]pyrimidin-1-yl)benzonitrile; 3-[2-[4-(5-amino-pyridin-2-yl)-phenyl]-1-(4-chloro-phenyl)-6-oxo-1,6-dihydro-purin-9-yl]-benzamidine; 3-[2-[4-(5-amino-pyridin-2-yl)-phenyl]-1-(4-chloro-phenyl)-6-oxo-1,6-dihydro-purin-9-yl]-benzene sulfonamide; 3-[2-[4-(5-amino-pyridin-2-yl)-phenyl]-1-(4-chloro-phenyl)-6-oxo-1,6-dihydro-purin-9-yl]-benzonitrile; 3-[2-[4-(6-amino-pyridin-3-yl)-phenyl]-1-(4-chloro-phenyl)-6-oxo-1,6-dihydro-purin-9-yl]-benzonitrile; N-{3-[1-(4-chloro-phenyl)-6-oxo-2-(4-pyrimidin-2-yl-phenyl)-1,6-dihydro-purin-9-yl]-phenyl}-methane sulfonamide; 1-(4-chloro-phenyl)-9-(3-methanesulfonyl-phenyl)-2-(4-pyrazin-2-yl-phenyl)-1,9-dihydro-purin-6-one; 3-[5-(4-chloro-phenyl)-4-oxo-6-(4-pyrazin-2-yl-phenyl)-4,5-dihydro-pyrazolo[3,4-d]pyrimidin-1-yl]-benzonitrile; 3-[2-[4-(6-amino-pyridin-3-yl)-phenyl]-1-(4-chloro-phenyl)-6-oxo-1,6-dihydro-purin-9-yl]-benzamidine; N-(3-(5-(4-chlorophenyl)-4-oxo-6-(4-(pyrimidin-2-yl)phenyl)-4,5-dihydro-1H-pyrazolo[3,4-d]pyrimidin-1-yl)phenyl)methanesulfonamide; N-{3-[5-(4-chloro-phenyl)-4-oxo-6-(4-pyrimidin-5-yl-phenyl)-4,5-dihydro-pyrazolo[3,4-d]pyrimidin-1-yl]-phenyl}-methane sulfonamide; 5-(4-chlorophenyl)-1-(3-(methylsulfonyl)phenyl)-6-(4-(pyrazin-2-yl)phenyl)-1H-pyrazolo[3,4-d]pyrimidin-4(5H)-one; 3-[5-(4-chloro-phenyl)-4-oxo-6-(4-pyrazin-2-yl-phenyl)-4,5-dihydro-pyrazolo[3,4-d]pyrimidin-1-yl]-benzamidine; N-(3-(5-(4-chlorophenyl)-4-oxo-6-(4-(pyridazin-3-yl)phenyl)-4,5-dihydro-1H-pyrazolo[3,4-d]pyrimidin-1-yl)phenyl)methanesulfonamide; N-{3-[1-(4-chloro-phenyl)-6-oxo-2-(4-pyrimidin-5-yl-phenyl)-1,6-dihydro-purin-9-yl]-phenyl}-methane sulfonamide; N-(3-(5-(4-chlorophenyl)-4-oxo-6-(4-(pyrazin-2-yl)phenyl)-4,5-dihydro-1H-pyrazolo[3,4-d]pyrimidin-1-yl)phenyl)methanesulfonamide; N-{3-[1-(4-chloro-phenyl)-6-oxo-2-(4-pyridazin-3-yl-phenyl)-1,6-dihydro-purin-9-yl]-phenyl}-methane sulfonamide; 3-(5-(4-chlorophenyl)-4-oxo-6-(4-(pyrazin-2-yl)phenyl)-4,5-dihydro-1H-pyrazolo[3,4-d]pyrimidin-1-yl)benzenesulfonamide; N-{3-[1-(4-chloro-phenyl)-6-oxo-2-(4-pyrazin-2-yl-phenyl)-1,6-dihydro-purin-9-yl]-phenyl}-methane sulfonamide; 3-[1-(4-chloro-phenyl)-6-oxo-2-(4-pyrazin-2-yl-phenyl)-1,6-dihydro-purin-9-yl]-benzene sulfonamide; 5-(4-chloro-phenyl)-1-(3-methanesulfonyl-phenyl)-6-(4-pyrimidin-5-yl-phenyl)-1,5-dihydro-pyrazolo[3,4-d]pyrimidin-4-one; 5-(4-chloro-phenyl)-1-(3-methanesulfonyl-phenyl)-6-(4-pyrimidin-2-yl-phenyl)-1,5-dihydro-pyrazolo[3,4-d]pyrimidin-4-one; and 3-[6-[4-(5-amino-pyridin-2-yl)-phenyl]-5-(4-chloro-phenyl)-4-oxo-4,5-dihydro-pyrazolo[3,4-d]pyrimidin-1-yl]-benzene sulfonamide.

Another embodiment provides for a method of treating a disease mediated by the Cannabinoid-1 receptor (for example, an eating disorder associated with excessive food intake like obesity, bulimia nervosa, and compulsive eating disorders) comprising administration of to a patient in need of such treatment of a therapeutically effective amount of a compound selected from the Summary of the Invention (supra).

Another embodiment provides for a method of preventing obesity in a person at risk for obesity comprising administration to said person of about 0.001 mg to about 100 mg per kg of a compound selected from the Summary of the Invention (supra).

Further preferred compounds of the invention are detailed in the Examples and Table I, infra.

Pharmacology and Utility

Compounds of the invention inhibit the activity of CB1 and, as such, are useful for treating diseases or disorders in which the activity of CB1 contributes to the pathology and/or symptomology of the disease. This invention further provides compounds of this invention for use in the preparation of medicaments for the treatment of diseases or disorders in which CB1 activity contributes to the pathology and/or symptomology of the disease. CB1 mediated diseases or conditions include, but are not limited to, metabolic disorders as well as conditions associated with metabolic disorders including obesity, bulimia nervosa, compulsive eating disorders, diabetes, arteriosclerosis, hypertension, polycystic ovary disease, osteoporosis, cardiovascular disease, osteoarthritis, dermatological disorders, hypertension, insulin resistance, hypercholesterolemia, hypertriglyceridemia, cholelithiasis and sleep disorders, and hyperlipidemic conditions; or psychiatric disorders such as substance abuse, psychosis, depression, anxiety, stress, epilepsy, mania and schizophrenia; or cognitive disorders such as dementia including Alzheimer's disease, memory deficits, short term memory loss and attention deficit disorders; or neurodegenerative disorders such as Parkinson's Disease, cerebral apoplexy and craniocerebral trauma, hypotension, catabolism in connection with pulmonary dysfunction and ventilator dependency; or cardiac dysfunction including valvular disease, myocardial infarction, cardiac hypertrophy and congestive heart failure); or the overall pulmonary dysfunction, transplant rejection, rheumatoid arthritis, migraine, neuropathy, multiple sclerosis, Guillain-Barre syndrome, the inflammatory sequelae of viral encephalitis, cerebral vascular accidents, inflammatory bowel disease, lupus, graft vs. host disease, T-cell mediated hypersensitivity disease, psoriasis, asthma, Hashimoto's thyroiditis, Guillain-Barre syndrome, cancer, contact dermatitis, allergic rhinitis, ischemic or reperfusion injury, head trauma and movement disorders. The compounds are also useful for the treatment of substance abuse disorders, particularly to opiates, alcohol, marijuana, and nicotine including smoking cessation. The compounds are also useful for the treatment of eating disorders by inhibiting excessive food intake and the resulting obesity and complications associated therewith, including left ventricular hypertrophy. The compounds are also useful for the treatment of constipation and chronic intestinal pseudo-obstruction, as well as for the treatment of asthma, osteoporosis, and cirrhosis of the liver.

Marijuana and its derivatives have been used for centuries for medicinal and recreational purposes. A major active ingredient in marijuana and hashish has been determined to be Δ9-Tetrahydrocannabinol (Δ9-THC). The biological action of Δ9-THC and other members of the cannabinoid family occurs through two G-protein coupled receptors termed CB1 and CB2. The CB1 receptor is primarily found in the central and peripheral nervous systems and to a lesser extent in several peripheral organs.

The CB2 receptor is found primarily in lymphoid tissues and cells. Three endogenous ligands for the cannabinoid receptors derived from arachidonic acid have been identified (anandamide, 2-arachidonoyl glycerol, and 2-arachidonyl glycerol ether). Each is an agonist with activities similar to Δ9-THC, including sedation, hypothermia, intestinal immobility, antinociception, analgesia, catalepsy, anti-emesis, and appetite stimulation.

The genes for the respective cannabinoid receptors have each been disrupted in mice. The CB1 receptor knockout mice appeared normal and fertile. They were resistant to the effects of Δ9-THC and demonstrated a strong reduction in the reinforcing properties of morphine and the severity of withdrawal syndrome. They also demonstrated reduced motor activity and hypoalgesia. The CB2 receptor knockout mice were also healthy and fertile. They were not resistant to the central nervous system mediated effects of administered Δ9-THC. There were some effects on immune cell activation, reinforcing the role for the CB2 receptor in immune system functions.

Excessive exposure to Δ9-THC can lead to overeating, psychosis, hypothermia, memory loss, and sedation.

Treatment of asthma with CB1 receptor modulators (such as CB1 inverse agonists) is supported by the finding that presynaptic cannabinoid CB1 receptors mediate the inhibition of noradrenalin release.

Treatment of cirrhosis of the liver with CB1 receptor modulators is supported by the finding that a CB1 receptor modulator will reverse the low blood pressure observed in rats with carbon tetrachloride-induced liver cirrhosis and will lower the elevated mesenteric blood flow and portal vein pressure.

In accordance with the foregoing, the present invention further provides a method for preventing or treating any of the diseases or disorders described above in a subject in need of such treatment, which method comprises administering to said subject a therapeutically effective amount (See, "*Administration and Pharmaceutical Compositions*", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount can vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrollidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions can be sterilized and/or contain adjuvants, such as preserving, stabilizing, wetting or emulsifying agents, solution promoters, salts for regulating the osmotic pressure and/or buffers. In addition, they can also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations can also be used. Suitable formulations for topical application, e.g., to the skin and eyes, are preferably aqueous solutions, ointments, creams or gels well-known in the art. Such can contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other substances used in the treatment of diseases or disorders, such as, psychosis, memory deficit, cognitive disorders, migraine, neuropathy, neuroinflammatory disorders, cerebral vascular accidents, head trauma, anxiety disorders, stress, epilepsy, Parkinson's disease, schizophrenia, substance abuse disorders such as smoking cessation, osteoporosis, constipation, chronic intestinal pseudo-obstruction, cirrhosis of the liver, asthma, obesity, and other eating disorders associated with excessive food intake, obesity, etc. (see "Pharmacology and Utility", supra). Where the compounds of the invention are administered in conjunction with other therapies, dosages of the co-administered compounds will of course vary depending on the type of co-drug employed, on the specific drug employed, on the condition being treated and so forth.

A combined preparation or pharmaceutical composition can comprise a compound of the invention as defined above or a pharmaceutical acceptable salt thereof and at least one active ingredient selected from:

a) anti-diabetic agents such as insulin, insulin derivatives and mimetics; insulin secretogogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker, a thiazolidone derivative (glitazone) such as pioglitazone, rosiglitazone, or (R)-1-{4-[5-methyl-2-(4-trifluoromethyl-phenyl)-oxazol-4-ylmethoxy]-benzenesulfonyl}-2,3-dihydro-1H-indole-2-carboxylic acid described in the patent application WO 03/043985, as compound 19 of Example 4, a non-glitazone type PPAR gamma agonist e.g. GI-262570; Diacylglycerol acetyltransferase (DGAT) inhibitors such as those disclosed in WO 2005044250, WO 2005013907, WO 2004094618 and WO 2004047755;

b) hypolipidemic agents such as 3-hydroxy-3-methyl-glutaryl coenzyme A (HMG-CoA) reductase inhibitors, e.g., lovastatin and related compounds such as those disclosed in U.S. Pat. No. 4,231,938, pitavastatin, simvastatin and related compounds such as those disclosed in U.S. Pat. Nos. 4,448,784 and 4,450,171, pravastatin and related compounds such as those disclosed in U.S. Pat. No. 4,346,227, cerivastatin, mevastatin and related compounds such as those disclosed in U.S. Pat. No. 3,983,140, velostatin, fluvastatin, dalvastatin, atorvastatin, rosuvastatin and related statin compounds disclosed in U.S. Pat. No. 5,753,675, rivastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propanephosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a SCD-1 inhibitor as disclosed in WO2005011655, a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine;

d) anti-hypertensive agents such as loop diuretics such as ethacrynic acid, furosemide and torsemide; diuretics such as thiazide derivatives, chlorothiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren, terlakiren, ditekiren, RO 66-1132, RO-66-1168; beta-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; aldosterone synthase inhibitors; and dual ET/AII antagonist such as those disclosed in WO 00/01389.

e) a HDL increasing compound;

f) Cholesterol absorption modulator such as Zetia® and KT6-971;

g) Apo-A1 analogues and mimetics;

h) thrombin inhibitors such as Ximelagatran;

i) aldosterone inhibitors such as anastrazole, fadrazole, eplerenone;

j) Inhibitors of platelet aggregation such as aspirin, clopidogrel bisulfate;

k) estrogen, testosterone, a selective estrogen receptor modulator, a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, compounds decreasing the protein kinase activity such as a PDGF receptor tyrosine kinase inhibitor preferably Imatinib ({N-{5-[4-(4-methyl-piperazino-methyl)-benzoylamido]-2-methylphenyl}-4-(3-pyridyl)-2-pyrimidine-amine}) described in the European patent application EP-A-0 564 409 as example 21 or 4-Methyl-N-[3-(4-methyl-imidazol-1-yl)-5-trifluoromethyl-phenyl]-3-(4-pyridin-3-yl-pyrimidin-2-ylamino)-benzamide described in the patent application WO 04/005281 as example 92; and m) an agent interacting with a 5-HT$_3$ receptor and/or an agent interacting with 5-HT$_4$ receptor such as tegaserod described in the U.S. Pat. No. 5,510,353 as example 13, tegaserod hydrogen maleate, cisapride, cilansetron;

n) an agent for treating tobacco abuse, e.g., nicotine receptor partial agonists, bupropion hypochloride (also known under the tradename Zyban®) and nicotine replacement therapies;

o) an agent for treating erectile dysfunction, e.g., dopaminergic agents, such as apomorphine), ADD/ADHD agents (e.g., Ritalin®, Strattera®, Concerta® and Adderall®);

p) an agent for treating alcoholism, such as opioid antagonists (e.g., rialtrexone (also known under the tradename ReVia®) and nalmefene), disulfiram (also known under the tradename Antabuse®), and acamprosate (also known under the tradename Campral®)). In addition, agents for reducing alcohol withdrawal symptoms may also be co-administered, such as benzodiazepines, beta-blockers, clonidine, carbamazepine, pregabalin, and gabapentin (Neurontin®);

q) other agents that are useful including anti-inflammatory agents (e.g., (COX-2 inhibitors); antidepressants (e.g., fluoxetine hydrochloride (Prozac®)); cognitive improvement agents (e.g., donepezil hydrochloride (Aircept®) and other acetylcholinesterase inhibitors); neuroprotective agents (e.g., memantine); antipsychotic medications (e.g., ziprasidone (Geodon®), risperidone (Risperdal®), and olanzapine (Zyprexa®));

or, in each case a pharmaceutically acceptable salt thereof; and optionally a pharmaceutically acceptable carrier.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

In the following schemes, several methods of preparing the compounds of the present invention are illustrative. One of skill in the art will appreciate that these methods are representative, and in no way inclusive of all methods for preparing the compounds of the present invention. The radicals in the schemes are as described in the Summary of the Invention (supra). In each of the reaction schemes below, R$_1$ is 4-chlorophenyl.

An illustration of the synthesis of the compounds in the present invention of Formula Ia is given in Reaction Scheme 1. An amine 2-a is reacted with an acid chloride 2-b (or its corresponding carboxylic acid) under standard amide formation conditions to provide 2-c. The amide 2-c is treated with chlorination reagents, such as thionyl chloride, oxalyl chloride, oxyphosphorus trichloride and etc., to provide 2-d. The imidoyl chloride 2-d is condensed with 5-amino-4-pyrazole-carboxylate 2-e (R$^a$ is methyl or ethyl) upon heating in the presence of a strong Lewis acid (e.g. TiCl$_4$) to provide an amidine intermediate, which is cyclized in situ to 1,5-dihydro-pyrazolo[3,4-d]pyrimidin-4-one 2-f. Amide coupling reactions were carried out under standard conditions, such as those described in (1) M. Bodanszky et al "The Practice of Peptide Synthesis", Springer-Verlay 2$^{nd}$ ed. 1994; (2) A. R. Chamberlin, Chem. Rev. 1997, 97, 2243-66.

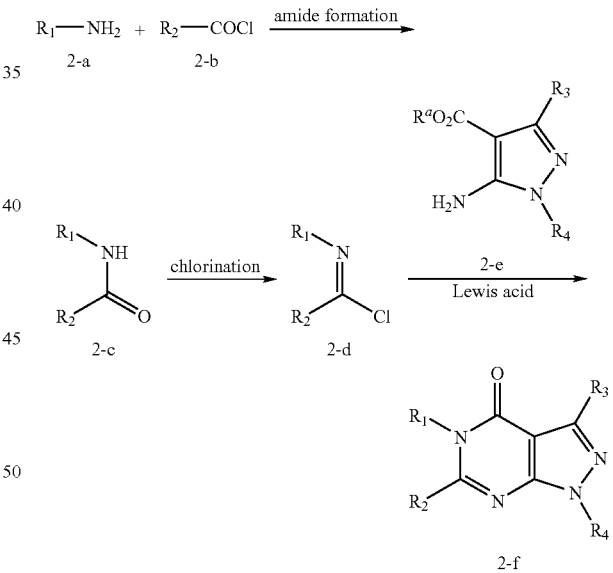

5-amino-4-pyrazole-carboxylates 2-e used in this invention are synthesized as described in (a) Abass, M. Phosphorus, Sulfur and Silicon and the Related Elements (2003), 178(7), 1413-1432; (b) Beck, James R. et al J. Heterocyclic Chem. (1987), 24(3), 693-5; (c) Sunder, S. et al J. Heterocyclic Chem. (1980), 17(7), 1527-9; (d) Beck, James R. et al J. Heterocyclic Chem. (1988), 25(3), 955-8; (e) Ryckmans, T. et al Tetrahedron (1997), 53(5), 1729-1734; (f) Organ, Michael G. et al J. Combi. Chem. (2003), 5(2), 118-124; (g) Kopp, M. et al J. Heterocyclic Chem. (2001), 38(5), 1045-1050.

An illustration of the synthesis of the compounds in the present invention of Formula Ic is given in Reaction Scheme 2. Ethyl cyanoglycoxylate-2-oxime 3-a is reduced according to literature precedent (De Meester et al *Heterocycl. Chem.* 1987, 24, 441) to 2-cyanoglycine ethyl ester 3-b. Amine 3-b is then condensed with triethyl orthoformate. Without purification, the resulting cyano[(1-ethoxymethylene)amino]acetate 3-c is treated directly with amine $R_4NH_2$ to provide 5-amino-1H-imidazole-4-carboxylate 3-d. Syntheses of compound 3-d are also described in (a) Collins. M. et al *Inorg. Chem. Commun.* 2000, 3, 453; (b) Herr, R. et al *J. Org. Chem.* 2002, 67(1), 188-193; (c) Suwinski, J. et al *Eur. J. Org. Chem.* 2003, (6), 1080-1084. 5-Amino-1H-imidazole-4-carboxylate 3-d is converted to 1,9-dihydro-purin-6-one 3-e by the procedures described in Scheme 2.

Reaction Scheme 2

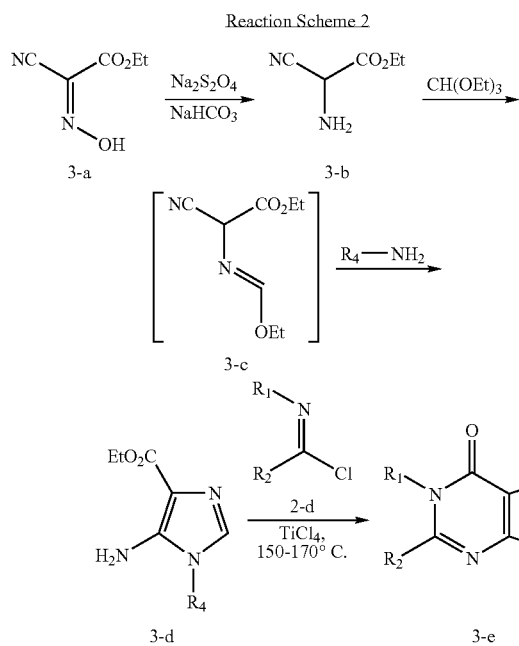

Compounds in the present invention of Formula Ia can also be made by the procedures given in Reaction Scheme 3. 5-Aminopyrazole-4-carboxylate 2-e reacts with acid chloride $R_2(C=O)Cl$ giving the N,N-diacylated intermediate 4-b which is then treated with an excess amount of lithium amide $R_1NHLi$ to form intermediate 4-c ($R^a$ is methyl or ethyl). Ring closure of 4-c upon treatment with trimethylsilyl chloride and triethylamine gives 1,5-dihydro-pyrazolo[3,4-d]pyrimidin-4-one 2-f. A procedure similar to the annulation step used here is described by Miyata, K. et al U.S. Pat. No. 5,922,866. Other procedures to effect the conversion of compound 4-c to compound 2-f are described in (a) Brzozowski Z. et al *J. Med. Chem.* (2002), 45(2), 430-37; (b) Zaher, H. A. et al *Indian J. Chem.* (1974), 12(11), 1212-15.

Reaction Scheme 3

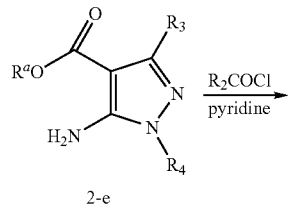

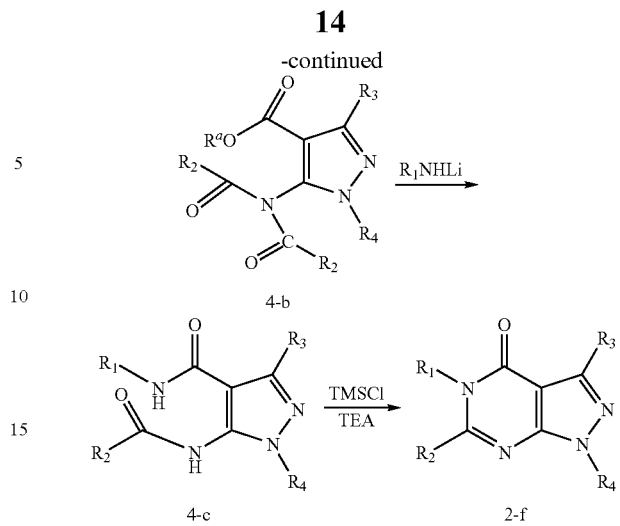

Reaction scheme 4 illustrates the preparation of bi-aryl or heteroaryl-phenyl derivatives. Under the standard Suzuki or Stille coupling conditions, Bromo (or iodo) substituted 1,9-dihydro-purin-6-one 5-a is coupled with suitable boronic acids or stannane to form desired purinone derivatives 5-b.

Reaction Scheme 4

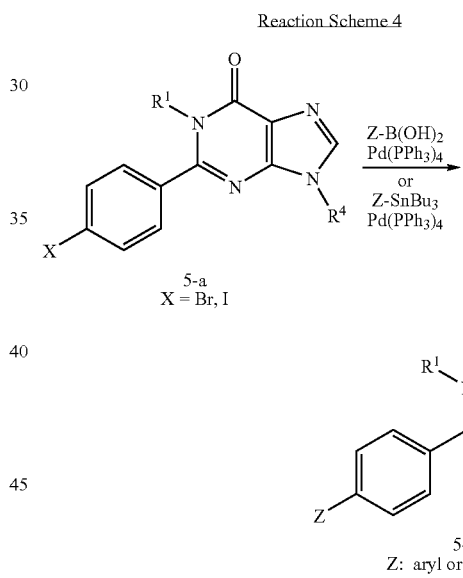

Reaction scheme 5 describes the synthesis of the compounds with various aryl or heteroaryl $R^4$ by a modified copper complex-catalyzed cross coupling reaction of arylboronic acids with imidazoles developed from J. Collman's labolatory (ref. *Org. Lett.* 2000, 2, 1233.) The starting material required for this synthesis, ethyl 4-amino-1-benzylimidazole carboxylate, is readily prepared in a large scale from commercially available N-benzylglycine ethyl ester (ref. *Synthesis* 1995, 855).

Reaction Scheme 5

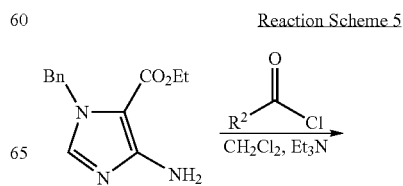

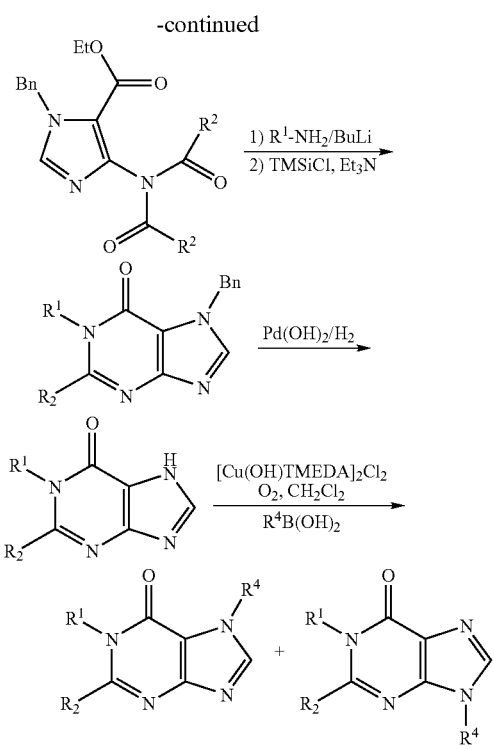

Detailed descriptions of the synthesis of compounds of the Invention are given in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme 1, 2, 3, 4 or 5; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following intermediates (Reference Examples) and Examples that illustrate the preparation of compounds of the invention.

Reference 1

Preparation of 5-Amino-1-cyclohexyl-1H-pyrazole-4-carboxylic acid ethyl ester

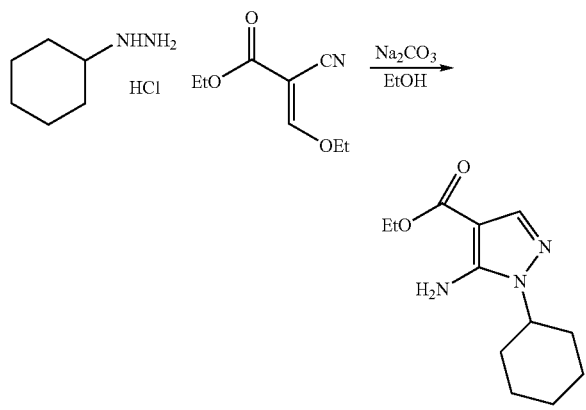

To a round bottom flask is added cyclohexyl-hydrazine hydrochloride (4.5 g, 30 mmol), 2-cyano-3-ethoxy-acrylic acid ethyl ester (5.1 g, 30 mmol), sodium bicarbonate (2.6 g, 30.9 mmol) and 40 mL of ethanol. The mixture is heated to 80° C. for 1 hour, cooled down to room temperature and concentrated. The residue is dissolved in chloroform and washed with water, dried over sodium sulfate. After removal of the solvent, the solid is recrystallized from ethyl acetate: $^1$HNMR (CDCl$_3$): δ 7.40 (1 H, s), 4.77 (2 H, brs), 4.05 (2 H, q, J=7.2 Hz), 3.50 (1 H, m), 1.61-1.71 (6 H, m), 1.50 (1 H, m), 1.02-1.21 (3 H, m), 1.11 (3 H, t, J= 7.2 Hz).

Example 2

6-[4-(6-amino-pyridin-3-yl)phenyl]-5-(4-chlorophenyl)-3-methanesulfonyl-1-phenyl-1,5-dihydropyrazolo[3,4-d]pyrimidin-4-one

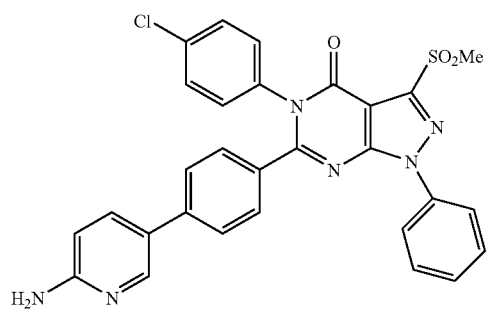 [SMILES: CS(=O)(=O)c1nn(-c2ccccc2)c2nc(-c3ccc(-c4ccc(N)nc4)cc3)n(-c3ccc(Cl)cc3)c(=O)c12]

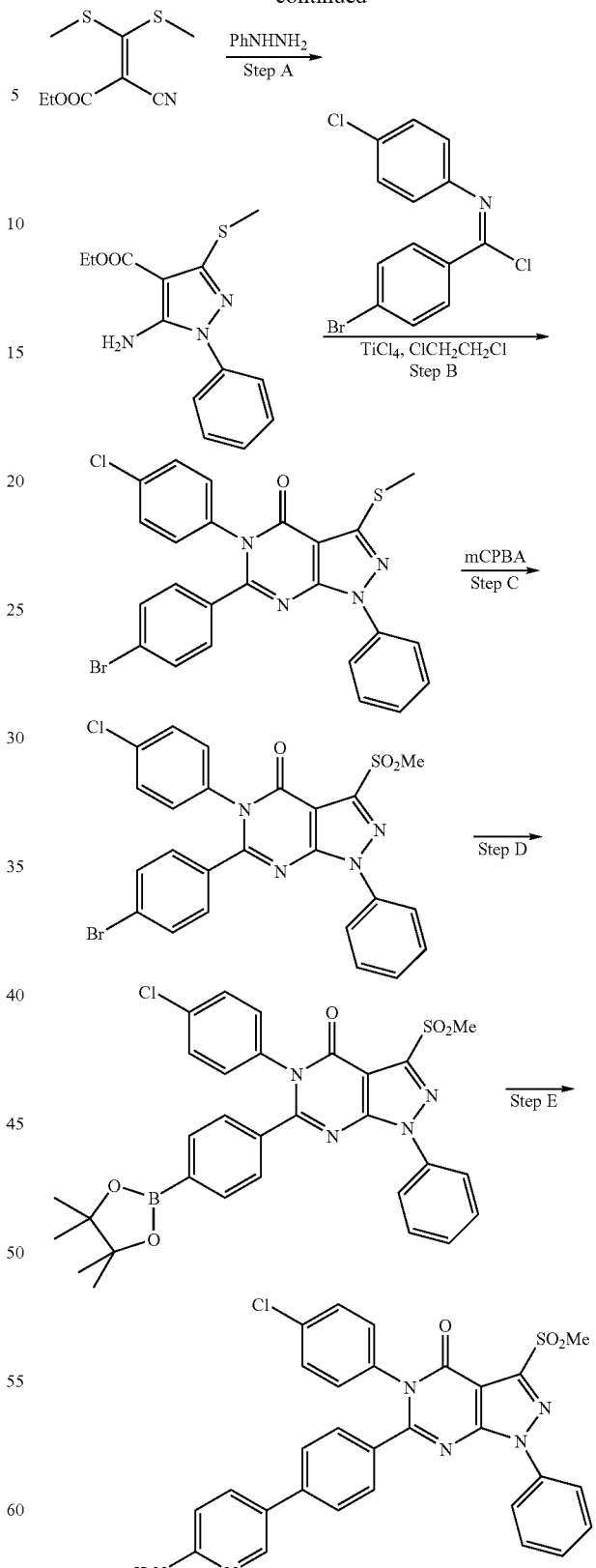

Step A: To a solution of 2-cyano-3,3-bis-methylsulfanyl-acrylic acid ethyl ester (5.00 g, 23.0 mmol) in dry ethanol (100 mL) is added phenylhydrazine (2.28 mL, 23.0 mmol).

The reaction mixture is heated to reflux for 2 h before removal of the solvent. The resulting solid is recrystallized from EtOH (20 mL) to provide 5-amino-3-methylsulfanyl-1-phenyl-1H-pyrazole-4-carboxylic acid ethyl ester as a white solid product; HPLC-MS calculated for $C_{13}H_{15}N_3O_2S$ (M+H$^+$) 278.1, found 278.1.

Step B: A mixture of 4-bromo-N-(4-chloro-phenyl)-benzamide (1.14 g, 3.67 mmol) in $SOCl_2$ (4.5 mL) is heated to 80° C. for 2 h before $SOCl_2$ is removed in vacuo. The resulted imidoyl chloride intermediate is dissolved in anhydrous dichloroethane (18 mL) and transferred into a sealed tube. After adding 5-amino-3-methylsulfanyl-1-phenyl-1H-pyrazole-4-carboxylic acid ethyl ester (1.12 g, 4.04 mmol) and $TiCl_4$ (0.80 mL, 7.3 mmol), the reaction tube is sealed and heated at 150° C. overnight. After cooling down to room temperature the reaction mixture is poured into water (200 mL) and extracted with chloroform (3×100 mL). The organic layers are combined, washed with brine, dried over $MgSO_4$, concentrated, and purified by silica gel chromatography to provide 6-(4-bromo-phenyl)-5-(4-chloro-phenyl)-3-methylsulfanyl-1-phenyl-1,5-dihydro-pyrazolo[3,4-d]pyrimidin-4-one as a white solid product; HPLC-MS calculated for $C_{24}H_{16}BrClN_4OS$ (M+H$^+$) 523.0, found 523.0.

Step C: To a solution of 6-(4-bromo-phenyl)-5-(4-chloro-phenyl)-3-methylsulfanyl-1-phenyl-1,5-dihydro-pyrazolo[3,4-d]pyrimidin-4-one (1.00 g, 1.91 mmol) in $CH_2Cl_2$ (7.5 mL) is added mCPBA (1.28 g, 5.73 mmol). The mixture is stirred at room temperature overnight before removal of the solvent. The residue is taken into saturated $NaHCO_3$ aqueous solution and filtered. The precipitate is washed with water, small amount of EtOAc, and air dried to provide crude 6-(4-bromo-phenyl)-5-(4-chloro-phenyl)-3-methanesulfonyl-1-phenyl-1,5-dihydro-pyrazolo[3,4-d]pyrimidin-4-one as a white solid product, which is used in next step without further purification; HPLC-MS calculated for $C_{24}H_{16}BrClN_4O_3S$ (M+H$^+$) 555.0, found 555.0.

Step D: A reaction tube charged with 6-(4-bromo-phenyl)-5-(4-chloro-phenyl)-3-methanesulfonyl-1-phenyl-1,5-dihydro-pyrazolo[3,4-d]pyrimidin-4-one (900 mg, 1.62 mmol), bis(pinacolato)diboron (473 mg, 1.86 mmol), KOAc (477 mg, 4.86 mmol), and Pd(dppf)$_2$Cl$_2$ (66.1 mg, 0.08 mmol) is purged with nitrogen. Anhydrous DMF (10 mL) is added via syringe. The reaction mixture is heated at 100° C. for 2 h, cooled down to room temperature, poured into water (100 mL), and extracted with EtOAc (3×100 mL). The combined organic phase is washed with brine, dried over $MgSO_4$, concentrated, and purified by silica gel chromatography to provide 5-(4-chloro-phenyl)-3-methanesulfonyl-1-phenyl-6-[4-(4,4,5,5-tetramethyl-[1,3,2]dioxaborolan-2-yl)-phenyl]-1,5-dihydro-pyrazolo[3,4-d]pyrimidin-4-one as a white solid product; HPLC-MS calculated for $C_{30}H_{28}BClN_4O_5S$ (M+H$^+$) 603.2, found 603.2.

Step E: A reaction tube charged with 5-(4-chloro-phenyl)-3-methanesulfonyl-1-phenyl-6-[4-(4,4,5,5-tetramethyl-[1,3,2]dioxaborolan-2-yl)-phenyl]-1,5-dihydro-pyrazolo[3,4-d]pyrimidin-4-one (200.0 mg, 0.332 mmol), 2-amino-5-bromopyridine (114.8 mg, 0.664 mmol), $Cs_2CO_3$ (162.1 mg, 0.498 mmol), and Pd(dppf)$_2$Cl$_2$ (54.2 mg, 0.066 mmol) is purged with nitrogen. Anhydrous DMF (3.3 mL) is added via syringe. The reaction mixture is heated at 80° C. for 2 h, cooled down to room temperature, poured into water (30 mL) and EtOAc (30 mL). The insoluble solid is filtered off and the two layers of the filtrate are separated. The aqueous layer is extracted with EtOAc (2×30 mL). The combined organic phase is washed with brine, dried over $MgSO_4$, concentrated, and purified by reverse phase HPLC to provide 6-[4-(6-amino-pyridin-3-yl)-phenyl]-5-(4-chloro-phenyl)-3-methanesulfonyl-1-phenyl-1,5-dihydro-pyrazolo[3,4-d]pyrimidin-4-one as a light yellow solid product; $^1$H NMR (CDCl$_3$, 400 MHz) δ 8.21 (d, 1H), 8.11 (d, 2H), 7.71 (dd, 1H), 7.54 (t, 2H), 7.44 (t, 1H), 7.41 (m, 4H), 7.36 (d, 2H), 7.16 (d, 2H), 6.67 (d, 1H), 5.22 (br, 2H), 3.55 (s, 3H); HPLC-MS calculated for $C_{29}H_{21}ClN_6O_3S$ (M+H+) 569.1, found 569.1.

Example 3

6-[4-(6-amino-1-oxy-pyridin-3-yl)-phenyl]-5-(4-chloro-phenyl)-1-phenyl-1,5-dihydro-pyrazolo[3,4-d]pyrimidin-4-one

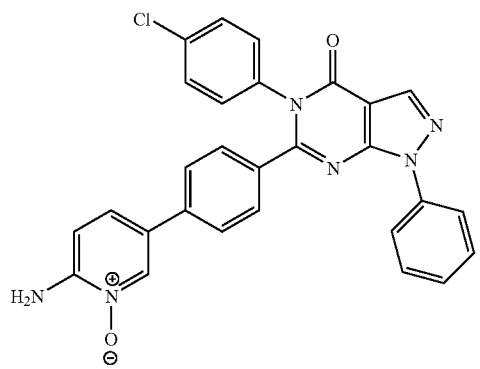 [SMILES: Nc1ccc(-c2ccc(-c3nc4c(cnn4-c4ccccc4)c(=O)n3-c3ccc(Cl)cc3)cc2)c[n+]1[O-]]

6-[4-(6-Amino-pyridin-3-yl)-phenyl]-5-(4-chloro-phenyl)-1-phenyl-1,5-dihydro-pyrazolo[3,4-d]pyrimidin-4-one is prepared as described in Example 2 (Steps B, D and E), using commercially available 5-amino-1-phenyl-1H-pyrazole-4-carboxylic acid ethyl ester instead of 5-amino-3-methylsulfanyl-1-phenyl-1H-pyrazole-4-carboxylic acid ethyl ester; $^1$H NMR (CDCl$_3$, 400 MHz) δ 8.33 (s, 1H), 8.28 (d, 1H), 8.16 (d, 2H), 7.66 (dd, 1H), 7.51 (t, 2H), 7.40 (m, 4H), 7.35 (m, 3H), 7.13 (d, 2H), 6.59 (d, 1H), 4.72 (br, 2H); HPLC-MS calculated for $C_{28}H_{19}ClN_6O$ (M+H$^+$) 491.1, found 491.1.

To a solution of 6-[4-(6-amino-pyridin-3-yl)-phenyl]-5-(4-chloro-phenyl)-1-phenyl-1,5-dihydro-pyrazolo[3,4-d]pyrimidin-4-one (30.0 mg, 0.061 mmol) in $CH_2Cl_2$ (0.6 mL) are added mCPBA (23.3 mg, 0.104 mmol) and $NaHCO_3$ (17.5 mg, 0.208 mmol). The reaction mixture is stirred at room temperature overnight before taken in 10% $Na_2HSO_3$ aqueous solution (5 mL) and extracted with EtOAc (3×5 mL). The combined organic layer is washed with saturated $NaHCO_3$ aqueous solution, concentrated, and purified by preparative TLC to provide 6-[4-(6-ammo-1-oxy-pyridin-3-yl)-phenyl]-5-(4-chloro-phenyl)-1-phenyl-1,5-dihydro-pyrazolo[3,4-d]pyrimidin-4-one as a yellow solid product; $^1$H NMR (CDCl$_3$, 400 MHz) δ 8.35 (d, 1H), 8.34 (s, 1H), 8.14 (d, 2H), 7.51 (t, 2H), 7.42 (d, 2H), 7.38-7.33 (m, 6H), 7.12 (d, 2H), 6.86 (d, 1H), 5.79 (br, 2H); HPLC-MS calculated for $C_{28}H_{19}ClN_6O_2$ (M+H$^+$) 507.1, found 507.1.

Example 5

4-[5-(4-Chloro-phenyl)-4-oxo-1-phenyl-4,5-dihydro-1H-pyrazolo[3,4-d]pyrimidin-6-yl]-benzene sulfonamide

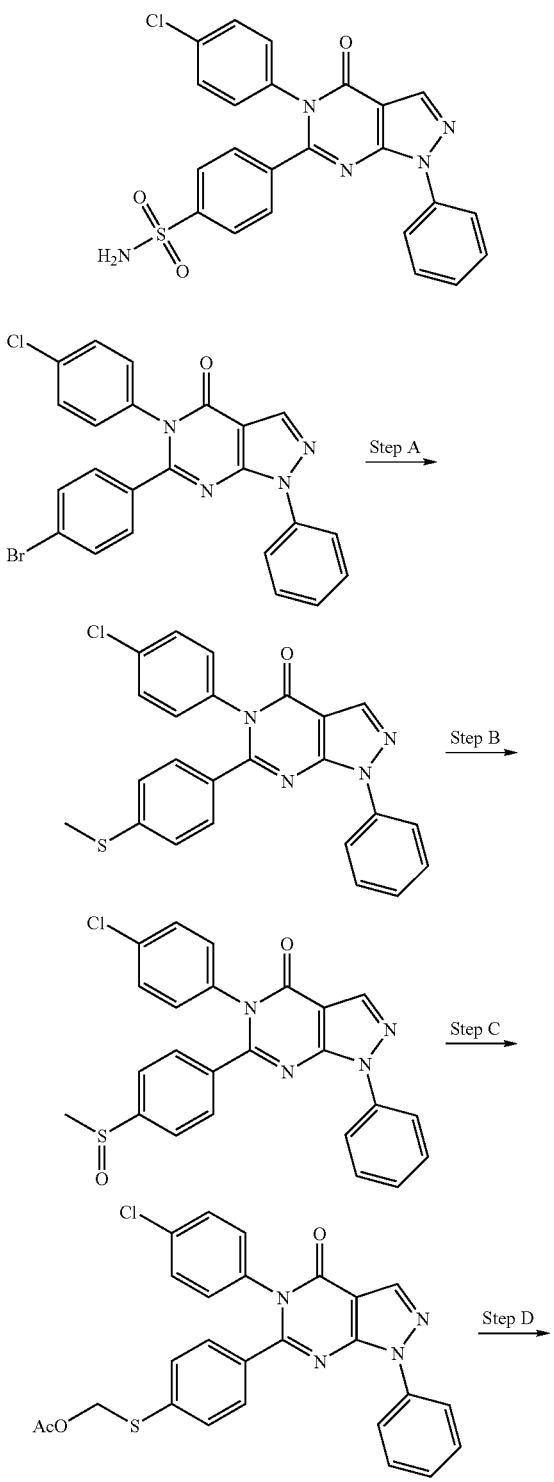

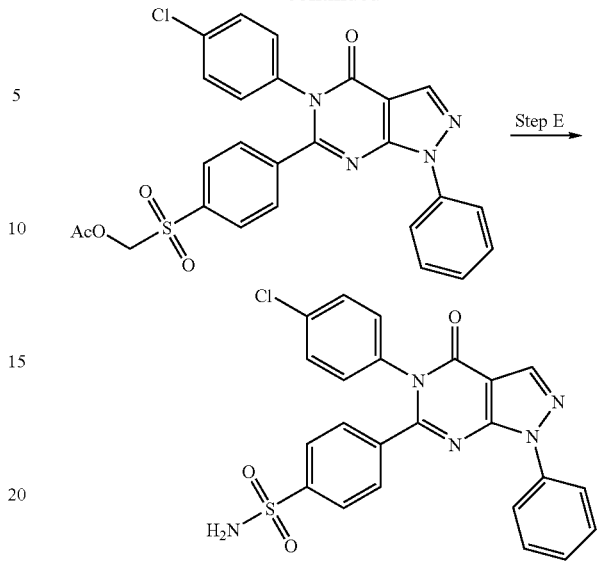

Step A: To a solution of 6-(4-bromo-phenyl)-5-(4-chloro-phenyl)-1-phenyl-1,5-dihydro-pyrazolo[3,4-d]pyrimidin-4-one (2.50 g, 5.23 mmol) in dry N,N-dimethyl-formamide (20 mL), sodium thiomethoxide (0.55 g, 7.84 mmol) is added and the resulting mixture is stirred at 80° C. After 1.5 h, the reaction mixture is concentrated and the crude product obtained is purified by column chromatography (silica gel, 60-120 mesh) to afford 5-(4-chloro-phenyl)-6-(4-methylsulfanyl-phenyl)-1-phenyl-1,5-dihydro-pyrazolo[3,4-d]pyrimidin-4-one.

Step B: To a solution of 5-(4-chloro-phenyl)-6-(4-methylsulfanyl-phenyl)-1-phenyl-1,5-dihydro-pyrazolo[3,4-d]pyrimidin-4-one (2.10 g, 4.72 mmol) in dry dichloromethane (36 mL) and methanol (12 mL), magnesium monoperoxy phthalate hexahydrate (1.16 g, 2.36 mmol) is added at 0° C. and the resulting mixture is stirred for 3 h at that temperature. The reaction mixture is quenched with the addition of 10% sodium bicarbonate solution and extracted with dichloromethane (3×). The organic part separated is dried ($Na_2SO_4$) and concentrated. The crude product is purified by column chromatography (silica gel, 60-120 mesh) to afford 5-(4-chloro-phenyl)-6-(4-methanesulfinyl-phenyl)-1-phenyl-1,5-dihydro-pyrazolo[3,4-d]pyrimidin-4-one.

Step C: To a solution of 5-(4-chloro-phenyl)-6-(4-methanesulfinyl-phenyl)-1-phenyl-1,5-dihydro-pyrazolo[3,4-d]pyrimidin-4-one (1.20 g, 2.60 mmol) in dry acetic anhydride (12 mL) sodium acetate (0.800 g, 9.76 mmol) is added and the resulting mixture is heated to reflux. After 5 h, the reaction mixture is concentrated. The crude product is purified by column chromatography (silica gel, 60-120 mesh) to afford (4-(5-(4-chlorophenyl)-4-oxo-1-phenyl-4,5-dihydro-1H-pyrazolo[3,4-d]pyrimidin-6-yl)phenylthio)methyl acetate.

Step D: To a solution of (4-(5-(4-chlorophenyl)-4-oxo-1-phenyl-4,5-dihydro-1H-pyrazolo[3,4-d]pyrimidin-6-yl)phenylthio)methyl acetate (1.00 g, 1.98 mmol) in dry dichloromethane (30 mL) and methanol (10 mL), magnesium monoperoxy phthalate hexahydrate (1.08 g, 2.18 mmol) is added at 0° C. and the resulting mixture is stirred for 18 h at rt. Then the reaction mixture is quenched with the addition of 10% sodium bicarbonate solution and extracted with dichloromethane (3×). The organic part separated is dried ($Na_2SO_4$) and concentrated. The crude product is purified by column chromatography (silica gel, 60-120 mesh) to afford (4-(5-(4- chlorophenyl)-4-oxo-1-phenyl-4,5-dihydro-1H-pyrazolo[3,4-d]pyrimidin-6-yl)phenylsulfonyl)methyl acetate.

Step E: To a suspension of (4-(5-(4-chlorophenyl)-4-oxo-1-phenyl-4,5-dihydro-1H-pyrazolo[3,4-d]pyrimidin-6-yl)phenylsulfonyl)methyl acetate (0.83 g, 1.55 mmol) in dry methanol (30 mL), sodium acetate (1.01 g, 12.41 mmol) is added with stirring. After 15 min at rt, dry potassium carbonate (0.599 g, 4.35 mmol) is added and the stirring continued for 1.5 h. Then hydroxylamine O-sulfonic acid (0.701 g, 6.20 mmol) is added with stirring. After 2 h, the reaction mixture is poured into ethyl acetate-saturated sodium bicarbonate solution mixture. The aqueous part is extracted with ethyl acetate (3×). The combined organic part is dried ($Na_2SO_4$) and concentrated. The crude product obtained is purified by preparative HPLC chromatography to afford 4-[5-(4-chloro-phenyl)-4-oxo-1-phenyl-4,5-dihydro-1H-pyrazolo[3,4-d]pyrimidin-6-yl]-benzene sulfonamide. $^1$H NMR ($CD_3OD$, 400 MHz) δ 8.33 (s, 1H), 8.10 (d, 2H), 7.79 (d, 2H), 7.58 (d, 2H), 7.51 (m, 2H), 7.35 (m, 3H), 7.29 (m, 2H); LC-MS calculated for $C_{23}H_{16}ClN_5O_3S$ (M+H$^+$) 478.1, found 478.0.

Example 6

3-(6-(4-bromophenyl)-5-(4-chlorophenyl)-4-oxo-4,5-dihydro-1H-pyrazolo[3,4-d]pyrimidin-1-yl)benzenesulfonamide

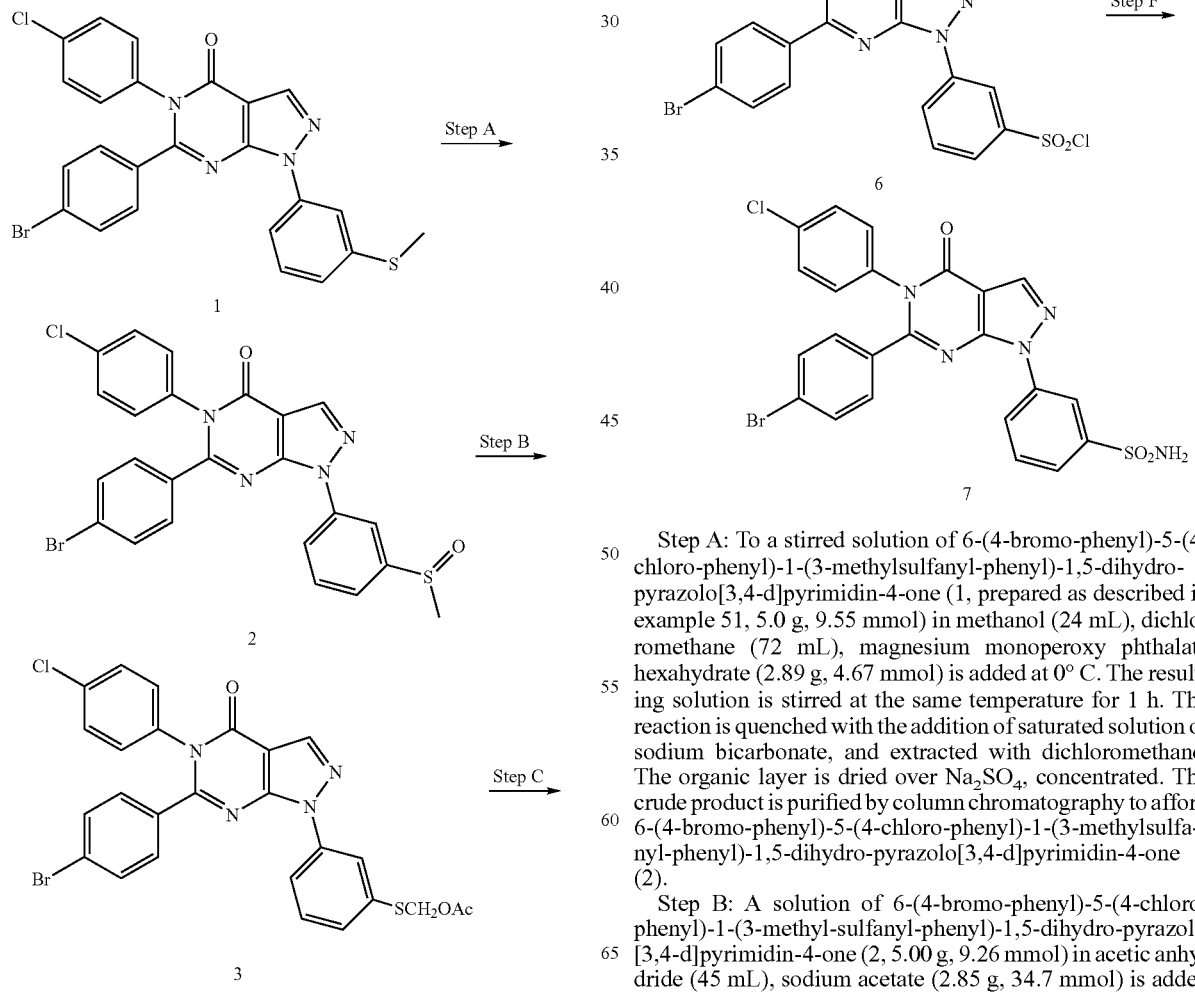

Step A: To a stirred solution of 6-(4-bromo-phenyl)-5-(4-chloro-phenyl)-1-(3-methylsulfanyl-phenyl)-1,5-dihydro-pyrazolo[3,4-d]pyrimidin-4-one (1, prepared as described in example 51, 5.0 g, 9.55 mmol) in methanol (24 mL), dichloromethane (72 mL), magnesium monoperoxy phthalate hexahydrate (2.89 g, 4.67 mmol) is added at 0° C. The resulting solution is stirred at the same temperature for 1 h. The reaction is quenched with the addition of saturated solution of sodium bicarbonate, and extracted with dichloromethane. The organic layer is dried over $Na_2SO_4$, concentrated. The crude product is purified by column chromatography to afford 6-(4-bromo-phenyl)-5-(4-chloro-phenyl)-1-(3-methylsulfanyl-phenyl)-1,5-dihydro-pyrazolo[3,4-d]pyrimidin-4-one (2).

Step B: A solution of 6-(4-bromo-phenyl)-5-(4-chloro-phenyl)-1-(3-methyl-sulfanyl-phenyl)-1,5-dihydro-pyrazolo[3,4-d]pyrimidin-4-one (2, 5.00 g, 9.26 mmol) in acetic anhydride (45 mL), sodium acetate (2.85 g, 34.7 mmol) is added and the resulting mixture is then heated at reflux for 5 h. The reaction mixture is concentrated to a dry residue and it is taken in ethyl acetate, washed with 10% sodium bicarbonate solution. The organic layer is washed with brine, dried over Na$_2$SO$_4$, concentrated, and purified by column chromatography to provide acetic acid 3-[6-(4-bromo-phenyl)-5-(4-chloro-phenyl)-4-oxo-4,5-dihydro-pyrazolo[3,4-d]pyrimidin-1-yl]-phenyl sulfanyl methyl ester (3).

Step C: To a stirred solution of acetic acid 3-[6-(4-bromo-phenyl)-5-(4-chloro-phenyl)-4-oxo-4,5-dihydro-pyrazolo[3,4-d]pyrimidin-1-yl]-phenyl sulfanyl methyl ester (3, 5.2 g, 8.93 mmol) in methanol (50 mL), dichloromethane (150 mL), magnesium monoperoxy phthalate hexahydrate (4.86 g, 9.83 mmol) is added at 0° C. The resulting solution is stirred at rt for 2 h. The reaction is quenched with the addition of saturated solution of sodium bicarbonate, and extracted with dichloromethane. The organic layer is dried over Na$_2$SO$_4$, concentrated. The crude product is purified by column chromatography to afford acetic acid 3-[6-(4-bromo-phenyl)-5-(4-chloro-phenyl)-4-oxo-4,5-dihydro-pyrazolo[3,4-d]pyrimidin-1-yl]-benzene sulfonyl methyl ester (4).

Step D: To a stirred solution of acetic acid 3-[6-(4-bromo-phenyl)-5-(4-chloro-phenyl)-4-oxo-4,5-dihydro-pyrazolo[3,4-d]pyrimidin-1-yl]-benzene sulfonyl methyl ester (17, 5 g, 8.14 mmol) in methanol (25 mL), tetrahydrofuran (50 mL), 1 N aqueous sodium hydroxide solution (8.12 mL) is added at 0° C. The reaction mixture as stirred at that temperature for 1.5 h. Then it is concentrated to a dry residue. It is coevaporated with toluene to get rid of solvent traces. The sulfinate salt (5) obtained is taken to next stage without further purification.

Step E: To a stirred solution of sulfinate salt (5, 2.5 g, 4.43 mmol) in dichloromethane (60 mL), sulfuryl chloride (0.658 g, 4.87 mmol) is added at 0° C. The reaction mixture as stirred at that temperature for 1.5 h. Then the reaction mixture is diluted with water and dichloromethane. The organic layers separated is dried, and concentrated to afford the sulfonyl chloride product (6).

Step F: To a stirred solution of sulfonyl chloride (6, 2.3 g, 3.99 mmol) in dry tetrahydrofuran (60 mL), aqueous ammonia solution (8 mL, 25% in water) is added at 0° C. The reaction mixture as stirred at that temperature for 45 min. Then the reaction mixture is diluted with water and dichloromethane. The organic layers separated is dried, and concentrated to afford the 3-[6-(4-bromo-phenyl)-5-(4-chloro-phenyl)-4-oxo-4,5-dihydro-pyrazolo[3,4-d]pyrimidin-1-yl]-benzene sulfonamide (7). HPLC-MS calculated for C$_{23}$H$_{15}$BrClN$_5$O$_3$S (M+H$^+$) 558.0, found 557.9.

Example 7

5-[4-(6-amino-pyridin-3-yl)-phenyl]-6-(4-chloro-phenyl)-7-oxo-3-phenyl-6,7-dihydro-pyrazolo[4,3-d]pyrimidine-1-carboxylic acid dimethylamide

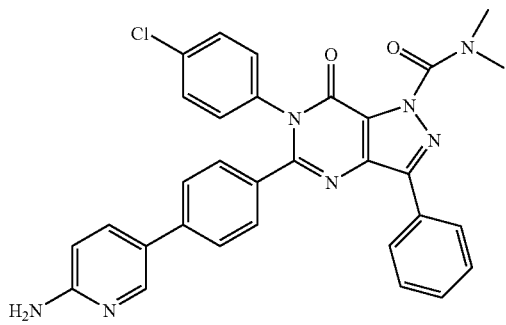

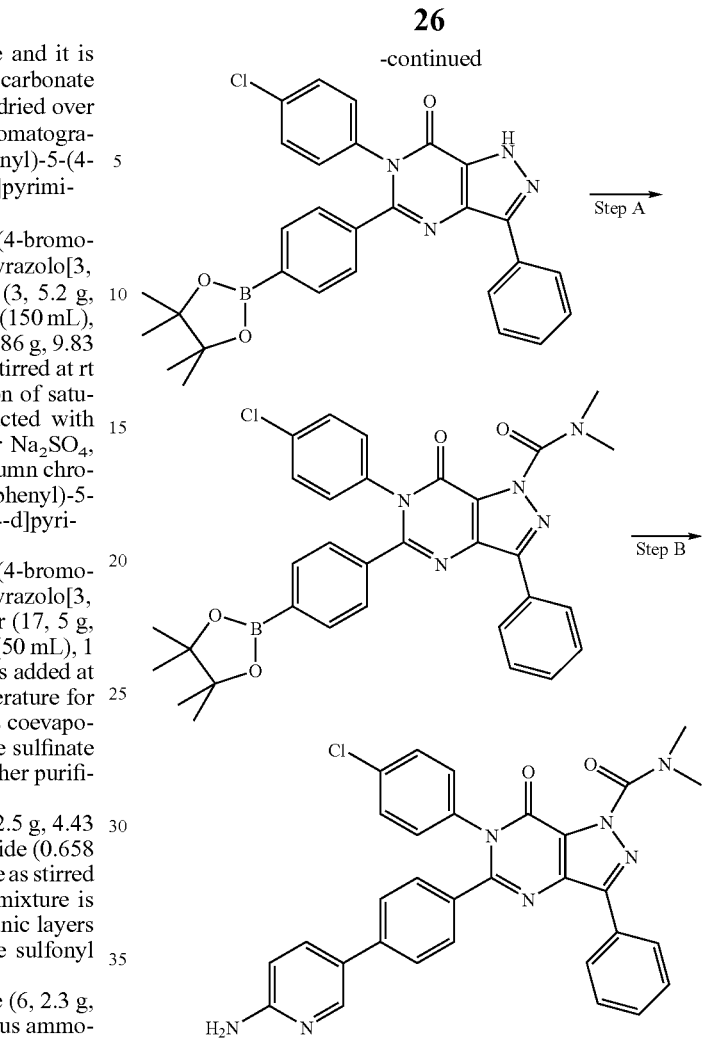

6-(4-Chloro-phenyl)-3-phenyl-5-[4-(4,4,5,5-tetramethyl-[1,3,2]dioxaborolan-2-yl)-phenyl]-1,6-dihydro-pyrazolo[4,3-d]pyrimidin-7-one is prepared as described in Example 2 (Steps B and D), using 4-amino-5-phenyl-2H-pyrazole-3-carboxylic acid ethyl ester (Rochais, C; Lisowski, V.; Dellemagne, P.; Rault, S. *Tetrahedron Letters* 2004, 45, 6353.) instead of 5-amino-3-methylsulfanyl-1-phenyl-1H-pyrazole-4-carboxylic acid ethyl ester; HPLC-MS calculated for C$_{29}$H$_{26}$BClN$_4$O$_3$ (M+H$^+$) 525.2, found 525.2.

Step A: To a solution of 6-(4-chloro-phenyl)-3-phenyl-5-[4-(4,4,5,5-tetramethyl-[1,3,2]dioxaborolan-2-yl)-phenyl]-1,6-dihydro-pyrazolo[4,3-d]pyrimidin-7-one (100.0 mg, 0.191 mmol) in anhydrous pyridine (1.0 mL) is added dimethylcarbamyl chloride (87.4 μL, 0.953 mmol). The reaction mixture is heated at 80° C. overnight before removal of the solvent. The residue is taken in water (10 mL) and extracted with EtOAc (3×10 mL). The combined organic layer is washed with brine, concentrated, and purified by silica gel chromatography to provide 6-(4-chloro-phenyl)-7-oxo-3-phenyl-5-[4-(4,4,5,5-tetramethyl-[1,3,2]dioxaborolan-2-yl)-phenyl]-6,7-dihydro-pyrazolo[4,3-d]pyrimidine-1-carboxylic acid dimethylamide as a white solid product; HPLC-MS calculated for C$_{32}$H$_{31}$BClN$_5$O$_4$ (M+H$^+$) 596.2, found 596.2.

Step B: Following the procedure as described in Example 2 (Step E), 5-[4-(6-amino-pyridin-3-yl)-phenyl]-6-(4-chloro-phenyl)-7-oxo-3-phenyl-6,7-dihydro-pyrazolo[4,3-d]pyrimidine-1-carboxylic acid dimethylamide is prepared as a white solid product; $^1$H NMR (CDCl$_3$, 400 MHz) δ 8.43 (d, 2H), 8.17 (d, 1H), 7.78 (dd, 1H), 7.51-7.38 (m, 7H), 7.33 (d, 2H), 7.16 (d, 2H), 6.72 (d, 1H), 5.58 (br, 2H), 3.25 (s, 3H), 3.14 (s, 3H); HPLC-MS calculated for C$_{31}$H$_{24}$ClN$_7$O$_2$ (M+H$^+$) 562.2, found 562.2.

Example 10

6-[4-(6-amino-pyridin-3-yl)-phenyl]-5-(4-chloro-phenyl)-3-methanesulfinyl-1-phenyl-1,5-dihydro-pyrazolo[3,4-d]pyrimidin-4-one

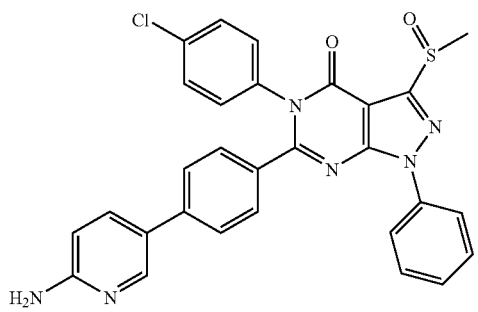 [SMILES: CS(=O)c1nn(-c2ccccc2)c2nc(-c3ccc(-c4ccc(N)nc4)cc3)n(-c3ccc(Cl)cc3)c(=O)c12]

The title compound is prepared as described in Example 2 (except only 1.25 equivalents of mCPBA is used in Step C) as a light yellow solid product; $^1$H NMR (CDCl$_3$, 400 MHz) δ 8.28 (s, 1H), 8.16 (d, 2H), 7.64 (d, 1H), 7.52 (t, 2H), 7.41-7.34 (m, 7H), 7.15 (d, 2H), 6.58 (d, 1H), 4.68 (br, 2H), 3.25 (s, 3H); HPLC-MS calculated for C$_{29}$H$_{21}$ClN$_6$O$_2$S (M+H$^+$) 553.1, found 553.1.

Example 12

3-[6-(4-Bromo-phenyl)-5-(4-chloro-phenyl)-4-oxo-4,5-dihydro-pyrazolo[3,4-d]pyrimidin-1-yl]-benza-mide

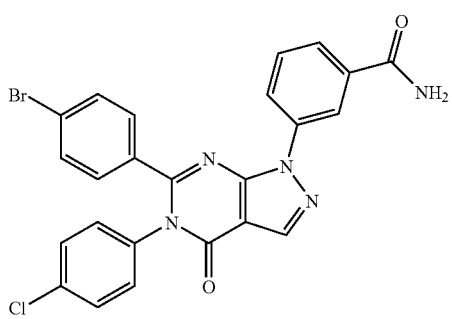 [SMILES: NC(=O)c1cccc(-n2ncc3c(=O)n(-c4ccc(Cl)cc4)c(-c4ccc(Br)cc4)nc32)c1]

3-[6-(4-Bromo-phenyl)-5-(4-chloro-phenyl)-4-oxo-4,5-dihydro-pyrazolo[3,4-d]pyrimidin-1-yl]-benzoic acid (60 mg, 0.11 mmol) is treated with SOCl$_2$ (1 mL) at 60° C. for 2 hours and then cooled down to room temperature. Excess of SOCl$_2$ is removed under vacuum and the residue is dissolved in anhydrous CH$_2$Cl$_2$ (1 mL) and dropped into a vigorously stirred solution of NH$_4$OH (5 mL). The resulted mixture is concentrated and purified by LC/MS to provide the title compound. HPLC-MS calculated C$_{24}$H$_{15}$BrClN$_5$O$_2$ (M+H$^+$): 520.0, found: 520.0.

Example 13

3-[6-[4-(6-Amino-pyridin-3-yl)-phenyl]-5-(4-chloro-phenyl)-4-oxo-4,5-dihydro-pyrazolo[3,4-d]pyrimi-din-1-yl]-benzamide

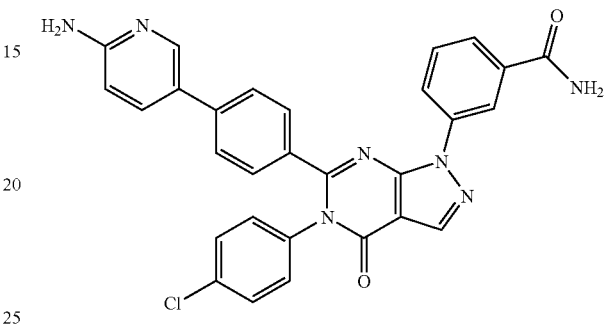

3-[6-[4-(6-Amino-pyridin-3-yl)-phenyl]-5-(4-chloro-phenyl)-4-oxo-4,5-dihydro-pyrazolo[3,4-d]pyrimidin-1-yl]-benzamide can be synthesized from 3-[6-(4-Bromo-phenyl)-5-(4-chloro-phenyl)-4-oxo-4,5-dihydro-pyrazolo[3,4-d]pyrimidin-1-yl]-benzamide by following the method described in example 2 step D and step E. HPLC-MS calculated C$_{29}$H$_{20}$ClN$_7$O$_2$ (M+H$^+$): 534.1, found: 534.1

Example 14

6-[4-(6-amino-pyridin-3-yl)-phenyl]-5-(4-chloro-phenyl)-1-(3-methanesulfonyl-phenyl)-1,5-dihydro-pyrazolo[3,4-d]pyrimidin-4-one

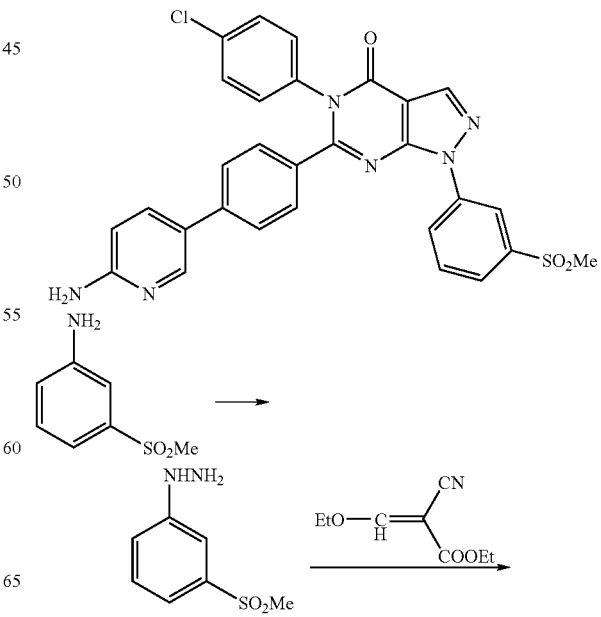

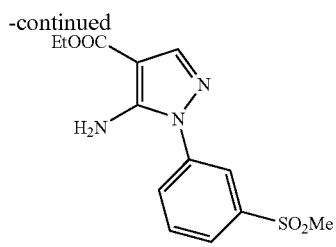

To a suspension of 3-methylsulfonyl-analine hydrochloride (1.00 g, 4.82 mmol) in concentrated HCl (3.2 mL) is added a solution of NaNO$_2$ (0.39 g, 5.65 mmol) in water (1.6 mL) at 0° C. The reaction mixture is stirred at 0° C. for 30 min before a solution of SnCl$_2$·2H$_2$O (2.72 g, 12.1 mmol) in concentrated HCl (3.2 mL) and water (0.8 mL) is added. The reaction mixture is stirred at 0° C. for another hour before slowly basified with 12N NaOH aqueous solution, followed by extraction with EtOAc. The combined organic layer is washed with brine, dried over MgSO$_4$, and evaporated in vacuo to provide crude (3-methanesulfonyl-phenyl)-hydrazine.

A solution of the above crude (3-methanesulfonyl-phenyl)-hydrazine (0.86 g, 4.6 mmol) and ethyl (ethoxymethylene) cyanoacetate (0.78 g, 4.6 mmol) in EtOH (23 mL) is heated at 80° C. for 2 h before removal of the solvent. The residue is purified by silica gel chromatography to provide 5-amino-1-(3-methanesulfonyl-phenyl)-1H-pyrazole-4-carboxylic acid ethyl ester as a light yellow solid; HPLC-MS calculated for C$_{13}$H$_{15}$N$_3$O$_4$S (M+H$^+$) 310.1, found 310.1.

6-[4-(6-Amino-pyridin-3-yl)-phenyl]-5-(4-chloro-phenyl)-1-(3-methanesulfonyl-phenyl)-1,5-dihydro-pyrazolo[3,4-d]pyrimidin-4-one is prepared as described in Example 2 (Steps B, D and E), using 5-amino-1-(3-methanesulfonyl-phenyl)-1H-pyrazole-4-carboxylic acid ethyl ester instead of 5-amino-3-methylsulfanyl-1-phenyl-1H-pyrazole-4-carboxylic acid ethyl ester; $^1$H NMR (CDCl$_3$, 400 MHz) δ 8.95 (s, 1H), 8.53 (d, 1H), 8.37 (s, 1H), 7.99 (m, 2H), 7.92 (d, 1H), 7.73 (t, 1H), 7.50 (d, 2H), 7.37 (m, 4H), 7.13 (d, 2H), 6.95 (d, 1H), 3.12 (s, 3H); HPLC-MS calculated for C$_{29}$H$_{21}$ClN$_6$O$_3$S (M+H$^+$) 569.1, found 569.1.

Example 15

6-(4-Chloro-phenyl)-3-(3-methanesulfonyl-phenyl)-5-(4-pyrazin-2-yl-phenyl)-3,6-dihydro-[1,2,3]triazolo[4,5-d]pyrimidin-7-one

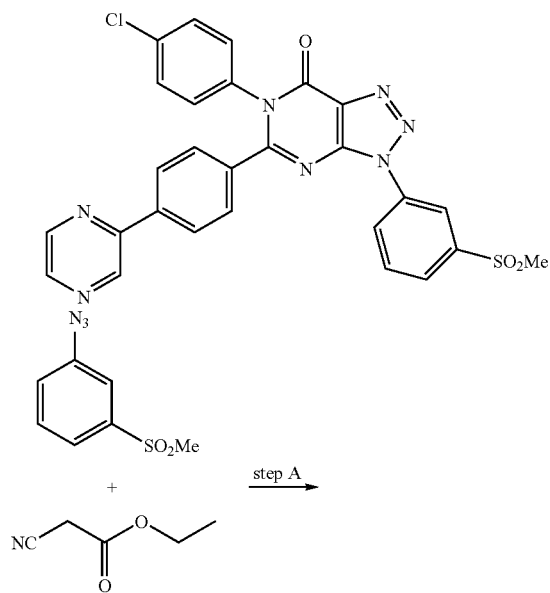

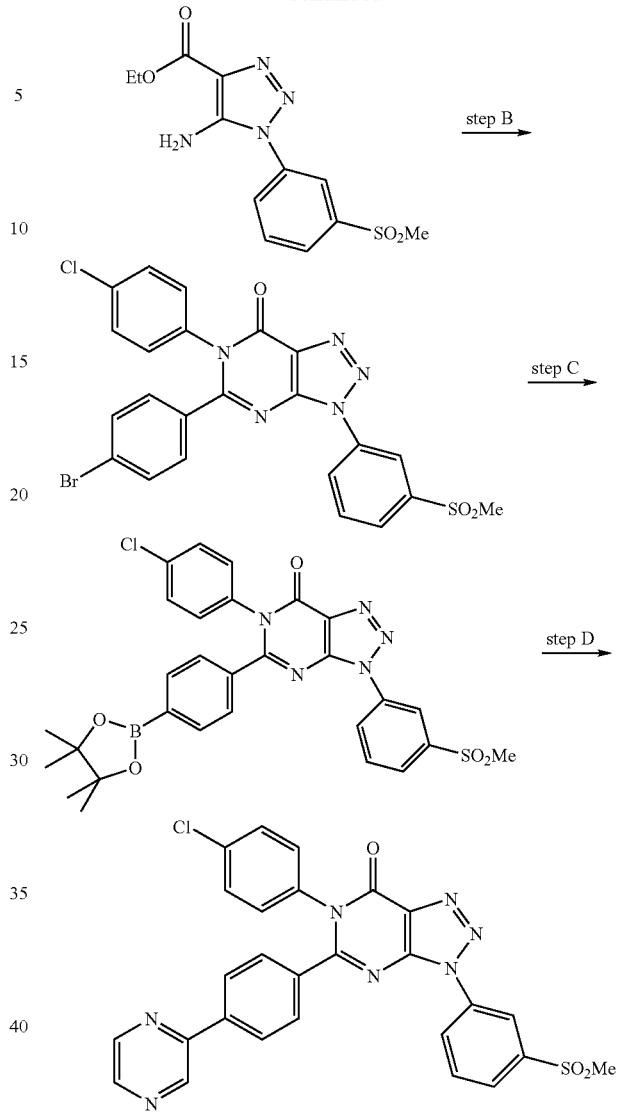

Step A: To a freshly prepared NaOEt (3.57 mmol) solution in EtOH (2 mL) is added ethyl cyanoacetate (444 mg, 3.93 mmol) at 0° C. After stirring at 0° C. for 10 min., azidobenzene (541 mg in 3 mL EtOH, 2.75 mmol, prepared according to the method reported by M. Kurumi et al. *Heterocycles.* 2000, 53, 2809) is added. After the addition, the mixture is allowed to slowly warm up to room temperature and stirred for 14 h. The mixture is then treated with water (30 mL) and extracted with EtOAc (3×30 mL). The combined extracts is concentrated and purified by flash column chromatography (silica gel, 0%-5% MeOH/CH$_2$Cl$_2$) to provide 5-amino-1-(3-methanesulfonyl-phenyl)-1H-[1,2,3]triazole-4-carboxylic acid ethyl ester as a white solid. HPLC-MS calculated C$_{12}$H$_{14}$N$_4$O$_4$S (M+H$^+$): 311.1, found: 311.1.

Step B: A mixture of 5-amino-1-(3-methanesulfonyl-phenyl)-1H-[1,2,3]triazole-4-carboxylic acid ethyl ester (310 mg, 1 mmol), 4-bromo-N-(4-chloro-phenyl)-benzimidoyl chloride (1.2 mmol) and TiCl$_4$ (2 mmol) in anhydrous dichloroethane (5 mL) is heated to 150° C. for 14 h. After cooling down to room temperature, the mixture is diluted with CH$_2$Cl$_2$ (20 mL) and treated with water (30 mL). The solid is collected by filtration and washed with MeOH (5 ml) to provide the crude 5-(4-bromo-phenyl)-6-(4-chloro-phenyl)-

3-(3-methanesulfonyl-phenyl)-3,6-dihydro-[1,2,3]triazolo[4,5-d]pyrimidin-7-one as yellow solid which is used for next step without further purification.

Step C: To a solution of crude 5-(4-bromo-phenyl)-6-(4-chloro-phenyl)-3-(3-methanesulfonyl-phenyl)-3,6-dihydro-[1,2,3]triazolo[4,5-d]pyrimidin-7-one (120 mg, 0.216 mmol) in DMF (1.5 mL) is added bis(pinacolato)diboron (76 mg, 0.30 mmol), Pd(dppf)$_2$Cl$_2$ (17.6 mg, 0.02 mmol) and KOAc (64 mg, 0.65 mmol). The reaction mixture is degassed and heated at 80° C. under N$_2$ for 1 hour. After cooling down of the reaction mixture, it is poured into water (15 mL) and extracted with EtOAc (3×10 mL). The organic layers are combined and washed with brine (20 mL) and dried (MgSO$_4$). After removal of the drying agent and solvent, the residue is purified by flash column chromatography (silica gel, 0%~60% EtOAc/hexane) to provide the desired product 6-(4-chloro-phenyl)-3-(3-methanesulfonyl-phenyl)-5-[4-(4,4,5,5-tetramethyl-[1,3,2]dioxaborolan-2-yl)-phenyl]-3,6-dihydro-[1,2,3]triazolo[4,5-d]pyrimidin-7-one as brown solid.

Step D: A reaction tube is charged with 6-(4-chloro-phenyl)-3-(3-methanesulfonyl-phenyl)-5-[4-(4,4,5,5-tetramethyl-[1,3,2]dioxaborolan-2-yl)-phenyl]-3,6-dihydro-[1,2,3]triazolo[4,5-d]pyrimidin-7-one (32 mg, 0.053 mmol), 2-chloropyrizine (12.1 mg, 0.106 mmol), Cs$_2$CO$_3$ (34.5 mg, 0.106 mmol), Pd$_2$(dba)$_3$ (5.5 mg, 0.005 mmol), 1,3-bis-(2,6-diisopropyl-phenyl)-3H-imidazol-1-ium chloride (4.7 mg, 0.011 mmol) and anhydrous 1,4-dioxane (0.5 mL). The mixture is thoroughly degassed by alternately connecting the flask to vacuum and N$_2$ for three times. The dark red reaction mixture is then heated at 90° C. for 16 h. The reaction mixture is then cooled down to room temperature and treated with H$_2$O (10 mL). EtOAc is used for the extraction (3×3 mL). The combined extracts are concentrated under vacuum and purified by preparative LC/MS to provide the title compound. $^1$H NMR (CDCl$_3$) δ (ppm) 9.03 (s, 1H), 8.93 (s, 1H), 8.66 (s, 1H), 8.55-8.60 (m, 2H), 8.07 (d, 1H), 7.99 (d, 2H), 7.83 (t, 1H), 7.52 (d, 2H), 7.37 (d, 2H), 7.16 (d, 2H), 3.14 (s, 1H). HPLC-MS calculated C$_{27}$H$_{17}$ClN$_6$O (M+H$^+$): 477.1, found: 477.1. HPLC-MS calculated C$_{27}$H$_{18}$ClN$_7$O$_3$S (M+H$^+$): 556.1, found: 556.1

Example 16

5-[4-(6-amino-pyridin-3-yl)-phenyl]-6-(4-chloro-phenyl)-3-(3-methanesulfonyl-phenyl)-3,6-dihydro-[1,2,3]triazolo[4,5-d]pyrimidin-7-one

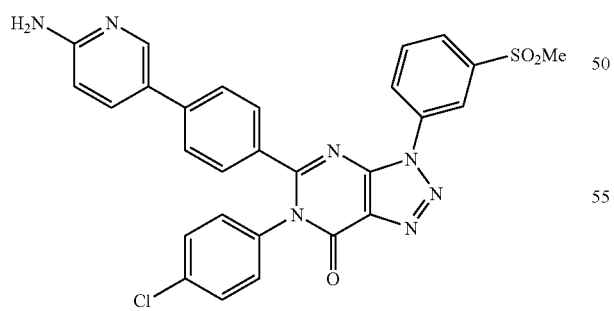

5-[4-(6-Amino-pyridin-3-yl)-phenyl]-6-(4-chloro-phenyl)-3-(3-methanesulfonyl-phenyl)-3,6-dihydro-[1,2,3]triazolo[4,5-d]pyrimidin-7-one can be prepared from 6-(4-chloro-phenyl)-3-(3-methanesulfonyl-phenyl)-5-[4-(4,4,5,5-tetramethyl-[1,3,2]dioxaborolan-2-yl)-phenyl]-3,6-dihydro-[1,2,3]triazolo[4,5-d]pyrimidin-7-one by following the method described in example 2 step E. $^1$H NMR (CDCl$_3$) δ (ppm) 8.89 (s, 1H), 8.59 (d, 1H), 8.25 (d, 1H), 8.10-8015 (m, 2H), 7.92 (t, 1H), 7.58-7.64 (m, 4H), 7.34-7.42 (m, 4H), 7.10 (d, 1H), 3.22 (s, 1H). HPLC-MS calculated C$_{28}$H$_{20}$ClN$_7$O$_3$S (M+H$^+$): 570.1, found: 570.1.

Example 19

6-[4-(5-Amino-pyridin-2-yl)-phenyl]-5-(4-chloro-phenyl)-1-(3-methanesulfonyl-phenyl)-1,5-dihydro-pyrazolo[3,4-d]pyrimidin-4-one

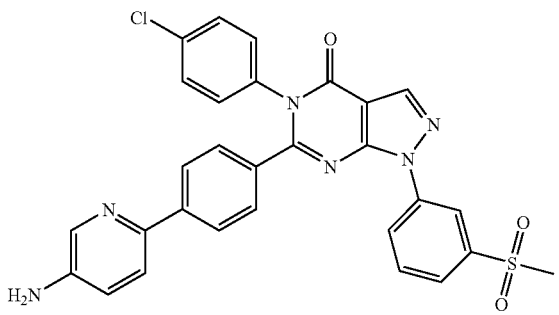 [SMILES: CS(=O)(=O)c1cccc(-n2ncc3c(=O)n(-c4ccc(Cl)cc4)c(-c4ccc(-c5ccc(N)cn5)cc4)nc32)c1]

A solution of 5-(4-chloro-phenyl)-1-(3-methanesulfonyl-phenyl)-6-[4-(4,4,5,5-tetramethyl-[1,3,2]dioxaborolan-2-yl)-phenyl]-1,5-dihydro-pyrazolo[3,4-d]-pyrimidin-4-one (prepared as described in example 51, 0.60 g, 1.0 mmol) in N,N-dimethylformamide (20 mL) is degassed with argon for 0.5 h. Then 5-amino-2-bromopyridine (0.26 g, 1.5 mmol), cesium carbonate (0.648 g, 1.99 mmol), Pd(dppf)$_2$Cl$_2$ (0.073 g, 0.099 mmol is added and the resulted mixture is degassed with argon for 0.5 h. The reaction mixture is then heated at 100° C. for 12 h. The reaction mixture is cooled to rt and diluted with water and extracted with ethyl acetate (3×). The combined organic layer is washed with brine, dried over Na$_2$SO$_4$, concentrated, and purified by preparative HPLC to afford 6-[4-(5-amino-pyridin-2-yl)-phenyl]-5-(4-chloro-phenyl)-1-(3-methane-sulfonyl-phenyl)-1,5-dihydro-pyrazolo[3,4-d]pyrimidin-4-one. $^1$H NMR (CD$_3$OD, 400 MHz) δ 8.94 (m, 1H), 8.60 (m, 1H), 8.41 (s, 1H), 7.95-7.99 (m, 3H), 7.82 (t, 1H), 7.68-7.75 (m, 5H), 7.34-7.39 (m, 4H), 3.19 (s, 3H); LC-MS calculated for C$_{29}$H$_{21}$ClN$_6$O$_3$S (M+H$^+$) 569.1, found 569.0.

Example 20

6-[4-(5-Amino-pyrazin-2-yl)-phenyl]-5-(4-chloro-phenyl)-1-(3-methanesulfonyl-phenyl)-1,5-dihydro-pyrazolo[3,4-d]pyrimidin-4-one

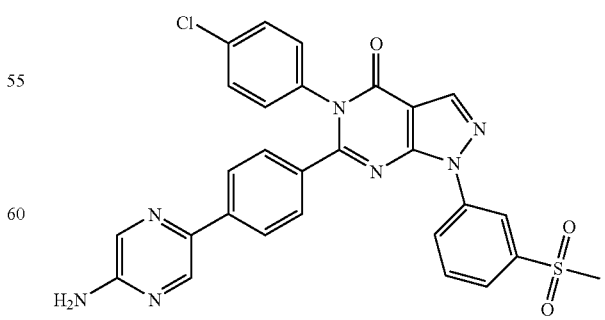

A solution of 5-(4-chloro-phenyl)-1-(3-methanesulfonyl-phenyl)-6-[4-(4,4,5,5-tetramethyl-[1,3,2]dioxaborolan-2- yl)-phenyl]-1,5-dihydro-pyrazolo[3,4-d]-pyrimidin-4-one (prepared as described in example 51, 0.50 g, 0.83 mmol) in N,N-dimethylformamide (20 mL) is degassed with argon for 0.5 h. Then 2-amino-5-bromopyrazine (0.216 g, 1.24 mmol), cesium carbonate (0.540 g, 1.66 mmol), Pd(dppf)$_2$Cl$_2$ (0.060 g, 0.082 mmol)) is added and the resulted mixture is degassed with argon for 0.5 h. The reaction mixture is then heated at 100° C. for 24 h. The reaction mixture is cooled to rt and diluted with water and extracted with ethyl acetate (3×). The combined organic layer is washed with brine, dried over Na$_2$SO$_4$, concentrated, and purified by column chromatography over silica gel (60-120 mesh) to afford 6-[4-(5-amino-pyrazin-2-yl)-phenyl]-5-(4-chloro-phenyl)-1-(3-methanesulfonyl-phenyl)-1,5-dihydro-pyrazolo[3,4-d]pyrimidin-4-one. $^1$H NMR (CDCl$_3$, 400 MHz) δ 8.93 (s, 1H), 8.60 (m, 1H), 8.42 (s, 1H), 8.37 (s, 1H), 8.12 (s, 1H), 7.93 (d, 1H), 7.82 (d, 2H), 7.73 (m, 1H), 7.47 (d, 2H), 7.36 (d, 2H), 7.15 (d, 2H), 5.05 (br, 2H), 3.13 (s, 3H), 3.01 (s, 3H); LC-MS calculated for C$_{28}$H$_{20}$ClN$_7$O$_3$S 570.1 (M+H$^+$), found 570.1.

Example 22

6-[4-(2-Amino-pyrimidin-5-yl)-phenyl]-5-(4-chloro-phenyl)-1-(3-methanesulfonyl-phenyl)-1,5-dihydro-pyrazolo[3,4-d]pyrimidin-4-one

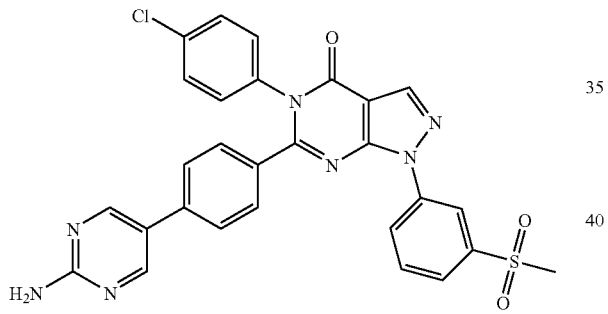

A solution of 5-(4-chloro-phenyl)-1-(3-methanesulfonyl-phenyl)-6-[4-(4,4,5,5-tetramethyl-[1,3,2]dioxaborolan-2-yl)-phenyl]-1,5-dihydro-pyrazolo[3,4-d]-pyrimidin-4-one (prepared as described in example 51, 0.90 g, 1.5 mmol) in N,N-dimethylformamide (25 mL) is degassed with argon for 0.5 h. Then 2-amino-5-bromopyrimidine (0.388 g, 2.23 mmol), cesium carbonate (0.97 g, 2.98 mmol), Pd(dppf)$_2$Cl$_2$ (0.109 g, 0.149 mmol) is added and the resulted mixture is degassed with argon for 0.5 h. The reaction mixture is then heated at 100° C. for 4 h. The reaction mixture is cooled to rt and diluted with water and extracted with ethyl acetate (3×). The combined organic layer is washed with brine, dried over Na$_2$SO$_4$, concentrated, and purified by column chromatography over silica gel (60-120 mesh) to afford 6-[4-(2-amino-pyrimidin-5-yl)-phenyl]-5-(4-chloro-phenyl)-1-(3-methanesulfonyl-phenyl)-1,5-dihydro-pyrazolo[3,4-d]pyrimidin-4-one (T-468). $^1$H NMR (CDCl$_3$, 400 MHz) δ 8.95 (s, 1H), 8.57 (br, 3H), 8.37 (s, 1H), 7.93 (d, 1H), 7.74 (m, 1H), 7.37-7.51 m, 6H), 7.16 (d, 2H), 5.31 (br, 2H), 3.13 (s, 3H); LC-MS calculated for C$_{28}$H$_{20}$ClN$_7$O$_3$S (M+H$^+$) 570.1, found 570.1.

Example 23

3-[5-(4-Chloro-phenyl)-4-oxo-6-(4-pyrazin-2-yl-phenyl)-4,5-dihydro-pyrazolo[3,4-d]pyrimidin-1-yl]-benzamide

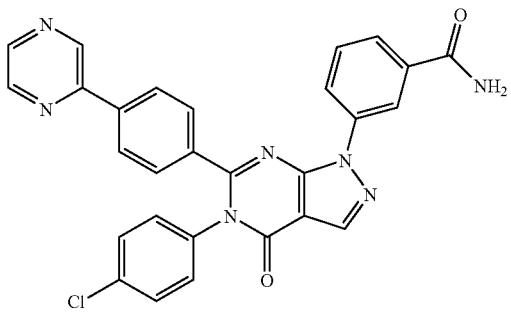 [SMILES: NC(=O)c1cccc(-n2ncc3c(=O)n(-c4ccc(Cl)cc4)c(-c4ccc(-c5cnccn5)cc4)nc32)c1]

3-[5-(4-Chloro-phenyl)-4-oxo-6-(4-pyrazin-2-yl-phenyl)-4,5-dihydro-pyrazolo[3,4-d]pyrimidin-1-yl]-benzamide can be synthesized from 3-[6-(4-bromo-phenyl)-5-(4-chloro-phenyl)-4-oxo-4,5-dihydro-pyrazolo[3,4-d]pyrimidin-1-yl]-benzamide (example 12) by following the method described in example 15 step C and step D. HPLC-MS calculated C$_{28}$H$_{18}$ClN$_7$O$_2$ (M+H$^+$): 520.1, found: 520.1.

Example 24

N-{3-[2-[4-(6-Amino-pyridin-3-yl)-phenyl]-1-(4-chloro-phenyl)-6-oxo-1,6-dihydro-purin-9-yl]-phenyl}-methane sulfonamide A solution of N-(3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-phenyl)-methane sulfonamide (prepared as described in example 26, 0.700 g, 1.13 mmol) in N,N-dimethylformamide (15 mL) is degassed with argon for 0.5 h. Then 2-amino-5-bromopyridine (0.290 g, 1.69 mmol), cesium carbonate (0.740 g, 2.26 mmol), Pd(dppf)$_2$Cl$_2$ (0.040 g, 0.056 mmol) is added and the resulted mixture is degassed with argon for 0.5 h. The reaction mixture is then heated at 100° C. for 3 h. The reaction mixture is cooled to rt and diluted with water and extracted with ethyl acetate (3×). The combined organic layer is washed with brine, dried over Na$_2$SO$_4$, concentrated, and purified by preparative HPLC to afford N-{3-[2-[4-(6-amino-pyridin-3-yl)-phenyl]-1-(4-chloro-phenyl)-6-oxo-1,6-dihydro-purin-9-yl]-phenyl}-methane sulfonamide, as a yellow solid. $^1$H NMR (CD$_3$OD, 400 MHz) δ 8.51 (s, 1H), 8.22 (m, 1H), 8.12 (d, 1H), 7.93 (d, 1H), 7.55

(m, 6H), 7.37 (m, 2H), 7.34 (m, 2H), 7.32 (d, 1H), 7.10 (d, 1H), 3.0 (s, 3H); LC-MS calculated for $C_{29}H_{22}ClN_7O_3S$ (M+H$^+$) 584.1, found 583.9.

Example 25

3-[2-[4-(6-Amino-pyridin-3-yl)-phenyl]-1-(4-chloro-phenyl)-6-oxo-1,6-dihydro-purin-9-yl]-benzene sulfonamide

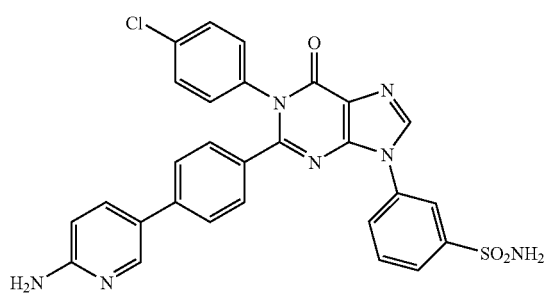 [SMILES: Nc1ccc(-c2ccc(-c3nc4c(ncn4-c4cccc(S(N)(=O)=O)c4)c(=O)n3-c3ccc(Cl)cc3)cc2)cn1]

3-[6-(4-bromo-phenyl)-5-(4-chloro-phenyl)-4-oxo-4,5-dihydro-pyrazolo[3,4-d]pyrimidin-1-yl]-benzene sulfonamide (prepared as described in example 31, used without purification, 2.00 g, 3.59 mmol) in N,N-dimethylformamide (60 mL) is taken in the round bottomed flask and is degassed with argon for 0.5 h. To the resulting mixture is added bis(pinacolato)diboron (1.09 g, 4.31 mmol), Pd(dppf)$_2$Cl$_2$ (0.29 g, 0.36 mmol), potassium acetate (1.00 g, 10.77 mmol) and the resulted mixture is degassed with argon for 0.5 h. The reaction mixture is then heated at 80° C. for 2 h. The reaction mixture is cooled to rt and diluted with water and the compound is extracted with ethyl acetate (3×). The combined organic layer is washed with brine, dried over Na$_2$SO$_4$, concentrated, and purified by column chromatography to provide 3-{5-(4-chloro-phenyl)-4-oxo-6-[4-(4,4,5,5-tetramethyl-[1,3,2]dioxaborolan-2-yl)-phenyl]-4,5-dihydro-pyrazolo[3,4-d]pyrimidin-1-yl}-benzene sulfonamide.

A solution of 3-{5-(4-chloro-phenyl)-4-oxo-6-[4-(4,4,5,5-tetramethyl-[1,3,2]dioxaborolan-2-yl)-phenyl]-4,5-dihydro-pyrazolo[3,4-d]pyrimidin-1-yl}-benzene sulfonamide (0.300 g, 0.496 mmol) in N,N-dimethylformamide (25 mL) is degassed with argon for 0.5 h. Then 2-amino-5-bromopyridine (0.128 g, 0.745 mmol), cesium carbonate (0.323 g, 0.993 mmol), Pd(dppf)$_2$Cl$_2$ (0.036 g, 0.049 mmol) is added and the resulted mixture is degassed with argon for 0.5 h. The reaction mixture is then heated at 100° C. for 4 h. The reaction mixture is cooled to rt and diluted with water and extracted with ethyl acetate (3×). The combined organic layer is washed with brine, dried over Na$_2$SO$_4$, concentrated, and purified by preparative HPLC to afford 3-[2-[4-(6-amino-pyridin-3-yl)-phenyl]-1-(4-chloro-phenyl)-6-oxo-1,6-dihydro-purin-9-yl]-benzene sulfonamide. $^1$H NMR (DMSO-d$_6$, 400 MHz) δ 8.66 (s, 1H), 8.23 (s, 1H), 8.07 (m, 1H), 7.94 (m, 1H), 7.83 (m, 1H), 7.67 (m, 1H), 7.58 (m, 2H), 7.35-7.48 (m, 10H), 6.47 (d, 1H), 6.15 (br, 1H); LC-MS calculated for $C_{28}H_{20}ClN_7O_3S$ (M+H$^+$) 570.1, found 570.2.

Example 26

N-{3-[2-[4-(5-Amino-pyridin-2-yl)-phenyl]-1-(4-chloro-phenyl)-6-oxo-1,6-dihydro-purin-9-yl]-phenyl}-methane sulfonamide

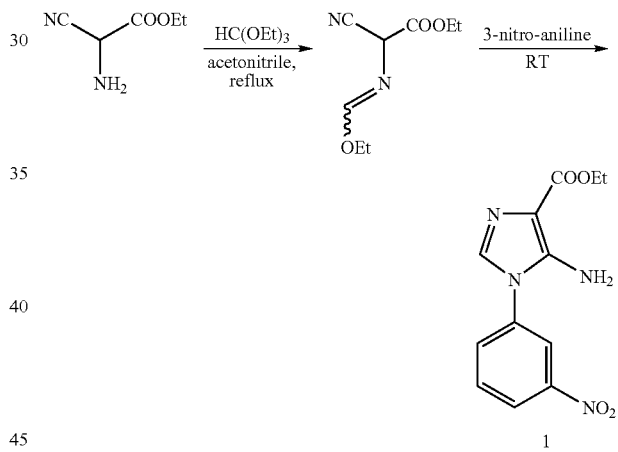

Preparation of 5-amino-1-(3-nitro-phenyl)-1H-imidazole-4-carboxylic acid ethyl ester A solution of amino-cyano-acetic acid ethyl ester (17.06 g, 133.3 mmol) and triethyl orthoformate (19.7 g, 133.3 mmol) in acetonitrile (175 mL) is heated at reflux for 45 min. The reaction mixture is allowed to reach rt and 3-nitro aniline (18.4 g, 133.3 mmol) is added and stirred at rt for 12 h. The crude product obtained is purified by column chromatography to afford the product as pale yellow solid (1).

Preparation of 2-(4-bromo-phenyl)-1-(4-chloro-phenyl)-9-(3-nitro-phenyl)-1,9-dihydro-purin-6-one

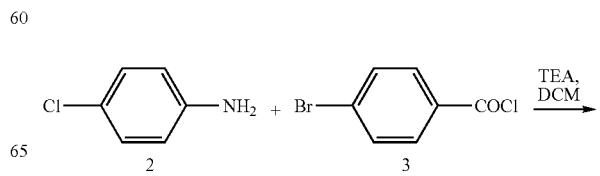

37

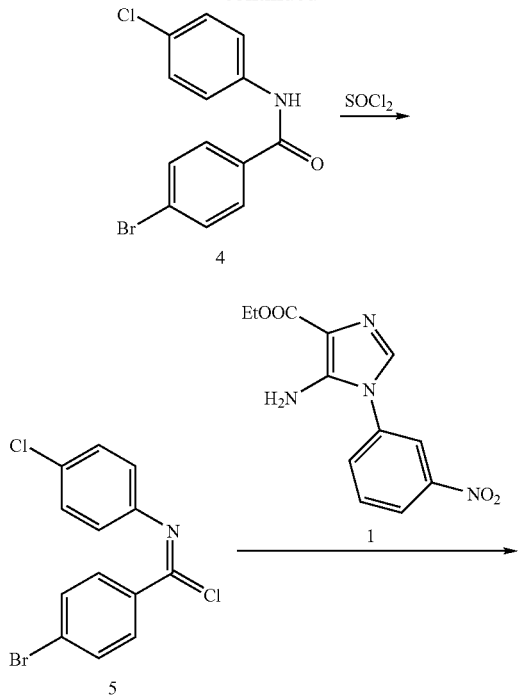

4-Bromo-N-(4-chloro-phenyl)-benzamide (4) used is prepared by the following procedure. To a solution of 4-chloroaniline (2, 66.0 g, 517.4 mmol) and 4-bromobenzoyl chloride (3, 109.0 g, 497.5 mmol) in dichloromethane (1200 mL) is added triethyl amine (83.2 mL, 597.0 mmol). The reaction mixture is then poured into 0.05 N sodium hydroxide solution and the resulted suspension is stirred at rt for 1 h. The solid formed is filtered and washed well with water. It is dried in vacuo and used for the next step.

4-Bromo-N-(4-chloro-phenyl)-benzimidoyl chloride is prepared by heating 4-bromo-N-(4-chloro-phenyl)-benzamide (13.39 g, 43.2 mmol) and thionyl chloride (100 mL) for 1 h. The clear solution is concentrated and the residue obtained is coevaporated with toluene (100 mL). A solution of 5-amino-1-(3-nitro-phenyl)-1H-imidazole-4-carboxylic acid ethyl ester (1, 4.00 g, 14.4 mmol) in dry chloroform (50 mL) is then added and the resulting mixture is concentrated to afford a dry residue. It is heated to 170° C. without solvent for 6 h. The crude product obtained is purified by column chromatography to afford the product as greenish black solid as product (6).

38

Preparation of N-(3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-phenyl)-methane sulfonamide

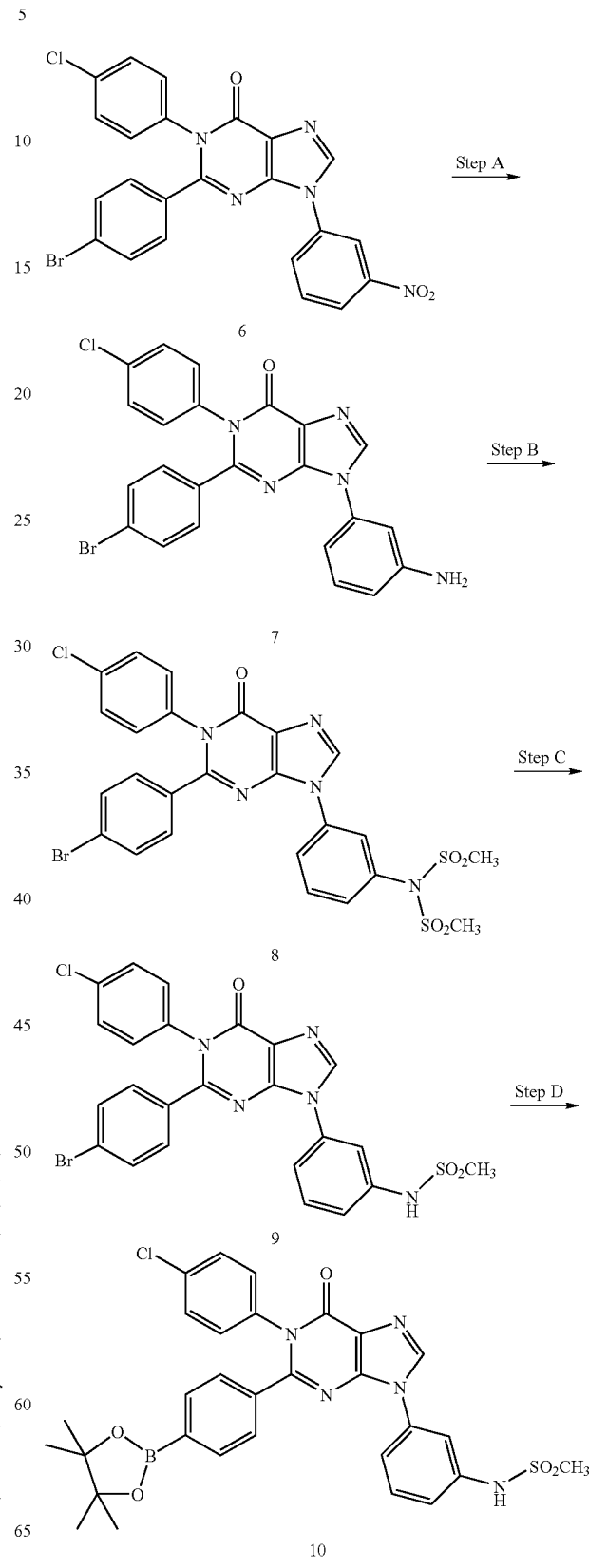

Step A: To a stirred solution of 2-(4-bromo-phenyl)-1-(4-chloro-phenyl)-9-(3-nitro-phenyl)-1,9-dihydro-purin-6-one (6, 4.5 g, 8.6 mmol) in ethanol (160 mL), iron powder (2.4 g, 43 mmol) and saturated solution of ammonium chloride (60 mL) is added and the reaction mixture is heated at 80° C. for 6 h. The reaction mixture is filtered through the celite. The celite bed is washed well with methanol and chloroform. The filtrate is concentrated to afford a residue. It is dissolved in ethyl acetate, washed with 10% sodium bicarbonate solution, water and brine, dried over $Na_2SO_4$, concentrated. The crude product is taken in diethyl ether (4×) and stirred for 20 min. to provide 9-(3-amino-phenyl)-2-(4-bromo-phenyl)-1-(4-chloro-phenyl)-1,9-dihydro-purin-6-one (7) as a brown solid.

Step B: To a stirred solution of 9-(3-amino-phenyl)-2-(4-bromo-phenyl)-1-(4-chloro-phenyl)-1,9-dihydro-purin-6-one (7, 3.8 g, 7.71 mmol) in dichloromethane (90 mL), methane sulphonyl chloride (1.76 g, 15.4 mmol) and triethyl amine (2.73 g, 26.9 mmol) are added at 0° C. and the resulting mixture is stirred at rt. After 2 h, water is added to the reaction mixture and extracted with chloroform (3×). The combined organic layer is washed with brine, dried over $Na_2SO_4$, concentrated to provide bis-methane sulphonamide of 9-(3-amino-phenyl)-2-(4-bromo-phenyl)-1-(4-chloro-phenyl)-1,9-dihydro-purin-6-one (8) as a pale brown solid.

Step C: To a stirred solution of bis-methane sulphonamide of 9-(3-amino-phenyl)-2-(4-bromo-phenyl)-1-(4-chloro-phenyl)-1,9-dihydro-purin-6-one (8, 5 g, 7.7 mmol) in tetrahydrofuran (75 mL), tetra-n-butyl ammonium fluoride (2.29 g, 8.47 mmol) is added and the resulting mixture is heated at reflux for 1 h. The reaction mixture is diluted with water and the compound is extracted with ethyl acetate (3×). The combined organic layer is washed with brine, dried over $Na_2SO_4$, concentrated, and purified by column chromatography to provide N-{3-[2-(4-bromo-phenyl)-1-(4-chloro-phenyl)-6-oxo-1,6-dihydro-purin-9-yl]-phenyl}-methane sulfonamide (9), as off-white solid.

Step D: N-{3-[2-(4-bromo-phenyl)-1-(4-chloro-phenyl)-6-oxo-1,6-dihydro-purin-9-yl]-phenyl}-methane sulfonamide (9, 10.8 g, 18.9 mmol) in N,N-dimethyl-formamide (120 mL) is taken in the round bottomed flask and is degassed with argon for 0.5 h. To the resulting mixture is added bis (pinacolato)-diboron (5.28 g, 20.8 mmol), $Pd(dppf)_2Cl_2$ (0.038 g, 1.89 mmol), potassium acetate (5.57 g, 56.8 mmol) and the mixture is degassed with argon for 0.5 h. The reaction mixture is then heated at 80° C. for 3 h. The reaction mixture is cooled to rt and diluted with water and the compound is extracted with ethyl acetate (3×). The combined organic layer is washed with brine, dried over $Na_2SO_4$, concentrated, and purified by column chromatography to provide N-(3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-phenyl)-methane sulfonamide (10) as off-white solid.

Preparation of N-{3-[2-[4-(5-amino-pyridin-2-yl)-phenyl]-1-(4-chloro-phenyl)-6-oxo-1,6-dihydro-purin-9-yl]-phenyl}-methane sulfonamide A solution of N-(3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-phenyl)-methane sulfonamide (10, 0.35 g, 0.57 mmol) in N,N-dimethylformamide (15 mL) is degassed with argon for 0.5 h. Then 5-amino-2-bromopyridine (0.147 g, 0.850 mmol), cesium carbonate (0.360 g, 1.13 mmol), $Pd(dppf)_2Cl_2$ (0.020 g, 0.028 mmol) is added and the resulted mixture is degassed with argon for 0.5 h. The reaction mixture is then heated at 100° C. for 12 h. The reaction mixture is cooled to rt and diluted with water and extracted with ethyl acetate (3×). The combined organic layer is washed with brine, dried over $Na_2SO_4$, concentrated, and purified by preparative HPLC to afford N-{3-[2-[4-(5-amino-pyridin-2-yl)-phenyl]-1-(4-chloro-phenyl)-6-oxo-1,6-dihydro-purin-9-yl]-phenyl}-methane sulfonamide, as a yellow solid. $^1$H NMR (CD$_3$OD, 400 MHz) δ 8.53 (s, 1H), 7.95 (m, 3H), 7.69 (d, 5H), 7.55 (m, 2H), 7.38 (m, 4H), 7.25 (m, 1H), 3.01 (s, 3H); LC-MS calculated for $C_{29}H_{22}ClN_7O_3S$ (M+H$^+$) 584.1, found 584.1.

Example 27

3-(6-(4-(5-aminopyridin-2-yl)phenyl)-5-(4-chlorophenyl)-4-oxo-4,5-dihydro-1H-pyrazolo[3,4-d]pyrimidin-1-yl)benzonitrile

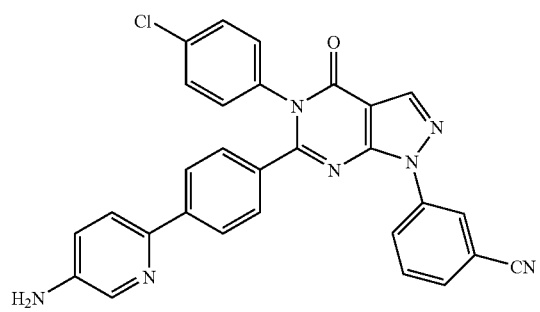 [SMILES: N#Cc1cccc(-n2ncc3c(=O)n(-c4ccc(Cl)cc4)c(-c4ccc(-c5ccc(N)cn5)cc4)nc32)c1]

A solution of 3-{5-(4-chloro-phenyl)-4-oxo-6-[4-(4,4,5,5-tetramethyl-[1,3,2]-dioxaborolan-2-yl)-phenyl]-4,5-dihydro-pyrazolo[3,4-d]pyrimidin-1-yl}-benzonitrile (prepared as described in example 40, 1.00 g, 1.81 mmol) in N,N-dimethylformamide (25 mL) is added and the resulted mixture is degassed with argon for 0.5 h. Then 5-amino-2-bromopyridine (0.472 g, 2.72 mmol), cesium carbonate (1.18 g, 3.62 mmol), $Pd(dppf)_2Cl_2$ (0.147 g, 0.181 mmol) and is degassed with argon for 0.5 h. The reaction mixture is then heated at 100° C. for 2 h. The reaction mixture is cooled to rt and diluted with water and extracted with ethyl acetate (3×). The combined organic layer is washed with brine, dried over $Na_2SO_4$, concentrated, and purified by preparative HPLC to afford 3-[6-[4-(5-amino-pyridin-2-yl)-phenyl]-5-(4-chloro-phenyl)-4-oxo-4,5-dihydro-pyrazolo[3,4-d]pyrimidin-1-yl]-benzonitrile. LC-MS calculated for $C_{29}H_{18}ClN_7O$ (M+H$^+$) 516.1, found 516.1.

Example 28

3-(6-(4-(6-aminopyridin-3-yl)phenyl)-5-(4-chlorophenyl)-4-oxo-4,5-dihydro-1H-pyrazolo[3,4-d]pyrimidin-1-yl)benzonitrile

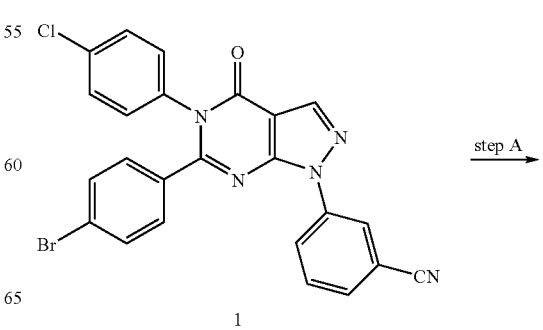

step A

1

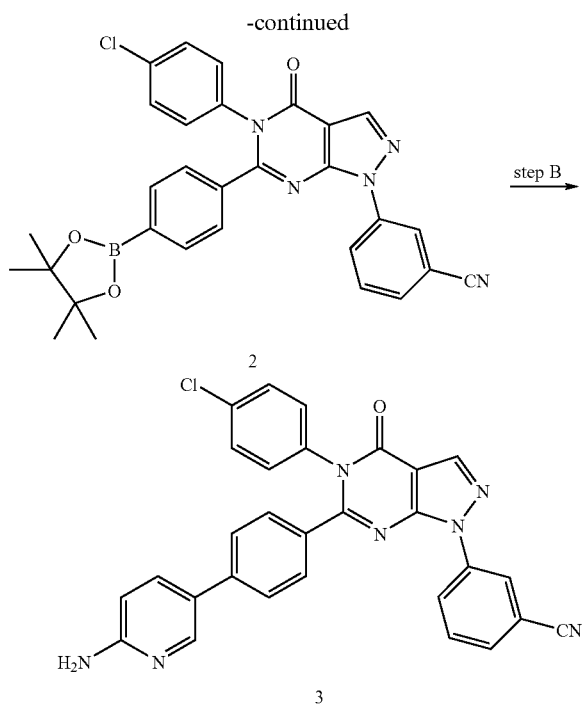

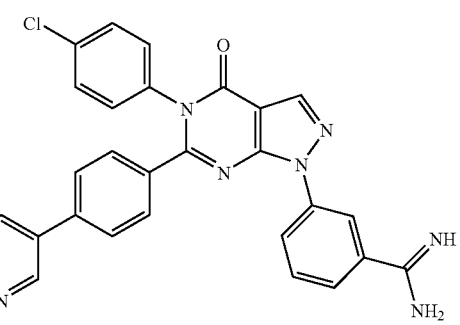

Step A: 3-[6-(4-bromo-phenyl)-5-(4-chloro-phenyl)-4-oxo-4,5-dihydro-pyrazolo[3,4-d]pyrimidin-1-yl]-benzonitrile (1, prepared as described in example 40, 11.0 g, 21.9 mmol) in N,N-dimethyl-formamide (200 mL) is taken in the round bottomed flask and is degassed with argon for 0.5 h. To the resulting mixture is added bis(pinacolato)diboron (6.66 g, 26.3 mmol), Pd(dppf)$_2$Cl$_2$ (1.6 g, 2.18 mmol), potassium acetate (6.43 g, 65.6 mmol) and the mixture is degassed with argon for 0.5 h. The reaction mixture is then heated at 80° C. for 3 h. The reaction mixture is cooled to rt and diluted with water and the compound is extracted with ethyl acetate (3×). The combined organic layer is washed with brine, dried over Na$_2$SO$_4$, concentrated, and purified by column chromatography to provide 3-{5-(4-chloro-phenyl)-4-oxo-6-[4-(4,4,5,5-tetramethyl-[1,3,2]dioxaborolan-2-yl)-phenyl]-4,5-dihydro-pyrazolo[3,4-d]pyrimidin-1-yl}-benzonitrile (2) as white solid.

Step B: A solution of 3-{5-(4-chloro-phenyl)-4-oxo-6-[4-(4,4,5,5-tetramethyl-[1,3,2]-dioxaborolan-2-yl)-phenyl]-4,5-dihydro-pyrazolo[3,4-d]pyrimidin-1-yl}-benzonitrile (2, 1.00 g, 1.81 mmol) in N,N-dimethylformamide (25 mL) is degassed with argon for 0.5 h. Then 2-amino-5-bromopyridine (0.47 g, 2.72 mmol), cesium carbonate (1.18 g, 3.62 mmol), Pd(dppf)$_2$Cl$_2$ (0.147 g, 0.181 mmol) is added and the resulted mixture is degassed with argon for 0.5 h. The reaction mixture is then heated at 100° C. for 2 h. The reaction mixture is cooled to rt and diluted with water and extracted with ethyl acetate (3×). The combined organic layer is washed with brine, dried over Na$_2$SO$_4$, concentrated, and purified by preparative HPLC to afford 3-[6-[4-(6-amino-pyridin-3-yl)-phenyl]-5-(4-chloro-phenyl)-4-oxo-4,5-dihydro-pyrazolo[3,4-d]pyrimidin-1-yl]-benzonitrile (3). LC-MS calculated for C$_{29}$H$_{18}$ClN$_7$O (M+H$^+$) 516.1, found 516.1.

Example 29

3-[6-[4-(6-Amino-pyridin-3-yl)-phenyl]-5-(4-chloro-phenyl)-4-oxo-4,5-dihydro-pyrazolo[3,4-d]pyrimidin-1-yl]-benzamidine

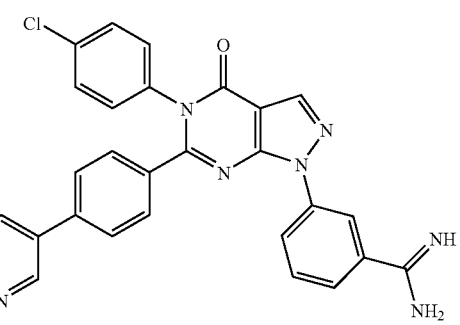

At 0° C., 3-[6-[4-(6-amino-pyridin-3-yl)-phenyl]-5-(4-chloro-phenyl)-4-oxo-4,5-dihydro-pyrazolo[3,4-d]pyrimidin-1-yl]-benzonitrile (prepared as described in example 28, 0.325 g, 0.629 mmol) is added to methanol saturated with hydrogen chloride gas (7 mL) with stirring. The reaction mixture is allowed to reach rt and stirred there for 24 h. The reaction mixture is then concentrated to a dry residue. It is taken in dry methanol (6 mL) and ammonium carbonate (0.593 g, 3.77 mmol) is added. After stirring at rt for 16 h, the reaction mixture is concentrated and the residue obtained is purified by preparative HPLC to afford 3-[6-[4-(6-ammo-pyridin-3-yl)-phenyl]-5-(4-chloro-phenyl)-4-oxo-4,5-dihydro-pyrazolo[3,4-d]pyrimidin-1-yl]-benzamidine. $^1$H NMR (Acetone-d$_6$, 400 MHz) δ 11.32 (br, 2H), 8.88 (br, 2H), 8.72 (m, 2H), 8.40 (s, 1H), 8.25 (m, 2H), 7.95 (m, 2H), 7.83 (m, 1H), 7.65 (m, 5H), 7.45 (m, 4H), 7.14 (d, 1H); LC-MS calculated for C$_{29}$H$_{21}$ClN$_8$O (M+H$^+$) 533.2, found 533.1.

Example 30

3-[6-[4-(5-Amino-pyridin-2-yl)-phenyl]-5-(4-chloro-phenyl)-4-oxo-4,5-dihydro-pyrazolo[3,4-d]pyrimidin-1-yl]-benzamidine

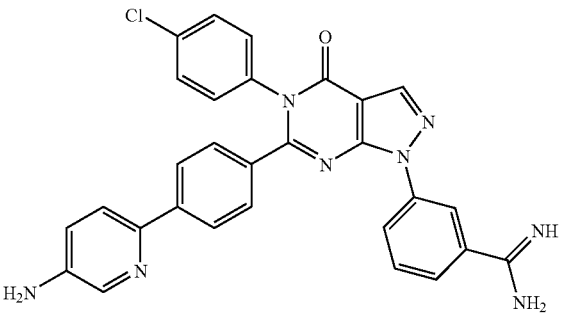

At 0° C., 3-[6-[4-(5-amino-pyridin-2-yl)-phenyl]-5-(4-chloro-phenyl)-4-oxo-4,5-dihydro-pyrazolo[3,4-d]pyrimidin-1-yl]-benzonitrile (prepared as described in example 27, 0.30 g, 0.58 mmol) is added to methanol saturated with hydrogen chloride gas (7 mL) with stirring. The reaction mixture is allowed to reach rt and stirred there for 30 h. The reaction mixture is then concentrated to a dry residue. It is taken in dry methanol (6 mL) and ammonium carbonate (0.548 g, 3.48 mmol) is added. After stirring at rt for 48 h, the reaction mixture is concentrated and the residue obtained is purified by preparative HPLC to afford 3-[6-[4-(5-amino-pyridin-2-yl)-phenyl]-5-(4-chloro-phenyl)-4-oxo-4,5-dihydro-pyrazolo[3,4-d]pyrimidin-1-yl]-benzamidine. $^1$H NMR (DMSO-d$_6$, 400 MHz) δ 9.40 (br, 4H), 8.62 (m, 2H), 8.53 (s, 1H), 8.32 (s, 1H), 8.0 (d, 1H), 7.83 (m, 4H), 7.64 (d, 1H), 7.43 (m, 5H), 6.96 (d, 1H), 5.6 (br, 1H); LC-MS calculated for C$_{29}$H$_{21}$ClN$_8$O (M+H$^+$) 533.2, found 533.1.

Example 31

3-(2-(4-bromophenyl)-1-(4-chlorophenyl)-6-oxo-1H-purin-9(6H)-yl)benzenesulfonamide

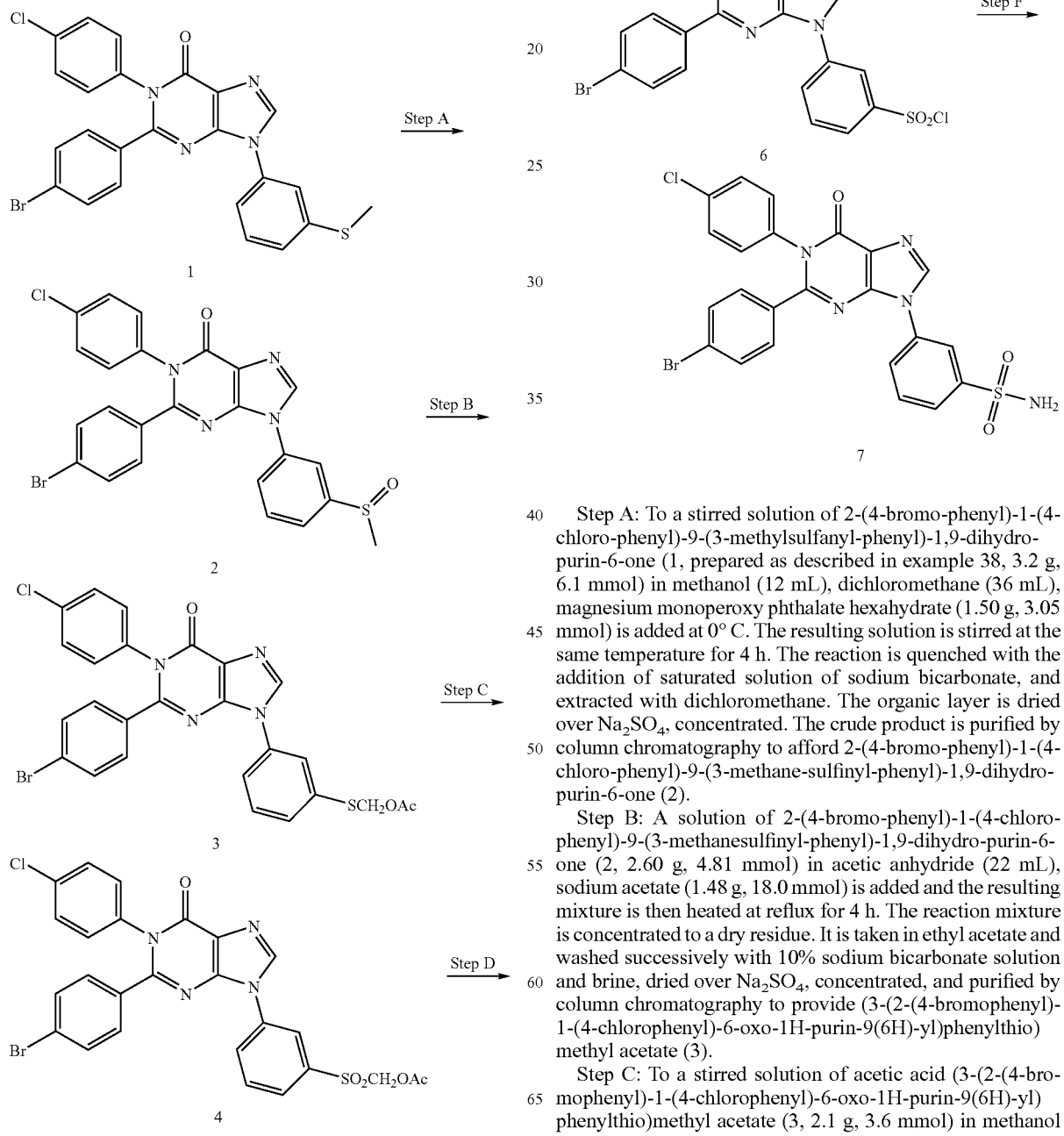

Step A: To a stirred solution of 2-(4-bromo-phenyl)-1-(4-chloro-phenyl)-9-(3-methylsulfanyl-phenyl)-1,9-dihydro-purin-6-one (1, prepared as described in example 38, 3.2 g, 6.1 mmol) in methanol (12 mL), dichloromethane (36 mL), magnesium monoperoxy phthalate hexahydrate (1.50 g, 3.05 mmol) is added at 0° C. The resulting solution is stirred at the same temperature for 4 h. The reaction is quenched with the addition of saturated solution of sodium bicarbonate, and extracted with dichloromethane. The organic layer is dried over Na$_2$SO$_4$, concentrated. The crude product is purified by column chromatography to afford 2-(4-bromo-phenyl)-1-(4-chloro-phenyl)-9-(3-methane-sulfinyl-phenyl)-1,9-dihydro-purin-6-one (2).

Step B: A solution of 2-(4-bromo-phenyl)-1-(4-chloro-phenyl)-9-(3-methanesulfinyl-phenyl)-1,9-dihydro-purin-6-one (2, 2.60 g, 4.81 mmol) in acetic anhydride (22 mL), sodium acetate (1.48 g, 18.0 mmol) is added and the resulting mixture is then heated at reflux for 4 h. The reaction mixture is concentrated to a dry residue. It is taken in ethyl acetate and washed successively with 10% sodium bicarbonate solution and brine, dried over Na$_2$SO$_4$, concentrated, and purified by column chromatography to provide (3-(2-(4-bromophenyl)-1-(4-chlorophenyl)-6-oxo-1H-purin-9(6H)-yl)phenylthio)methyl acetate (3).

Step C: To a stirred solution of acetic acid (3-(2-(4-bromophenyl)-1-(4-chlorophenyl)-6-oxo-1H-purin-9(6H)-yl)phenylthio)methyl acetate (3, 2.1 g, 3.6 mmol) in methanol (12 mL), dichloromethane (36 mL), magnesium monoperoxy phthalate hexahydrate (1.9 g, 3.97 mmol) is added at 0° C. The resulting solution is stirred at rt for 12 h. The reaction is quenched with the addition of saturated solution of sodium bicarbonate, and extracted with dichloromethane. The organic layer is dried over $Na_2SO_4$, concentrated. The crude product is purified by column chromatography to afford (3-(2-(4-bromophenyl)-1-(4-chlorophenyl)-6-oxo-1H-purin-9(6H)-yl)phenylsulfonyl)methyl acetate (4).

Step D, E and F: To a stirred solution of (3-(2-(4-bromophenyl)-1-(4-chlorophenyl)-6-oxo-1H-purin-9(6H)-yl) phenylsulfonyl)methyl acetate (4, 1.900 g, 3.09 mmol) in methanol (10 mL), dichloromethane (15 mL), 1 N aqueous sodium hydroxide solution (5 mL) is added at 0° C. The reaction mixture as stirred at that temperature for 2 h. Then it is concentrated to a dry residue. It is coevaporated with toluene to get rid of solvent traces. To a stirred solution of sulfinate salt (5) in dichloromethane (15 mL), sulfuryl chloride (0.41 g, 3.09 mmol) is added at 0° C. The reaction mixture as stirred at that temperature for 1.5 h. Then the reaction mixture is diluted with water and dichloromethane. The organic layers separated is dried, and concentrated to afford the sulfonyl chloride product (6). To a stirred solution of sulfonyl chloride in dry tetrahydrofuran (15 mL), aqueous ammonia solution (4 mL, 25% in water) is added at 0° C. The reaction mixture as stirred at that temperature for 6 h. Then the reaction mixture is diluted with water and dichloromethane. The organic layers separated is dried, and concentrated to afford the 3-[2-(4-bromo-phenyl)-1-(4-chloro-phenyl)-6-oxo-1,6-dihydro-purin-9-yl]-benzene sulfonamide (7). LC-MS calculated for $C_{23}H_{15}BrClN_5O_3S$ (M+H$^+$) 558.0, found 557.9.

Example 32

6-[4-(6-Amino-pyridin-3-yl)-phenyl]-5-(4-chloro-phenyl)-1-[3-(1H-tetrazol-5-yl)-phenyl]-1,5-dihydro-pyrazolo[3,4-d]pyrimidin-4-one

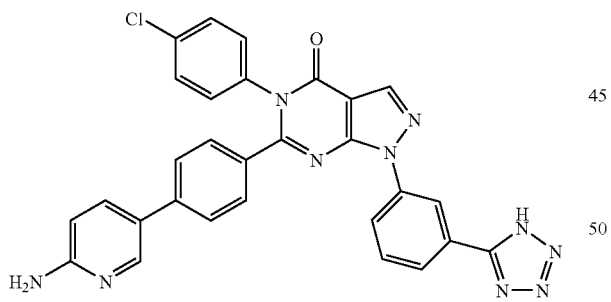

To a solution of 3-[6-[4-(5-amino-pyridin-2-yl)-phenyl]-5-(4-chloro-phenyl)-4-oxo-4,5-dihydro-pyrazolo[3,4-d]pyrimidin-1-yl]-benzonitrile (prepared as described in example 28, 0.375 g, 0.726 mmol) in N,N-dimethylformamide (7 mL), sodium azide (0.236 g, 3.63 mmol), ammonium chloride (0.19 g, 3.63 mmol) are added. The reaction mixture is then heated at 90° C. for 14 h. The reaction mixture is concentrated to a dry residue. It is purified by column chromatography to afford 6-[4-(6-amino-pyridin-3-yl)-phenyl]-5-(4-chloro-phenyl)-1-[3-(1H-tetrazol-5-yl)-phenyl]-1,5-dihydro-pyrazolo[3,4-d]pyrimidin-4-one. $^1$H NMR (DMSO-d$_6$, 400 MHz) δ 8.81 (s, 1H), 8.57 (s, 1H), 8.50 (br, 1H), 8.38 (m, 1H), 8.27 (m, 1H), 8.07 (d, 1H), 7.79 (m, 2H), 7.55 (m, 2H), 7.39-7.46 (m, 5H), 6.59 (d, 1H), 6.54 (br, 1H); LC-MS calculated for $C_{29}H_{19}ClN_{10}O$ (M+H$^+$) 559.1, found 559.1.

Example 33

6-[4-(5-amino-pyridin-2-yl)-phenyl]-5-(4-chloro-phenyl)-1-[3-(1H-tetrazol-5-yl)-phenyl]-1,5-dihydro-pyrazolo[3,4-d]pyrimidin-4-one

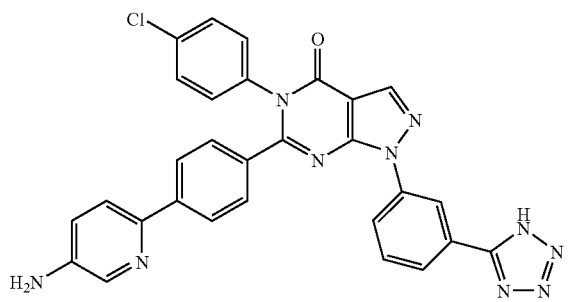 [SMILES: Nc1ccc(-c2ccc(-c3nc4c(cnn4-c4cccc(-c5nnn[nH]5)c4)c(=O)n3-c3ccc(Cl)cc3)cc2)nc1]

To a solution of 3-[6-[4-(6-amino-pyridin-3-yl)-phenyl]-5-(4-chloro-phenyl)-4-oxo-4,5-dihydro-pyrazolo[3,4-d]pyrimidin-1-yl]-benzonitrile (prepared as described in example 27, 0.230 g, 0.445 mmol) in N,N-dimethylformamide (4 mL), sodium azide (0.144 g, 2.22 mmol), ammonium chloride (0.120 g, 2.22 mmol) are added. The reaction mixture is then heated at 90° C. for 40 h. The reaction mixture is concentrated to a dry residue. It is purified by preparative HPLC to afford 6-[4-(5-amino-pyridin-2-yl)-phenyl]-5-(4-chloro-phenyl)-1-[3-(1H-tetrazol-5-yl)-phenyl]-1,5-dihydro-pyrazolo[3,4-d]pyrimidin-4-one. $^1$H NMR (DMSO-d$_6$, 400 MHz) δ 8.83 (s, 1H), 8.60 (s, 1H), 8.41 (d, 1H), 8.06 (d, 1H), 7.99 (m, 1H), 7.83 (m, 4H), 7.53 (m, 2H), 7.44 (m, 4H), 7.28 (br, 1H); LC-MS calculated for $C_{29}H_{19}ClN_{10}O$ (M+H$^+$) 559.1, found 559.1.

Example 34

2-(4-bromophenyl)-1-(4-chlorophenyl)-9-(3-(methylsulfonyl)-phenyl)-1H-purin-6(9H)-one

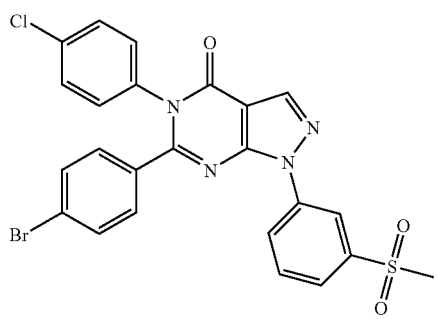 [SMILES: CS(=O)(=O)c1cccc(-n2ncc3c(=O)n(-c4ccc(Cl)cc4)c(-c4ccc(Br)cc4)nc32)c1]

The preparation of the title compound is described in example 38. LC-MS calculated for C24H16BrClN4O3S (M+H$^+$) 557.0, found 556.9.

Example 35

N-(3-(6-(4-(6-aminopyridin-3-yl)phenyl)-5-(4-chlorophenyl)-4-oxo-4,5-dihydro-1H-pyrazolo[3,4-d]pyrimidin-1-yl)phenyl)methanesulfonamide

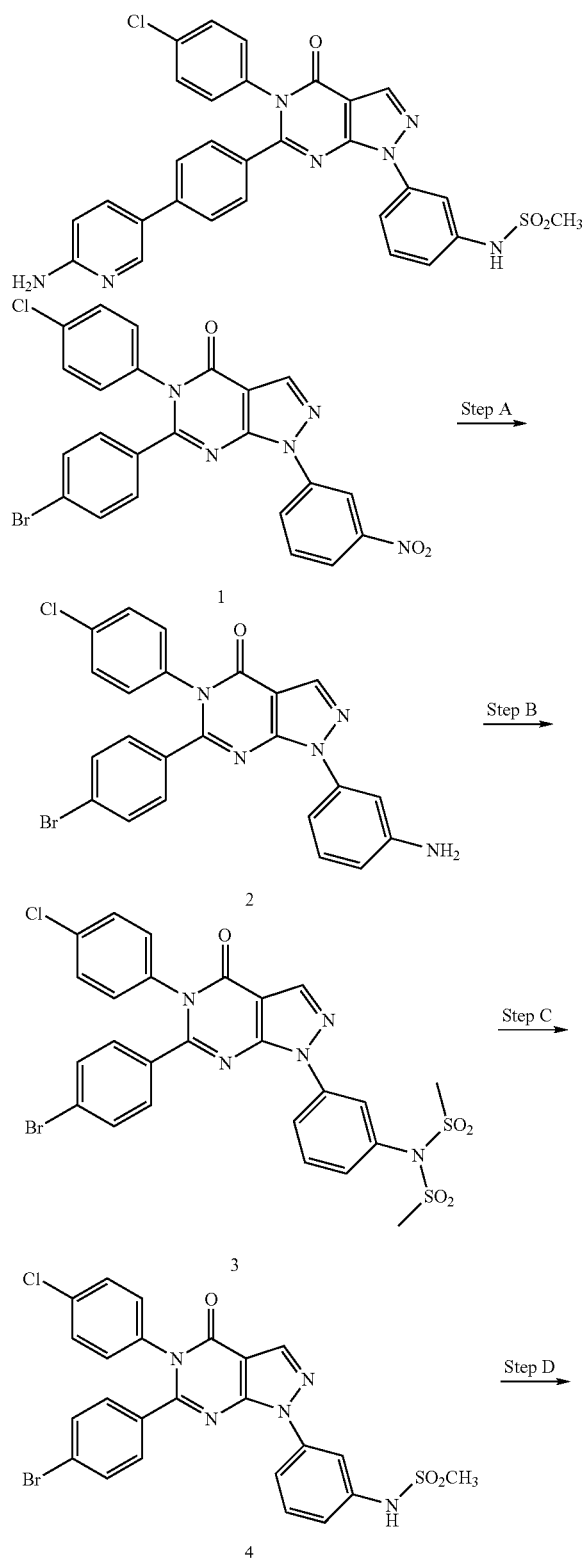

Step A: To a stirred solution of 6-(4-bromo-phenyl)-5-(4-chloro-phenyl)-1-(3-nitro-phenyl)-1,5-dihydro-pyrazolo[3,4-d]pyrimidin-4-one (1, 1.62 g, 3.09 mmol) in ethanol (58 mL), iron powder (0.86 g, 15.45 mmol) and saturated solution of ammonium chloride (24 mL) is added and the reaction mixture is heated at 80° C. for 6 h. The reaction mixture is filtered through the celite. The celite bed is washed well with methanol and chloroform. The filtrate is concentrated to afford a residue. It is dissolved in ethyl acetate, washed with 10% sodium bicarbonate solution, water and brine, dried over $Na_2SO_4$, concentrated. The crude product is taken in diethyl ether (4×) and stirred for 20 min and filtered at suction to provide 1-(3-amino-phenyl)-6-(4-bromo-phenyl)-5-(4-chloro-phenyl)-1,5-dihydro-pyrazolo[3,4-d]pyrimidin-4-one (2) as off-white solid.

Step B: To a stirred solution 1-(3-amino-phenyl)-6-(4-bromo-phenyl)-5-(4-chloro-phenyl)-1,5-dihydro-pyrazolo[3,4-d]pyrimidin-4-one (2, 1.3 g, 2.63 mmol) in dichloromethane (90 mL), methane sulphonyl chloride (0.6 g, 5.27 mmol), triethyl amine (0.93 g, 9.23 mmol) are added at 0° C. and the resulting mixture is stirred at rt. After 2 h, water is added and extracted with chloroform (3×). The combined organic layer is washed with brine, dried over $Na_2SO_4$, concentrated to provide bis-methane sulphonamide of 1-(3-amino-phenyl)-6-(4-bromo-phenyl)-5-(4-chloro-phenyl)-1,5-dihydro-pyrazolo[3,4-d]pyrimidin-4-one (3) as a off-white solid.

Step C: To a stirred solution of bis-methane sulphonamide of 1-(3-amino phenyl)-6-(4-bromo-phenyl)-5-(4-chloro-phenyl)-1,5-dihydro-pyrazolo[3,4-d]pyrimidin-4-one (3, 1.6 g) in tetrahydrofuran (20 mL), tetra-n-butyl ammonium fluoride (0.707 g, 2.71 mmol) is added and the resulting mixture is heated at reflux for 1 h. The reaction mixture is diluted with water and the compound is extracted with ethyl acetate (3×). The combined organic layer is washed with brine, dried over $Na_2SO_4$, concentrated, and purified by column chromatography to provide N-{3-[6-(4-bromo-phenyl)-5-(4-chloro-phenyl)-4-oxo-4,5-dihydro-pyrazolo[3,4-d]pyrimidin-1-yl]phenyl}-methane sulfonamide (4), as off-white solid.

Step D: N-{3-[6-(4-bromo-phenyl)-5-(4-chloro-phenyl)-4-oxo-4,5-dihydro-pyrazolo[3,4-d]pyrimidine-1-yl]phenyl}-methane sulfonamide (4, 1.00 g, 1.75 mmol) in N,N-dimethylformamide (20 mL) is taken in the round bottomed flask and is degassed with argon for 0.5 h. To the resulting mixture is added bis(pinacolato)diboron (0.53 g, 2.1 mmol), Pd(dppf)$_2$Cl$_2$ (0.128 g, 0.175 mmol), potassium acetate (0.51 g, 5.25 mmol) and the mixture is degassed with argon for 0.5 h. The reaction mixture is then heated at 80° C. for 3 h. The reaction mixture is cooled to rt and diluted with water and the compound is extracted with ethyl acetate (3×). The combined organic layer is washed with brine, dried over $Na_2SO_4$, concentrated, and purified by column chromatography to provide N-(3-{5-(4-chloro-phenyl)-4-oxo-6-[4-(4,4,5,5-tetramethyl-

[1,3,2]dioxaborolan-2-yl)phenyl]-4,5-dihydro-pyrazolo[3,4-d]pyrimidin-1-yl}-phenyl)-methanesulfonamide (5) as white solid.

In the last step, a solution of N-(3-{5-(4-chloro-phenyl)-4-oxo-6-[4-(4,4,5,5-tetramethyl-[1,3,2]dioxaborolan-2-yl)phenyl]-4,5-dihydro-pyrazolo[3,4-d]pyrimidin-1-yl}-phenyl)-methane sulfonamide (5, 0.5 g, 0.89 mmol) in N,N-dimethylformamide (15 mL) is degassed with argon for 0.5 h. Then 2-amino-5-bromopyridine (0.21 g, 1.22 mmol), cesium carbonate (0.53 g, 1.618 mmol), Pd(dppf)$_2$Cl$_2$ (0.03 g, 0.04 mmol) are added and the resulting solution is degassed with argon for 0.5 h. The reaction mixture is then heated at 100° C. for 6 h. The reaction mixture is cooled to rt and diluted with water and extracted with ethyl acetate (3×). The combined organic layer is washed with brine, dried over Na$_2$SO$_4$, concentrated, and purified by preparative HPLC to afford N-{3-[6-[4-(6-amino-pyridin-3-yl)-phenyl]-5-(4-chloro-phenyl)-4-oxo-4,5-dihydro-pyrazolo[3,4-d]pyrimidin-1-yl]-phenyl}-methane sulfonamide, as a pale yellow solid. $^1$H NMR (CD$_3$OD, 400 MHz) δ 8.34 (s, 1H), 8.27 (s, 1H), 8.15 (m, 2H), 7.90 (d, 1H), 7.60 (m, 5H), 7.4 (m, 2H), 7.34 (m, 2H), 7.2 (d, 1H), 7.0 (d, 1H), 2.99 (s, 3H); LC-MS calculated for C$_{29}$H$_{22}$ClN$_7$O$_3$S (M+H$^+$) 584.1, found 584.1.

Example 36

2-[4-(6-Amino-pyridin-3-yl)-phenyl]-1-(4-chloro-phenyl)-9-(3-methanesulfonyl-phenyl)-1,9-dihydro-purin-6-one

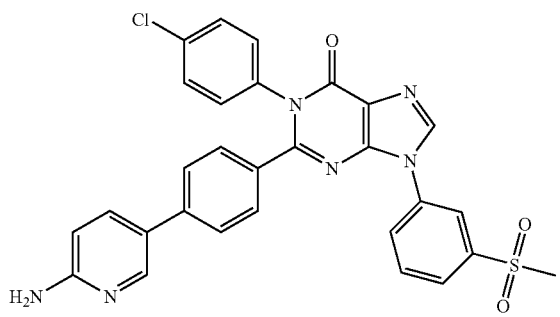

A solution of 1-(4-chloro-phenyl)-9-(3-methanesulfonyl-phenyl)-2-[4-(4,4,5,5-tetramethyl-[1,3,2]dioxaborolan-2-yl)-phenyl]-1,9-dihydro-purin-6-one (prepared as described in example 38, 0.300 g, 0.497 mmol) in N,N-dimethylformamide (20 mL) is degassed with argon for 0.5 h. Then 2-amino-5-bromopyridine (0.129 g, 0.746 mmol), cesium carbonate (0.324 g, 0.995 mmol), Pd(dppf)$_2$Cl$_2$ (0.036 g, 0.049 mmol) is added and the resulted mixture is degassed with argon for 0.5 h. The reaction mixture is then heated at 100° C. for 6 h. The reaction mixture is cooled to rt and diluted with water and extracted with ethyl acetate (3×). The combined organic layer is washed with brine, dried over Na$_2$SO$_4$, concentrated, and purified by column chromatography to afford 2-[4-(6-amino-pyridin-3-yl)-phenyl]-1-(4-chloro-phenyl)-9-(3-methanesulfonyl-phenyl)-1,9-dihydro-purin-6-one. $^1$H NMR (DMSO-d$_6$, 400 MHz) δ 8.77 (br, 1H), 8.45 (m, 1H), 8.30 (m, 1H), 8.23-8.27 (m, 2H), 8.13 (br, 1H), 8.04 (d, 1H), 7.90 (t, 1H), 7.55 (m, 2H), 7.41-7.53 (m, 5H), 7.01 (d, 1H), 3.30 (s, 3H); LC-MS calculated for C$_{29}$H$_{21}$ClN$_6$O$_3$S (M+H$^+$) 569.1, found 569.2.

Example 37

N-(3-(6-(4-(5-aminopyridin-2-yl)phenyl)-5-(4-chlorophenyl)-4-oxo-4,5-dihydro-1H-pyrazolo[3,4-d]pyrimidin-1-yl)phenyl)methanesulfonamide

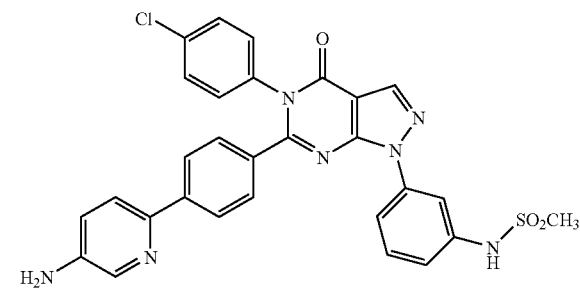 [SMILES: CS(=O)(=O)Nc1cccc(-n2ncc3c(=O)n(-c4ccc(Cl)cc4)c(-c4ccc(-c5ccc(N)cn5)cc4)nc32)c1]

A solution of N-(3-{5-(4-chloro-phenyl)-4-oxo-6-[4-(4,4,5,5-tetramethyl-[1,3,2]dioxa-borolan-2-yl)phenyl]-4,5-dihydro-pyrazolo[3,4-d]pyrimidin-1-yl}-phenyl)-methane sulfonamide (prepared as described in example 35, 0.28 g, 0.453 mmol) in N,N-dimethylformamide (15 mL) is degassed with argon for 0.5 h. Then 5-amino-2-bromopyridine (0.120 g, 0.679 mmol), cesium carbonate (0.30 g, 0.90 mmol), Pd(dppf)$_2$Cl$_2$ (0.016 g, 0.020 mmol) are added and the resulting solution is degassed with argon for 0.5 h. The reaction mixture is then heated at 100° C. for 12 h. The reaction mixture is cooled to rt and diluted with water and extracted with ethyl acetate (3×). The combined organic layer is washed with brine, dried over Na$_2$SO$_4$, concentrated, and purified by column chromatography to afford N-{3-[6-[4-(5-amino-pyridin-2-yl)-phenyl]-5-(4-chloro-phenyl)-4-oxo-4,5-dihydro-pyrazolo[3,4-d]pyrimidin-1-yl]-phenyl}-methane sulfonamide. $^1$H NMR (CD$_3$OD, 400 MHz) δ 8.37 (s, 1H), 8.30 (s, 1H), 7.95 (m, 2H), 7.90 (d, 1H), 7.71 (m, 5H), 7.50 (t, 1H), 7.35 (m, 4H), 7.20 (d, 1H), 2.99 (s, 3H); LC-MS calculated for C$_{29}$H$_{22}$ClN$_7$O$_3$S (M+H$^+$) 584.1, found 584.0.

Example 38

2-[4-(5-Amino-pyridin-2-yl)-phenyl]-1-(4-chloro-phenyl)-9-(3-methanesulfonyl-phenyl)-1,9-dihydro-purin-6-one

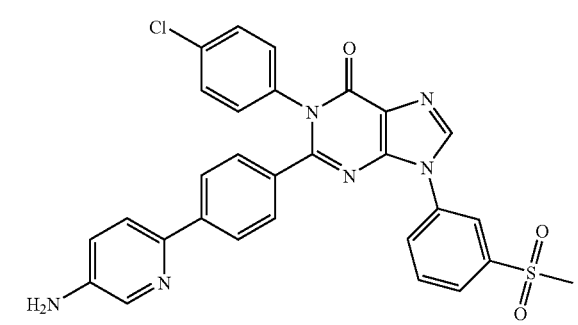 [SMILES: CS(=O)(=O)c1cccc(-n2cnc3c(=O)n(-c4ccc(Cl)cc4)c(-c4ccc(-c5ccc(N)cn5)cc4)nc32)c1]

51

Preparation of 5-amino-1-(3-methylsulfanyl-phenyl)-1H-imidazole-4-carboxylic acid ethyl ester

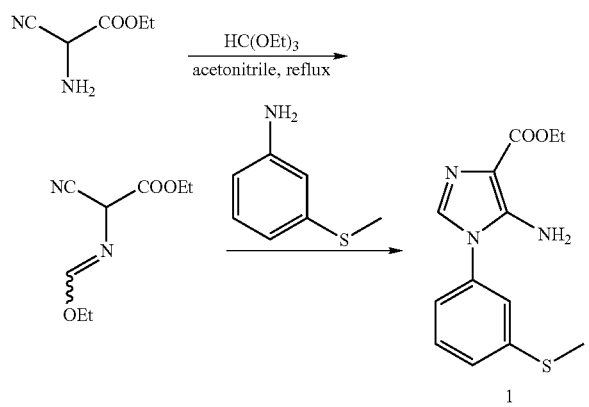

A solution of amino-cyano-acetic acid ethyl ester (8.00 g, 62.5 mmol) and triethyl orthoformate (9.20 g, 62.5 mmol) in acetonitrile (85 mL) is heated at reflux for 45 min. The reaction mixture is allowed to reach rt and 3-methylsulfanyl-phenylamine (8.70 g, 62.5 mmol) is added and stirred at rt for 24 h. The crude product obtained is purified by column chromatography to afford the product (1).

Preparation of 2-(4-bromo-phenyl)-1-(4-chloro-phenyl)-9-(3-methylsulfanyl-phenyl)-1,9-dihydro-purin-6-one

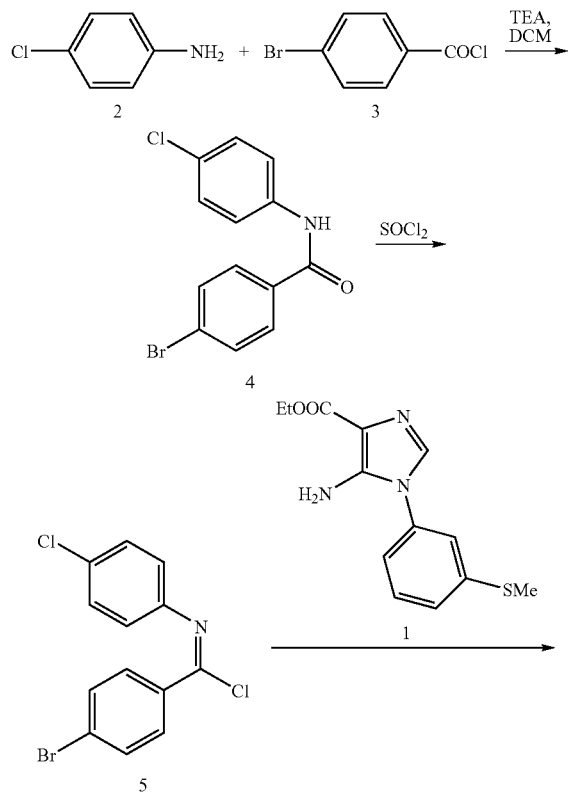

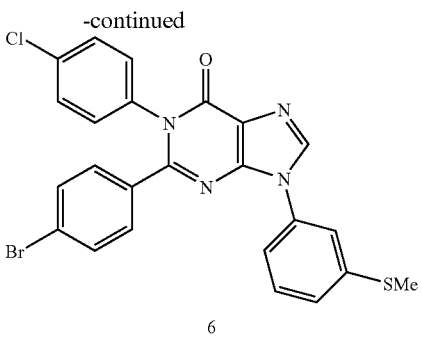

4-Bromo-N-(4-chloro-phenyl)-benzimidoyl chloride is prepared by heating 4-bromo-N-(4-chloro-phenyl)-benzamide (16.5 g, 53.0 mmol) and thionyl chloride (140 mL) for 1 h. The clear solution is concentrated and the residue obtained is coevaporated with toluene (100 mL). Then 5-amino-1-(3-methylsulfanyl-phenyl)-1H-imidazole-4-carboxylic acid ethyl ester (1, 9.8 g, 35.33 mmol) is added and the resulting mixture is heated to 170° C. with out solvent for 6 h. The crude product obtained is purified by column chromatography (6).

Preparation of 1-(4-chloro-phenyl)-9-(3-methane-sulfonyl-phenyl)-2-[4-(4,4,5,5-tetramethyl-[1,3,2]dioxaborolan-2-yl)-phenyl]-1,9-dihydro-purin-6-one

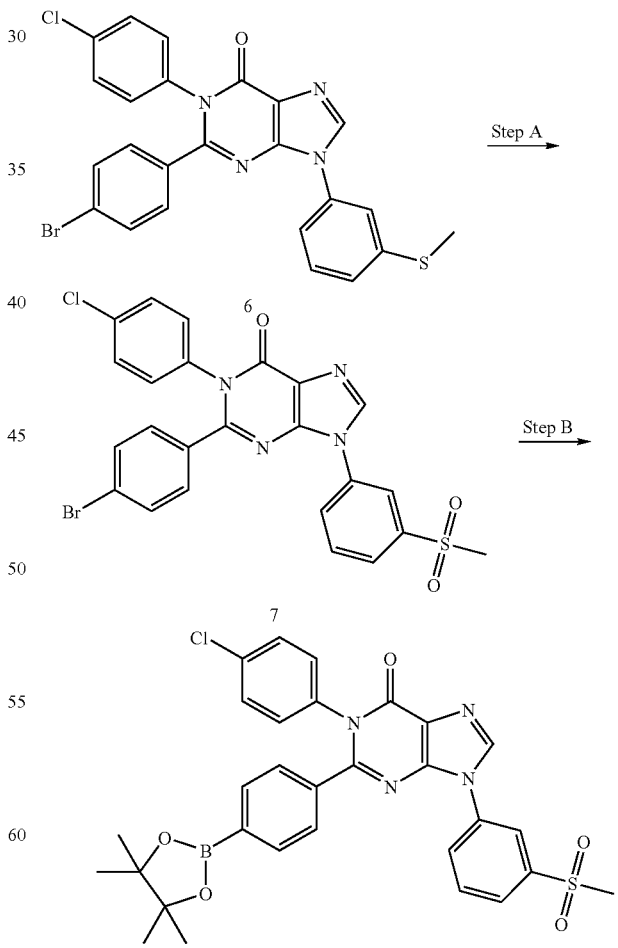

Step A: To a stirred solution of 2-(4-bromo-phenyl)-1-(4-chloro-phenyl)-9-(3-methylsulfanyl-phenyl)-1,9-dihydro-purin-6-one (6, 1.0 g, 1.9 mmol) in methanol (7 mL), dichloromethane (21 mL), magnesium monoperoxy phthalate hexahydrate (1.03 g, 2.09 mmol) is added. The resulting solution is stirred at rt for 12 h. The reaction is quenched with the addition of saturated solution of sodium bicarbonate, and extracted with dichloromethane. The organic layer is dried over $Na_2SO_4$, concentrated. The crude product is purified by column chromatography to afford methyl sulfone (7).

Step B: A solution of methyl sulfone (7, 0.630 g, 1.13 mmol) in N,N-dimethylformamide (20 mL) is taken in the round bottomed flask and is degassed with argon for 0.5 h. To the resulting mixture is added bis(pinacolato)diboron (0.345 g, 1.36 mmol), $Pd(dppf)_2Cl_2$ (0.82 g, 0.113 mmol), potassium acetate (0.33 g, 3.4 mmol) and the mixture is degassed with argon for 0.5 h. The reaction mixture is then heated at 80° C. for 2 h. The reaction mixture is cooled to rt and diluted with water and the compound is extracted with ethyl acetate (3×). The combined organic layer is washed with brine, dried over $Na_2SO_4$, concentrated, and purified by column chromatography to provide 1-(4-chloro-phenyl)-9-(3-methanesulfonyl-phenyl)-2-[4-(4,4,5,5-tetramethyl-[1,3,2]-dioxaborolan-2-yl)-phenyl]-1,9-dihydro-purin-6-one (8).

Preparation of 2-[4-(5-amino-pyridin-2-yl)-phenyl]-1-(4-chloro-phenyl)-9-(3-methanesulfonyl-phenyl)-1,9-dihydro-purin-6-one A solution of 1-(4-chloro-phenyl)-9-(3-methanesulfonyl-phenyl)-2-[4-(4,4,5,5-tetramethyl-[1,3,2]dioxaborolan-2-yl)-phenyl]-1,9-dihydro-purin-6-one (8, 0.21 g, 0.348 mmol) in N,N-dimethylformamide (15 mL) is degassed with argon for 0.5 h. Then 5-amino-2-bromopyridine (0.090 g, 0.52 mmol), cesium carbonate (0.227 g, 0.696 mmol), $Pd(dppf)_2Cl_2$ (0.025 g, 0.035 mmol) is added and the resulted mixture is degassed with argon for 0.5 h. The reaction mixture is then heated at 100° C. for 2 h. The reaction mixture is cooled to rt and diluted with water and extracted with ethyl acetate (3×). The combined organic layer is washed with brine, dried over $Na_2SO_4$, concentrated, and purified by preparative HPLC to afford 2-[4-(5-amino-pyridin-2-yl)-phenyl]-1-(4-chloro-phenyl)-9-(3-methanesulfonyl-phenyl)-1,9-dihydro-purin-6-one. $^1$H NMR ($CD_3OD$, 400 MHz) δ 8.63 (s, 1H), 8.56 (s, 1H), 8.23 (d, 1H), 8.09 (d, 1H), 7.95 (s, 1H), 7.86-7.90 (m, 2H), 7.68-7.71 (m, 2H), 7.59 (m, 3H), 7.39 (m, 2H), 7.34 (m, 2H), 3.21 (s, 3H); LC-MS calculated for $C_{29}H_{21}ClN_6O_3S$ (M+H$^+$) 569.1, found 569.1.

Example 39

6-(4-Bromo-phenyl)-5-(4-chloro-phenyl)-1-(3-nitro-phenyl)-1,5-dihydro-pyrazolo[3,4-d]pyrimidin-4-one

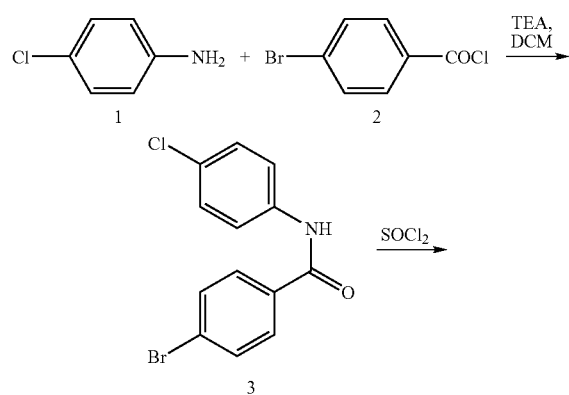

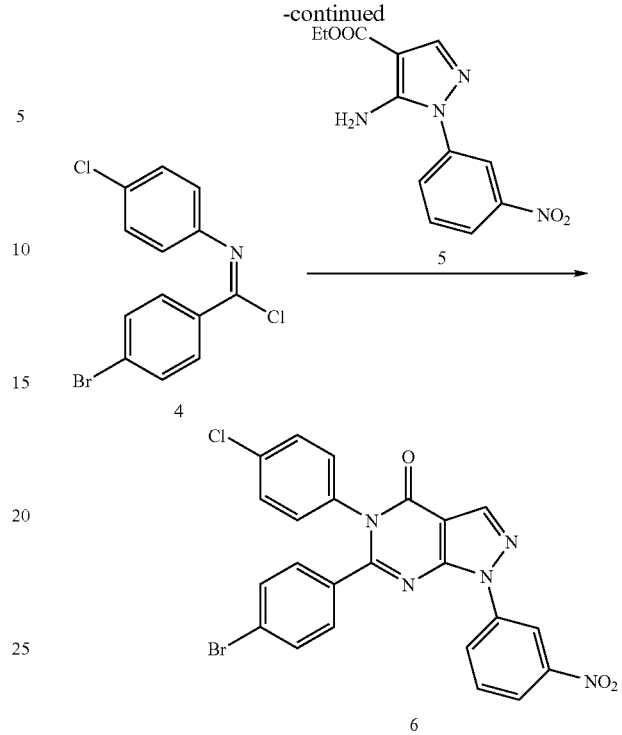

4-Bromo-N-(4-chloro-phenyl)-benzimidoyl chloride (4) is prepared by heating 4-bromo-N-(4-chloro-phenyl)-benzamide (3, 22.40 g, 72.4 mmol) and thionyl chloride (150.0 mL) for 1 h. The clear solution is concentrated and the residue obtained is coevaporated with toluene (100 mL). To the residue a solution of 5-amino-1-(3-nitro-phenyl)-1H-pyrazole-4-carboxylic acid ethyl ester (5, 10 g, 36.2 mmol) in dry chloroform (100 mL) is added and the resulting mixture is concentrated to a dry residue. Then it is heated to 170° C. without solvent for 6 h. The crude product obtained is purified by column chromatography (silica gel, 60-120 mesh) to afford the product as yellow solid (yield 53%). HPLC-MS calculated for $C_{23}H_{13}BrClN_5O_3$ (M+H$^+$) 523.9, found 523.9.

5-Amino-1-(3-nitro-phenyl)-1H-pyrazole-4-carboxylic acid ethyl ester (5) used above is prepared as described below.

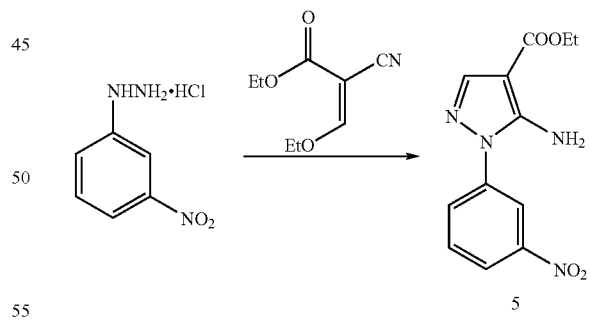

To a stirred solution of 3-nitro-phenyl hydrazine hydrochloride (12.0 g, 63.29 mmol) in absolute ethanol (396 mL), sodium hydroxide (2.53 g, 63.29 mmol) is added and the reaction mixture is stirred for 0.5 h. To the resulting mixture is added ethyl (ethoxymethylene)cyanoacetate (10.7 g, 63.69 mmol) and heated to 80° C. for 2 h. The reaction mixture is concentrated and the residue is taken in ethyl acetate, washed well with water. After washing with saturated brine solution, the organic layer is dried ($Na_2SO_4$) and concentrated to afford the crude product. The product is purified by column chromatography over silica gel (60-120 mesh) using 12% ethyl acetate—pet ether solvent mixture as eluent.

4-Bromo-N-(4-chloro-phenyl)-benzamide (3) used is prepared by the following procedure. To a solution of 4-chloroaniline (1, 66.0 g, 517.0 mmol) and 4-bromobenzoyl chloride (2, 109.0 g, 497.0 mmol) in dichloromethane (1200 mL) is added triethyl amine (83.0 mL, 596.0 mmol). The reaction mixture is then poured into 0.05 N sodium hydroxide solution and the resulted suspension is stirred at rt for 1 h. The solid formed is filtered and washed with water. The resulted white solid is dried under vacuum. The product is used in the next step reaction.

Example 40

3-(6-(4-bromophenyl)-5-(4-chlorophenyl)-4-oxo-4,5-dihydro-1H-pyrazolo[3,4-d]pyrimidin-1-yl)benzonitrile

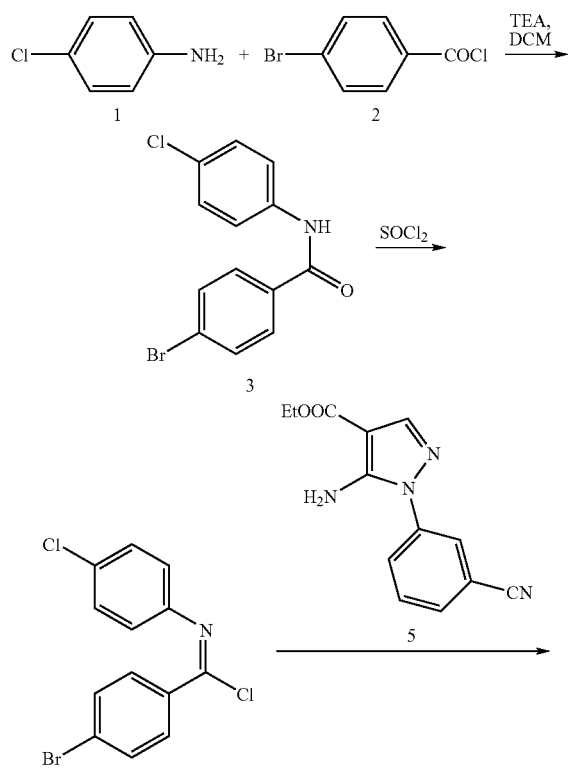

4-Bromo-N-(4-chloro-phenyl)-benzimidoyl chloride (4) is prepared by heating 4-bromo-N-(4-chloro-phenyl)-benzamide (3, 24.2 g, 78.0 mmol) and thionyl chloride (150 mL) for 1 h. The clear solution is concentrated and the residue obtained is coevaporated with toluene (100 mL). Then 5-amino-1-(3-cyano-phenyl)-1H-pyrazole-4-carboxylic acid ethyl ester (5, 10 g, 39.9 mmol) is added and the resulting mixture is heated to 170° C. with out solvent for 6 h. The crude product obtained is purified by column chromatography (silica gel, 60-120 mesh) to afford the product as yellow solid (6). LC-MS calculated for $C_{24}H_{13}BrClN_5O$ (M+H$^+$) 502.0, found 502.8.

5-Amino-1-(3-cyano-phenyl)-1H-pyrazole-4-carboxylic acid ethyl ester (5) used above is prepared as described below.

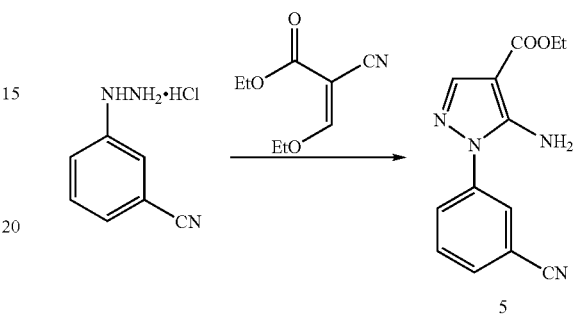

To a stirred solution of 3-cyano-phenyl hydrazine hydrochloride (42.0 g, 247 mmol) in absolute ethanol (1200 mL), sodium hydroxide (17.8 g, 445 mmol) is added and the reaction mixture is stirred for 0.5 h. To the resulting mixture is added ethyl (ethoxymethylene) cyanoacetate (41.9 g, 247.7 mmol) and heated to 80° C. for 2 h. The reaction mixture is concentrated and the residue is taken in ethyl acetate, washed well with water. After washing with saturated brine solution, the organic layer is dried ($Na_2SO_4$) and concentrated to afford the crude product. The product is purified by column chromatography over silica gel (60-120 mesh) using ethyl acetate—pet ether solvent mixture as eluent (5).

4-Bromo-N-(4-chloro-phenyl)-benzamide (3) used is prepared by the following procedure. To a solution of 4-chloroaniline (1, 66.0 g, 517.4 mmol) and 4-bromobenzoyl chloride (2, 109.0 g, 497.5 mmol) in dichloromethane (1200 mL) is added triethyl amine (83.2 mL, 597.0 mmol). The reaction mixture is then poured into 0.05 N sodium hydroxide solution and the resulted suspension is stirred at rt for 1 h. The solid formed is filtered and washed well with water. It is dried in vacuo and used for the next step.

Example 41

3-[2-[4-(5-Amino-pyridin-2-yl)-phenyl]-1-(4-chlorophenyl)-6-oxo-1,6-dihydro-purin-9-yl]-benzamidine

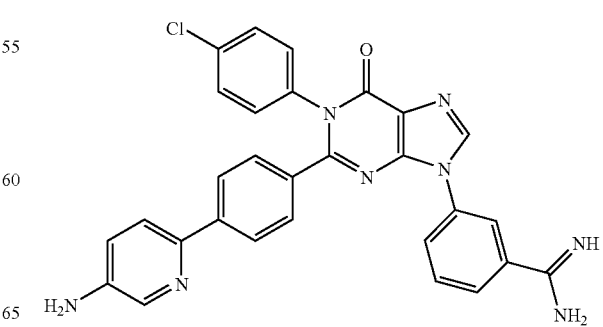

To 3-[2-[4-(5-amino-pyridin-2-yl)-phenyl]-1-(4-chlorophenyl)-6-oxo-1,6-dihydro-purin-9-yl]-benzonitrile (prepared as described in example 43, 0.29 g, 0.56 mmol), methanol saturated with hydrogen chloride gas (15 mL) is added at 0° C. with stirring. The reaction mixture is allowed to reach rt and stirred there for 12 h. The reaction mixture is then concentrated to a dry residue. It is taken in dry methanol (15 mL) and ammonium carbonate (0.520 g, 3.37 mmol) is added. After stirring at rt for 24 h, the reaction mixture is concentrated and the residue obtained is purified by column chromatography to afford 3-[2-[4-(5-amino-pyridin-2-yl)-phenyl]-1-(4-chloro-phenyl)-6-oxo-1,6-dihydro-purin-9-yl]-benzamidine. $^1$H NMR (DMSO-d$_6$, 400 MHz) δ 8.65 (s, 1H), 8.29 (s, 1H), 8.14 (s, 1H), 7.96-8.03 (m, 3H), 7.77 (d, 2H), 7.69 (m, 1H), 7.63 (m, 2H), 7.34-7.43 (m, 5H), 6.96 (br, 1H), 5.60 (br, 2H); LC-MS calculated for $C_{29}H_{21}ClN_8O$ (M+H$^+$) 533.2, found 534.2.

Example 42

3-[2-[4-(5-Amino-pyridin-2-yl)-phenyl]-1-(4-chlorophenyl)-6-oxo-1,6-dihydro-purin-9-yl]-benzene sulfonamide

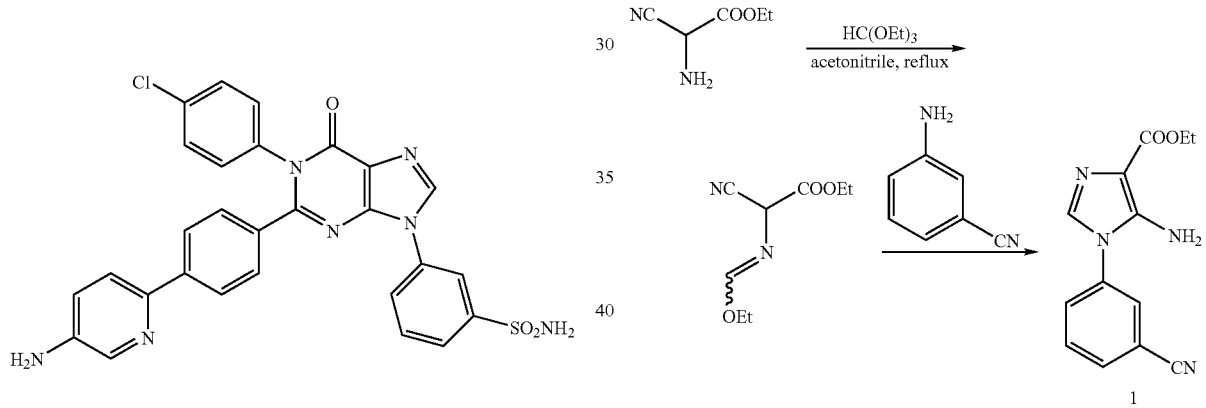

A solution of 3-{5-(4-chloro-phenyl)-4-oxo-6-[4-(4,4,5,5-tetramethyl-[1,3,2]-dioxaborolan-2-yl)-phenyl]-4,5-dihydro-pyrazolo[3,4-d]pyrimidin-1-yl}-benzene sulfonamide (prepared as described in example 25, 0.500 g, 0.898 mmol) in N,N-dimethylformamide (20 mL) is degassed with argon for 0.5 h. Then 5-amino-2-bromopyridine (0.220 g, 1.24 mmol), cesium carbonate (0.540 g, 1.65 mmol), Pd(dppf)$_2$Cl$_2$ (0.060 g, 0.083 mmol) is added and the resulted mixture is degassed with argon for 0.5 h. The reaction mixture is then heated at 100° C. for 4 h. The reaction mixture is cooled to rt and diluted with water and extracted with ethyl acetate (3×). The combined organic layer is washed with brine, dried over Na$_2$SO$_4$, concentrated, and purified by preparative HPLC to afford 3-[2-[4-(5-amino-pyridin-2-yl)-phenyl]-1-(4-chloro-phenyl)-6-oxo-1,6-dihydro-purin-9-yl]-benzene sulfonamide. $^1$H NMR (CD$_3$OD, 400 MHz) δ 8.57 (s, 1H), 8.46 (m, 1H), 8.06 (m, 1H), 8.01 (m, 1H), 7.93 (m, 2H), 7.78 (m, 1H), 7.65 (m, 5H), 7.37 (m, 4H); LC-MS calculated for $C_{28}H_{20}ClN_7O_3S$ (M+H$^+$) 570.1, found 570.0.

Example 43

3-[2-[4-(5-Amino-pyridin-2-yl)-phenyl]-1-(4-chlorophenyl)-6-oxo-1,6-dihydro-purin-9-yl]-benzonitrile

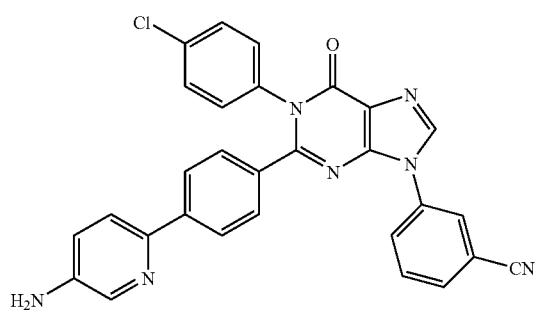 [SMILES: N#Cc1cccc(-n2cnc3c(=O)n(-c4ccc(Cl)cc4)c(-c4ccc(-c5ccc(N)cn5)cc4)nc32)c1]

Preparation of 5-amino-1-(3-cyano-phenyl)-1H-imidazole-4-carboxylic acid ethyl ester A solution of amino-cyano-acetic acid ethyl ester (10.6 g, 83.3 mmol) and triethyl orthoformate (12.35 g, 83.3 mmol) in acetonitrile (110 mL) is heated at reflux for 45 min. The reaction mixture is allowed to reach rt and 3-amino-benzonitrile (9.80 g, 83.3 mmol) is added and stirred at rt for 48 h. The crude product obtained is purified by column chromatography (1).

Preparation of 3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-benzonitrile

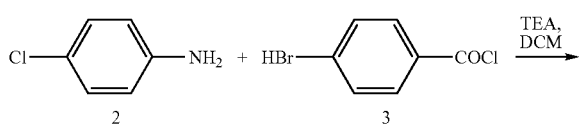

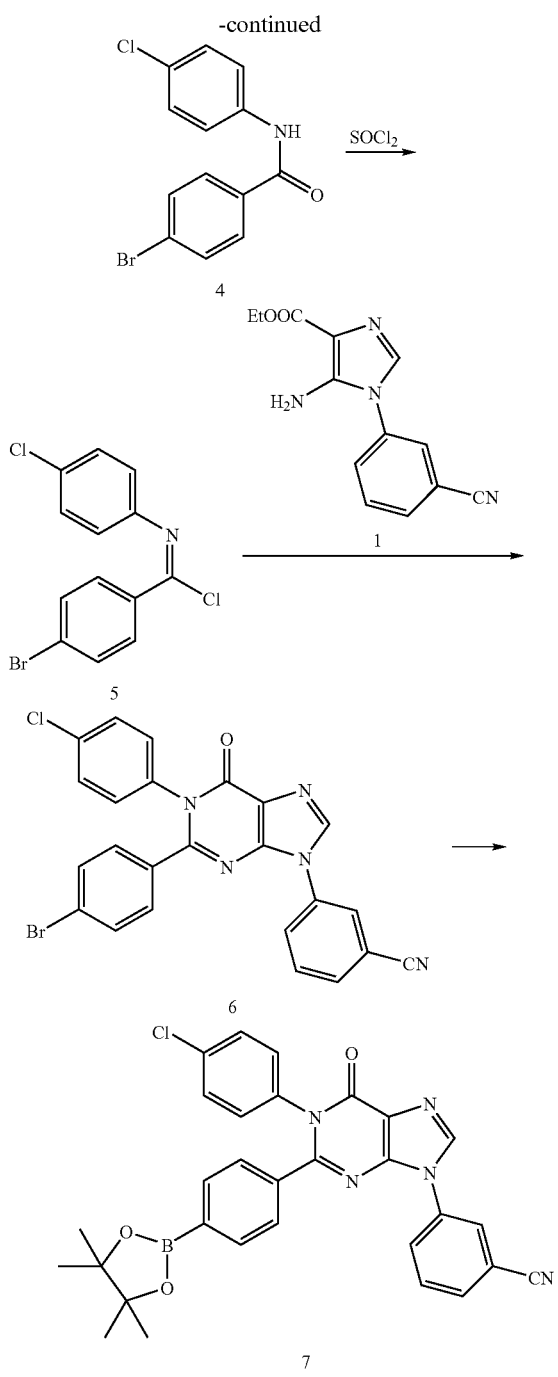

resulting mixture is added bis(pinacolato)diboron (4.8 g, 19.0 mmol), Pd(dppf)$_2$Cl$_2$ (1.1 g, 1.59 mmol), potassium acetate (4.68 g, 47.7 mmol) and the mixture is degassed with argon for 0.5 h. The reaction mixture is then heated at 80° C. for 2 h. The reaction mixture is cooled to rt and diluted with water and the compound is extracted with ethyl acetate (3×). The combined organic layer is washed with brine, dried over Na$_2$SO$_4$, concentrated, and purified by column chromatography to provide 3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-benzonitrile (7) as white solid.

Preparation of 3-[2-[4-(5-amino-pyridin-2-yl)-phenyl]-1-(4-chloro-phenyl)-6-oxo-1,6-dihydro-purin-9-yl]-benzonitrile A solution of 3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-benzonitrile (7, 1.00 g, 1.81 mmol) in N,N-dimethylformamide (40 mL) is degassed with argon for 0.5 h. Then 5-amino-2-bromopyridine (0.47 g, 2.72 mmol), cesium carbonate (1.18 g, 3.62 mmol), Pd(dppf)$_2$Cl$_2$ (0.13 g, 0.181 mmol) is added and the resulted mixture is degassed with argon for 0.5 h. The reaction mixture is then heated at 100° C. for 4 h. The reaction mixture is cooled to it and diluted with water and extracted with ethyl acetate (3×). The combined organic layer is washed with brine, dried over Na$_2$SO$_4$, concentrated, and purified by column chromatography to afford 3-[2-[4-(5-amino-pyridin-2-yl)-phenyl]-1-(4-chloro-phenyl)-6-oxo-1,6-dihydro-purin-9-yl]-benzonitrile. LC-MS calculated for C$_{29}$H$_{18}$ClN$_7$O (M+H$^+$) 516.1, found 516.0.

Example 44

3-[2-[4-(6-Amino-pyridin-3-yl)-phenyl]-1-(4-chlorophenyl)-6-oxo-1,6-dihydro-purin-9-yl]-benzonitrile

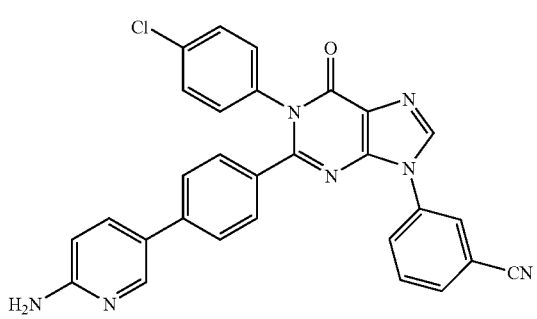 [SMILES: N#Cc1cccc(-n2cnc3c(=O)n(-c4ccc(Cl)cc4)c(-c4ccc(-c5ccc(N)nc5)cc4)nc32)c1]

4-Bromo-N-(4-chloro-phenyl)-benzimidoyl chloride is prepared by heating 4-bromo-N-(4-chloro-phenyl)-benzamide (17.6 g, 56.8 mmol) and thionyl chloride (125 mL) for 1 h. The clear solution is concentrated and the residue obtained is coevaporated with toluene (100 mL). Then 5-amino-1-(3-cyano-phenyl)-1H-imidazole-4-carboxylic acid ethyl ester (1, 9.70 g, 37.8 mmol) is added and the resulting mixture is heated to 170° C. without solvent for 6 h. The crude product obtained is purified by column chromatography.

3-[2-(4-Bromo-phenyl)-1-(4-chloro-phenyl)-6-oxo-1,6-dihydro-purin-9-yl]-benzonitrile (6, 8.00 g, 15.9 mmol) in N,N-dimethylformamide (200 mL) is taken in the round bottomed flask and is degassed with argon for 0.5 h. To the A solution of 3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-benzonitrile (prepared as described in example 43, 0.800 g, 1.45 mmol) in N,N-dimethylformamide (30 mL) is degassed with argon for 0.5 h. Then 2-amino-5-bromopyridine (0.37 g, 2.18 mmol), cesium carbonate (0.95 g, 3.63 mmol), Pd(dppf)$_2$Cl$_2$ (0.1 g, 0.181 mmol) is added and the resulted mixture is degassed with argon for 0.5 h. The reaction mixture is then heated at 100° C. for 4 h. The reaction mixture is cooled to rt and diluted with water and extracted with ethyl acetate (3×). The combined organic layer is washed with brine, dried over Na$_2$SO$_4$, concentrated, and purified by column chromatography to afford 3-[2-[4-(6-amino-pyridin-3- yl)-phenyl]-1-(4-chloro-phenyl)-6-oxo-1,6-dihydro-purin-9-yl]-benzonitrile. LC-MS calculated for $C_{29}H_{18}ClN_7O$ (M+H$^+$) 516.1, found 516.0.

Example 45

N-{3-[1-(4-Chloro-phenyl)-6-oxo-2-(4-pyrimidin-2-yl-phenyl)-1,6-dihydro-purin-9-yl]-phenyl}-methane sulfonamide

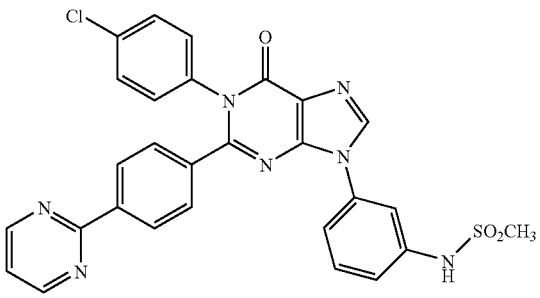

A solution of N-(3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-phenyl)-methane sulfonamide (prepared as described in example 26, 0.55 g, 0.88 mmol) in N,N-dimethylformamide (15 mL) is degassed with argon for 0.5 h. Then 2-bromo-pyrimidine (0.21 g, 1.32 mmol), cesium carbonate (0.57 g, 1.76 mmol), Pd(dppf)$_2$Cl$_2$ (0.032 g, 0.044 mmol) is added and the resulted mixture is degassed with argon for 0.5 h. The reaction mixture is then heated at 100° C. for 4 h. The reaction mixture is cooled to rt and diluted with water and extracted with ethyl acetate (3×). The combined organic layer is washed with brine, dried over Na$_2$SO$_4$, concentrated, and purified by column chromatography to afford N-{3-[1-(4-chloro-phenyl)-6-oxo-2-(4-pyrimidin-2-yl-phenyl)-1,6-dihydro-purin-9-yl]-phenyl}-methane sulfonamide. $^1$H NMR (DMSO-d$_6$, 400 MHz) δ 10.13 (br, 1H), 9.18 (s, 1H), 9.15 (s, 2H), 8.52 (s, 1H), 8.04 (m, 1H), 7.80 (m, 3H), 7.60 (m, 2H), 7.50 (m, 5H), 7.18 (dd, 1H), 3.02 (s, 3H); LC-MS calculated for $C_{28}H_{20}ClN_7O_3S$ (M+H$^+$) 570.1, found 569.9.

Example 46

1-(4-Chloro-phenyl)-9-(3-methanesulfonyl-phenyl)-2-(4-pyrazin-2-yl-phenyl)-1,9-dihydro-purin-6-one

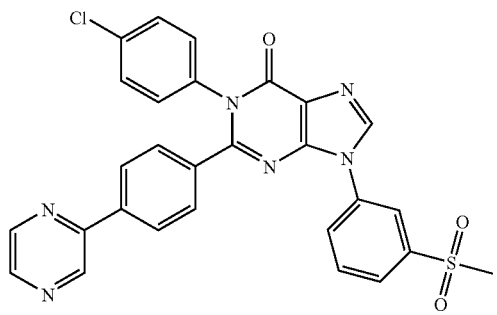 [SMILES: CS(=O)(=O)c1cccc(-n2cnc3c(=O)n(-c4ccc(Cl)cc4)c(-c4ccc(-c5cnccn5)cc4)nc32)c1]

A solution of 1-(4-chloro-phenyl)-9-(3-methanesulfonyl-phenyl)-2-[4-(4,4,5,5-tetramethyl-[1,3,2]dioxaborolan-2-yl)-phenyl]-1,9-dihydro-purin-6-one (prepared as described in example 38, 0.75 g, 1.2 mmol) in N,N-dimethylformamide (20 mL) is degassed with argon for 0.5 h. Then 2-iodopyrazine (0.38 g, 1.86 mmol), cesium carbonate (0.81 g, 2.4 mmol), Pd(dppf)$_2$Cl$_2$ (0.09 g, 0.12 mmol) is added and the resulted mixture is degassed with argon for 0.5 h. The reaction mixture is then heated at 100° C. for 4 h. The reaction mixture is cooled to rt and diluted with water and extracted with ethyl acetate (3×). The combined organic layer is washed with brine, dried over Na$_2$SO$_4$, concentrated, and purified by column chromatography to afford 1-(4-chloro-phenyl)-9-(3-methanesulfonyl-phenyl)-2-(4-pyrazin-2-yl-phenyl)-1,9-dihydro-purin-6-one. $^1$H NMR (DMSO-d$_6$, 400 MHz) δ 9.24 (m, 1H), 8.77 (s, 1H), 8.70 (s, 1H), 8.62 (s, 1H), 8.45 (s, 1H), 8.25 (d, 1H), 8.04 (m, 3H), 7.90 (m, 1H), 7.54 (m, 2H), 7.43 (m, 4H), 3.3 (s, 3H); LC-MS calculated for $C_{28}H_{19}ClN_6O_3S$ (M+H$^+$) 555.1, found 555.0.

Example 47

3-[5-(4-Chloro-phenyl)-4-oxo-6-(4-pyrazin-2-yl-phenyl)-4,5-dihydro-pyrazolo[3,4-d]pyrimidin-1-yl]-benzonitrile

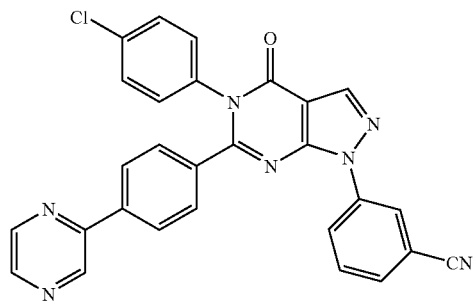 [SMILES: N#Cc1cccc(-n2ncc3c(=O)n(-c4ccc(Cl)cc4)c(-c4ccc(-c5cnccn5)cc4)nc32)c1]

A solution of 3-{5-(4-chloro-phenyl)-4-oxo-6-[4-(4,4,5,5-tetramethyl-[1,3,2]-dioxaborolan-2-yl)-phenyl]-4,5-dihydro-pyrazolo[3,4-d]pyrimidin-1-yl}-benzonitrile (prepared as described in example 28, 3.6 g, 6.54 mmol) in N,N-dimethylformamide (70 mL) is degassed with argon for 0.5 h. Then 2-iodopyrazine (2.0 g, 9.82 mmol), cesium carbonate (4.2 g, 13.09 mmol), Pd(dppf)$_2$Cl$_2$ (0.53 g, 0.654 mmol) is added and the resulted mixture is degassed with argon for 0.5 h The reaction mixture is then heated at 100° C. for 1.5 h. The reaction mixture is cooled to rt and diluted with water and extracted with ethyl acetate (3×). The combined organic layer is washed with brine, dried over Na$_2$SO$_4$, concentrated, and purified by column chromatography to afford 3-[5-(4-chloro-phenyl)-4-oxo-6-(4-pyrazin-2-yl-phenyl)-4,5-dihydro-pyrazolo[3,4-d]pyrimidin-1-yl]-benzonitrile. $^1$H NMR (DMSO-d$_6$, 400 MHz) δ 9.25 (s, 1H), 8.71 (m, 1H), 8.62 (m, 2H), 8.51 (m, 2H), 8.08 (d, 2H), 7.90 (m, 1H), 7.88 (m, 1H), 7.60 (d, 2H), 7.44 (m, 4H); LC-MS calculated for $C_{28}H_{16}ClN_7O$ (M+H$^+$) 502.1, found 502.0.

Example 48

3-[2-[4-(6-Amino-pyridin-3-yl)-phenyl]-1-(4-chloro-phenyl)-6-oxo-1,6-dihydro-purin-9-yl]-benzamidine

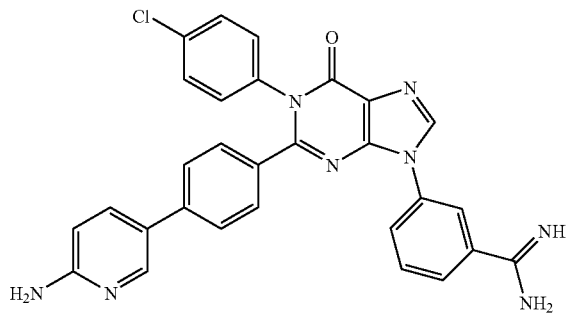 [SMILES: N=C(N)c1cccc(-n2cnc3c(=O)n(-c4ccc(Cl)cc4)c(-c4ccc(-c5ccc(N)nc5)cc4)nc32)c1]

To 3-[6-[4-(6-amino-pyridin-3-yl)-phenyl]-5-(4-chloro-phenyl)-4-oxo-4,5-dihydro-pyrazolo[3,4-d]pyrimidin-1-yl]-benzonitrile (prepared as described in example 44, 0.30 g, 0.58 mmol), methanol saturated with hydrogen chloride gas (15 mL) is added at 0° C. with stirring. The reaction mixture is allowed to reach rt and stirred there for 12 h. The reaction mixture is then concentrated to a dry residue. It is taken in dry methanol (15 mL) and ammonium carbonate (0.540 g, 3.48 mmol) is added. After stirring at rt for 24 h, the reaction mixture is concentrated and the residue obtained is purified by preparative HPLC to afford 3-[2-[4-(6-amino-pyridin-3-yl)-phenyl]-1-(4-chloro-phenyl)-6-oxo-1,6-dihydro-purin-9-yl]-benzamidine. $^1$H NMR (DMSO-d$_6$, 400 MHz) δ 8.65 (s, 1H), 8.28 (s, 1H), 8.22 (m, 1H), 8.15 (br, 2H), 7.96-8.03 (m, 2H), 7.67 (m, 2H), 7.59 (s, 1H), 7.45-7.50 (m, 9H), 6.47 (d, 1H), 6.15 (br, 1H); LC-MS calculated for $C_{29}H_{21}ClN_8O$ (M+H$^+$) 533.2, found 534.0.

Example 49

N-(3-(5-(4-chlorophenyl)-4-oxo-6-(4-(pyrimidin-2-yl)phenyl)-4,5-dihydro-1H-pyrazolo[3,4-d]pyrimidin-1-yl)phenyl)methanesulfonamide

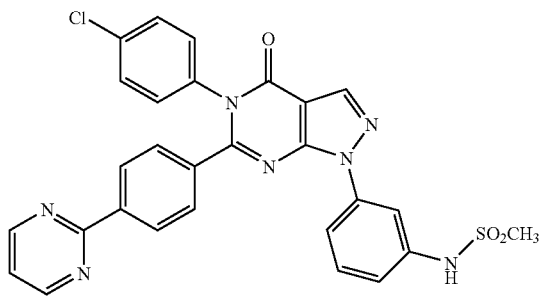 [SMILES: CS(=O)(=O)Nc1cccc(-n2ncc3c(=O)n(-c4ccc(Cl)cc4)c(-c4ccc(-c5ncccn5)cc4)nc32)c1]

A solution of N-(3-{5-(4-chloro-phenyl)-4-oxo-6-[4-(4,4,5,5-tetramethyl-[1,3,2]dioxa-borolan-2-yl)phenyl]-4,5-dihydro-pyrazolo[3,4-d]pyrimidin-1-yl}-phenyl)-methane sulfonamide (prepared as described in example 35, 0.45 g, 0.73 mmol) in N,N-dimethylformamide (15 mL) is degassed with argon for 0.5 h. Then 2-bromopyrimidine (0.173 g, 1.09 mmol), cesium carbonate (0.475 g, 1.46 mmol), Pd(dppf)$_2$Cl$_2$ (0.026 g, 0.036 mmol) are added and the resulting solution is degassed with argon for 0.5 h. The reaction mixture is then heated at 100° C. for 3 h. The reaction mixture is cooled to rt and diluted with water and extracted with ethyl acetate (3×). The combined organic layer is washed with brine, dried over Na$_2$SO$_4$, concentrated, and purified by column chromatography to afford N-{3-[5-(4-chloro-phenyl)-4-oxo-6-(4-pyrimidin-2-yl-phenyl)-4,5-dihydro-pyrazolo[3,4-d]pyrimidin-1-yl]-phenyl}-methane sulfonamide. $^1$H NMR (DMSO-d$_6$, 400 MHz) δ 10.13 (br, 1H), 8.91 (d, 2H), 8.57 (s, 1H), 8.25 (d, 2H), 8.05 (m, 1H), 7.83 (m, 1H), 7.58 (d, 2H), 7.45 (m, 6H), 7.17 (dd, 1H), 3.01 (s, 3H); LC-MS calculated for $C_{28}H_{20}ClN_7O_3S$ (M+H$^+$) 570.1, found 569.9 (M+H$^+$).

Example 50

N-{3-[5-(4-Chloro-phenyl)-4-oxo-6-(4-pyrimidin-5-yl-phenyl)-4,5-dihydro-pyrazolo[3,4-d]pyrimidin-1-yl]-phenyl}-methane sulfonamide

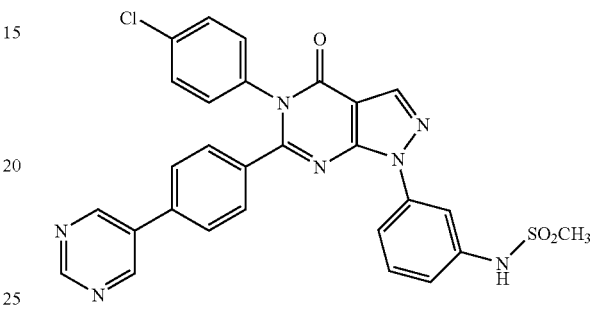

A solution of N-(3-{5-(4-chloro-phenyl)-4-oxo-6-[4-(4,4,5,5-tetramethyl-[1,3,2]dioxa-borolan-2-yl)phenyl]-4,5-dihydro-pyrazolo[3,4-d]pyrimidin-1-yl}-phenyl)-methane sulfonamide (prepared as described in example 35, 0.40 g, 0.65 mmol) in N,N-dimethylformamide (15 mL) is degassed with argon for 0.5 h. Then 5-bromopyrimidine (0.154 g, 0.97 mmol), cesium carbonate (0.421 g, 1.29 mmol), Pd(dppf)$_2$Cl$_2$ (0.023 g, 0.032 mmol) are added and the resulting solution is degassed with argon for 0.5 h. The reaction mixture is then heated at 100° C. for 3 h. The reaction mixture is cooled to rt and diluted with water and extracted with ethyl acetate (3×). The combined organic layer is washed with brine, dried over Na$_2$SO$_4$, concentrated, and purified by column chromatography to afford N-{3-[5-(4-chloro-phenyl)-4-oxo-6-(4-pyrimidin-5-yl-phenyl)-4,5-dihydro-pyrazolo[3,4-d]pyrimidin-1-yl]-phenyl}-methane sulfonamide. $^1$H NMR (DMSO-d$_6$, 400 MHz) δ 10.13 (br, 1H), 9.18 (s, 1H), 9.15 (s, 2H), 8.52 (s, 1H), 8.05 (m, 1H), 7.80 (m, 3H), 7.60 (d, 2H), 7.45 (m, 5H), 7.17 (dd, 1H), 3.02 (s, 3H); LC-MS calculated for $C_{28}H_{20}ClN7O_3S$ (M+H$^+$) 570.1, found 570.0.

Example 51

5-(4-chlorophenyl)-1-(3-methylsulfonyl)phenyl)-6-(4-(pyrazin-2-yl)phenyl)-1H-pyrazolo[3,4-d]pyrimidin-4(5H)-one

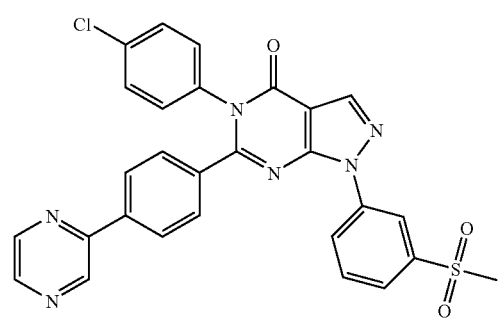

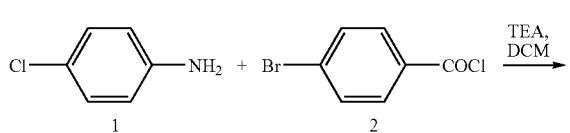

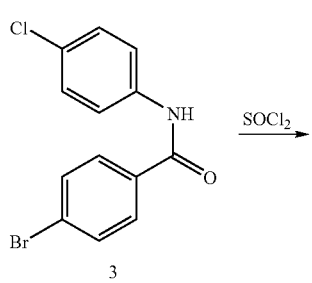

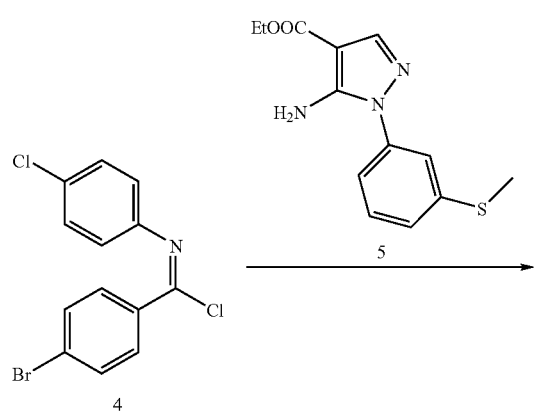

4-Bromo-N-(4-chloro-phenyl)-benzimidoyl chloride (4) is prepared by heating 4-bromo-N-(4-chloro-phenyl)-benzamide (3, 49.3 g, 158 mmol) and thionyl chloride (250 mL) for 1 h. The clear solution is concentrated and the residue obtained is coevaporated with toluene (100 mL). To the residue a solution of 5-amino-1-(3-methylsulfanyl-phenyl)-1H-pyrazole-4-carboxylic acid ethyl ester (5, 20.0 g, 72.1 mmol) in dry chloroform (100 mL) is added and the resulting mixture is concentrated to a dry residue. It is then heated to 170° C. without solvent for 6 h. The crude product obtained is purified by column chromatography (6).

5-Amino-1-(3-methylsulfanyl-phenyl)-1H-pyrazole-4-carboxylic acid ethyl ester (5) used above is prepared as described below.

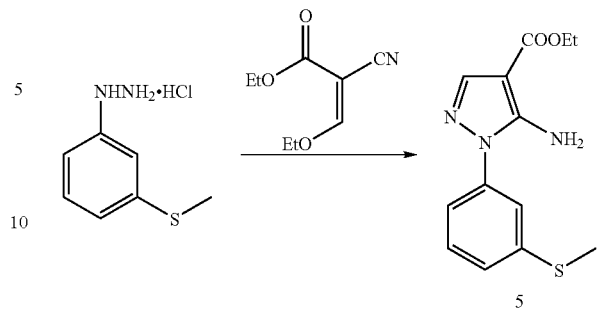

To a stirred solution of (3-methylsulfanyl-phenyl)-hydrazine hydrochloride (27.0 g, 141 mmol) in absolute ethanol (800 mL), sodium hydroxide (56.6 g, 1415 mmol) is added and the reaction mixture is stirred for 0.5 h. To the resulting mixture is added ethyl (ethoxymethylene) cyanoacetate (23.94 g, 141.5 mmol) and heated to 80° C. for 2 h. The reaction mixture is concentrated and the residue is taken in ethyl acetate, washed well with water. After washing with saturated brine solution, the organic layer is dried ($Na_2SO_4$) and concentrated to afford the crude product. The product is purified by column chromatography over silica gel (60-120 mesh) using ethyl acetate—pet ether solvent mixture as eluent.

4-Bromo-N-(4-chloro-phenyl)-benzamide (3) used is prepared by the following procedure. To a solution of 4-chloroaniline (1, 66.0 g, 516 mmol) and 4-bromobenzoyl chloride (2, 109.0 g, 496.6 mmol) in dichloromethane (1200 mL) is added triethyl amine (83.2 mL, 596 mmol). The reaction mixture is then poured into 0.05 N sodium hydroxide solution and the resulted suspension is stirred at rt for 1 h. The solid formed is filtered and washed well with water. It is dried in vacuum and used for the next step.

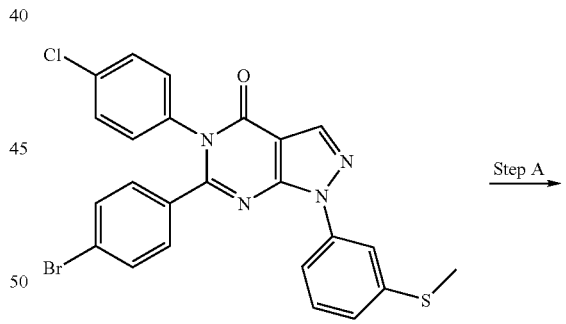

1H), 8.63 (m, 1H), 8.61 (m, 1H), 8.55 (m, 1H), 8.09 (m, 2H), 7.95 (m, 1H), 7.88 (m, 1H), 7.62 (m, 2H), 7.45 (m, 4H), 3.30 (s, 3H); LC-MS calculated for $C_{28}H_{19}ClN_6O_3S$ (M+H$^+$) 555.1, found 555.0.

Example 52

3-[5-(4-Chloro-phenyl)-4-oxo-6-(4-pyrazin-2-yl-phenyl)-4,5-dihydro-pyrazolo[3,4-d]pyrimidin-1-yl]-benzamidine

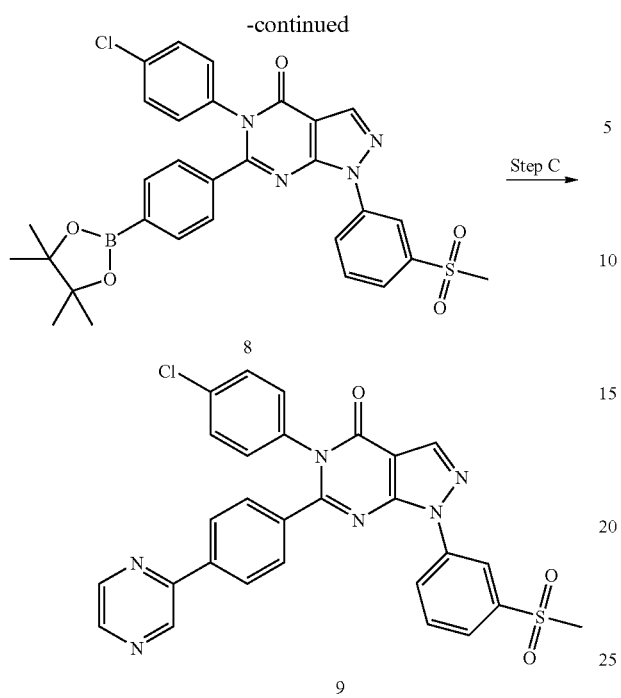

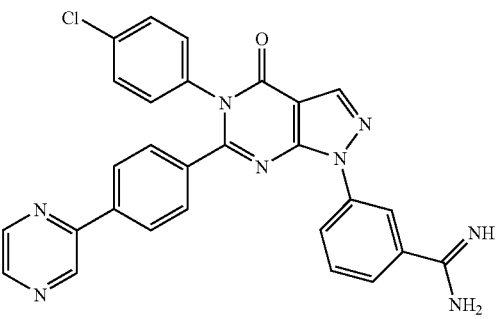 [SMILES: N=C(N)c1cccc(-n2ncc3c(=O)n(-c4ccc(Cl)cc4)c(-c4ccc(-c5cnccn5)cc4)nc32)c1]

At 0° C., 3-[5-(4-chloro-phenyl)-4-oxo-6-(4-pyrazin-2-yl-phenyl)-4,5-dihydro-pyrazolo[3,4-d]pyrimidin-1-yl]-benzonitrile (prepared as described in example 47, 0.65 g, 1.29 mmol) is added to methanol saturated with hydrogen chloride gas (20 mL) with stirring. The reaction mixture is allowed to reach rt and stirred there for 40 h. The reaction mixture is then concentrated to a dry residue (0.7 g). It is taken in dry methanol (40 mL) and ammonium carbonate (1.15 g, 7.36 mmol) is added. After stirring at rt for 40 h, the reaction mixture is concentrated and the residue obtained is purified by column chromatography to afford 3-[5-(4-chloro-phenyl)-4-oxo-6-(4-pyrazin-2-yl-phenyl)-4,5-dihydro-pyrazolo[3,4-d]pyrimidin-1-yl]-benzamidine. $^1$H NMR (DMSO-d$_6$, 400 MHz) δ 9.25 (s, 1H), 8.71 (s, 1H), 8.63 (m, 1H), 8.55 (m, 2H), 8.29 (dd, 1H), 8.16 (s, 1H), 8.07 (m, 1H), 7.90 (m, 1H), 7.67 (m, 1H), 7.62 (m, 2H), 7.52 (m, 1H), 7.44 (m, 4H); LC-MS calculated for $C_{28}H_{19}ClN_8O$ (M+H$^+$) 519.1, found 519.9.

Example 53

N-(3-(5-(4-chlorophenyl)-4-oxo-6-(4-(pyridazin-3-yl)phenyl)-4,5-dihydro-1H-pyrazolo[3,4-d]pyrimidin-1-yl)phenyl)methanesulfonamide

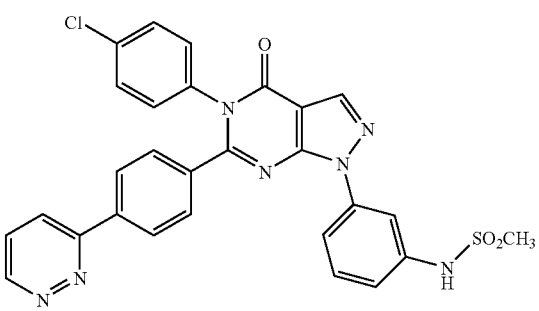 [SMILES: CS(=O)(=O)Nc1cccc(-n2ncc3c(=O)n(-c4ccc(Cl)cc4)c(-c4ccc(-c5cccnn5)cc4)nc32)c1]

Step A: To a stirred solution of 6-(4-bromo-phenyl)-5-(4-chloro-phenyl)-1-(3-methylsulfanyl-phenyl)-1,5-dihydro-pyrazolo[3,4-d]pyrimidin-4-one (6, 20.0 g, 38.2 mmol) in methanol (150 mL), dichloromethane (400 mL), magnesium monoperoxy phthalate hexahydrate (30.2 g, 61.1 mmol) is added. The resulting solution is stirred at rt for 18 h. The reaction is quenched with the addition of saturated solution of sodium bicarbonate, and extracted with dichloromethane. The organic layer is dried over Na$_2$SO$_4$, concentrated. The crude product is purified by column chromatography to afford methyl sulfone (7).

Step B: A solution of methyl sulfone (7, 16 g, 28.78 mmol) in N,N-dimethylformamide (150 mL) is taken in the round bottomed flask and is degassed with argon for 0.5 h. To the resulting mixture is added bis(pinacolato)diboron (8.7 g, 34.5 mmol), Pd(dppf)$_2$Cl$_2$ (2.1 g, 2.8 mmol), potassium acetate (8.5 g, 86 mmol) and the mixture is degassed with argon for 0.5 h. The reaction mixture is then heated at 80° C. for 2 h. The reaction mixture is cooled to rt and diluted with water and the compound is extracted with ethyl acetate (3×). The combined organic layer is washed with brine, dried over Na$_2$SO$_4$, concentrated, and purified by column chromatography to provide 5-(4-chloro-phenyl)-1-(3-methane-sulfonyl-phenyl)-6-[4-(4,4,5,5-tetramethyl-[1,3,2]dioxaborolan-2-yl)-phenyl]-1,5-dihydro-pyrazolo[3,4-d]pyrimidin-4-one (8).

Step C: A solution of 5-(4-chloro-phenyl)-1-(3-methane-sulfonyl-phenyl)-6-[4-(4,4,5,5-tetramethyl-[1,3,2]dioxaborolan-2-yl)-phenyl]-1,5-dihydro-pyrazolo[3,4-d]-pyrimidin-4-one (8, 0.5 g, 0.829 mmol) in N,N-dimethylformamide (20 mL) is degassed with argon for 0.5 h. Then 2-iodopyrazine (0.26 g, 1.2 mmol), cesium carbonate (0.54 g, 1.7 mmol), Pd(dppf)$_2$Cl$_2$ (0.06 g, 0.08 mmol) is added and the resulted mixture is degassed with argon for 0.5 h. The reaction mixture is then heated at 100° C. for 3 h. The reaction mixture is cooled to rt and diluted with water and extracted with ethyl acetate (3×). The combined organic layer is washed with brine, dried over Na$_2$SO$_4$, concentrated, and purified by preparative HPLC to afford 5-(4-chloro-phenyl)-1-(3-methanesulfonyl-phenyl)-6-(4-pyrazin-2-yl-phenyl)-1,5-dihydro-pyrazolo[3,4-d]pyrimidin-4-one (9). $^1$H NMR (DMSO-d$_6$, 400 MHz) δ 9.25 (s, 1H), 8.71 (m, 1H), 8.68 (m, A solution of N-(3-{5-(4-chloro-phenyl)-4-oxo-6-[4-(4,4,5,5-tetramethyl-[1,3,2]dioxaborolan-2-yl)phenyl]-4,5-dihydro-pyrazolo[3,4-d]pyrimidin-1-yl}-phenyl)-methane sulfonamide (prepared as described in example 35, 0.50 g, 0.81 mmol) in N,N-dimethylformamide (20 mL) is degassed with argon for 0.5 h. Then 2-iodopyridazine (0.25 g, 1.2 mmol), cesium carbonate (0.527 g, 1.61 mmol), Pd(dppf)$_2$Cl$_2$ (0.06 g, 0.08 mmol) are added and the resulting solution is degassed with argon for 0.5 h. The reaction mixture is then heated at 100° C. for 3 h. The reaction mixture is cooled to rt and diluted with water and extracted with ethyl acetate (3×). The combined organic layer is washed with brine, dried over Na$_2$SO$_4$, concentrated, and purified by column chromatography to afford N-{3-[5-(4-chloro-phenyl)-4-oxo-6-(4-pyridazin-3-yl-phenyl)-4,5-dihydro-pyrazolo[3,4-d]pyrimidin-1-yl]-phenyl}-methane sulfonamide (0.155 g, 34% yield). $^1$H NMR (DMSO-d$_6$, 400 MHz) δ 10.15 (br, 1H), 9.22 (m, 1H), 8.52 (s, 1H), 8.22 (d, 1H), 8.06 (m, 3H), 7.83 (m, 1H), 7.81 (m, 1H), 7.62 (m, 2H), 7.52 (m, 1H), 7.42-7.48 (m, 4H), 7.20 (m, 1H), 3.02 (s, 3H); LC-MS calculated for C$_{28}$H$_{20}$ClN$_7$O$_3$S (M+H$^+$) 570.1, found 569.9.

Example 54

N-{3-[1-(4-Chloro-phenyl)-6-oxo-2-(4-pyrimidin-5-yl-phenyl)-1,6-dihydro-purin-9-yl]-phenyl}-methane sulfonamide

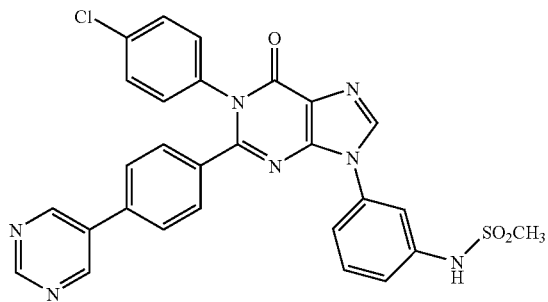 [SMILES: CS(=O)(=O)Nc1cccc(-n2cnc3c(=O)n(-c4ccc(Cl)cc4)c(-c4ccc(-c5cncnc5)cc4)nc32)c1]

A solution of N-(3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-phenyl)-methane sulfonamide (prepared as described in example 26, 0.500 g, 0.809 mmol) in N,N-dimethylformamide (20 mL) is degassed with argon for 0.5 h. Then 5-bromopyrimidine (0.195 g, 1.21 mmol), cesium carbonate (0.527 g, 1.61 mmol), Pd(dppf)$_2$Cl$_2$ (0.059 g, 0.08 mmol) is added and the resulted mixture is degassed with argon for 0.5 h. The reaction mixture is heated to 100° C. for 3 h. The reaction mixture is poured into water and extracted with ethyl acetate (3×). The combined organic layer is washed with brine, dried over Na$_2$SO$_4$, concentrated, and purified by column chromatography to afford N-{3-[1-(4-chloro-phenyl)-6-oxo-2-(4-pyrimidin-5-yl-phenyl)-1,6-dihydro-purin-9-yl]-phenyl}-methane sulfonamide. $^1$H NMR (DMSO-d$_6$, 400 MHz) δ 10.2 (s, 1H), 9.17 (s, 1H), 9.13 (m, 2H), 8.62 (s, 1H), 7.75 (m, 3H), 7.56 (m, 3H), 7.43-7.50 (m, 5H), 7.25 (d, 1H), 3.05 (s, 3H); LC-MS calculated for C$_{28}$H$_{20}$ClN$_7$O$_3$S (M+H$^+$) 570.1, found 569.9.

Example 55

N-(3-(5-(4-chlorophenyl)-4-oxo-6-(4-(pyrazin-2-yl)phenyl)-4,5-dihydro-1H-pyrazolo[3,4-d]pyrimidin-1-yl)phenyl)methanesulfonamide

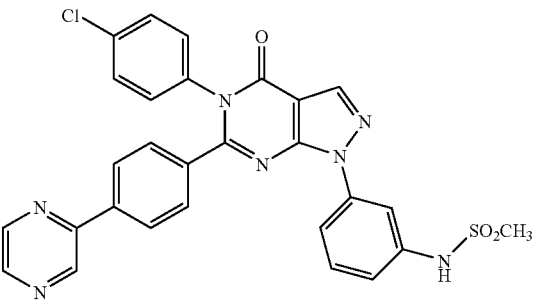 [SMILES: CS(=O)(=O)Nc1cccc(-n2ncc3c(=O)n(-c4ccc(Cl)cc4)c(-c4ccc(-c5cnccn5)cc4)nc32)c1]

A solution of N-(3-{5-(4-chloro-phenyl)-4-oxo-6-[4-(4,4,5,5-tetramethyl-[1,3,2]dioxa-borolan-2-yl)phenyl]-4,5-dihydro-pyrazolo[3,4-d]pyrimidin-1-yl}-phenyl)-methane sulfonamide (prepared as described in example 35, 0.50 g, 0.81 mmol) in N,N-dimethylformamide (20 mL) is degassed with argon for 0.5 h. Then 2-iodopyrazine (0.25 g, 1.21 mmol), cesium carbonate (0.527 g, 1.61 mmol), Pd(dppf)$_2$Cl$_2$ (0.06 g, 0.082 mmol) are added and the resulting solution is degassed with argon for 0.5 h. The reaction mixture is then heated at 100° C. for 3 h. The reaction mixture is cooled to rt and diluted with water and extracted with ethyl acetate (3×). The combined organic layer is washed with brine, dried over Na$_2$SO$_4$, concentrated, and purified by column chromatography to afford N-{3-[5-(4-chloro-phenyl)-4-oxo-6-(4-pyrazin-2-yl-phenyl)-4,5-dihydro-pyrazolo[3,4-d]pyrimidin-1-yl]-phenyl}-methane sulfonamide. $^1$H NMR (DMSO-d$_6$, 400 MHz) δ 10.15 (br, 1H), 9.26 (d, 1H), 8.71 (d, 1H), 8.62 (d, 1H), 8.52 (s, 1H), 8.06 (m, 3H), 7.82 (m, 1H), 7.60 (m, 2H), 7.52 (m, 1H), 7.40 (m, 4H), 7.18 (m, 1H), 3.02 (s, 3H); LC-MS calculated for C$_{28}$H$_{20}$ClN$_7$O$_3$S (M+H$^+$) 570.1, found 570.0.

Example 56

N-{3-[1-(4-Chloro-phenyl)-6-oxo-2-(4-pyridazin-3-yl-phenyl)-1,6-dihydro-purin-9-yl]-phenyl}-methanesulfonamide

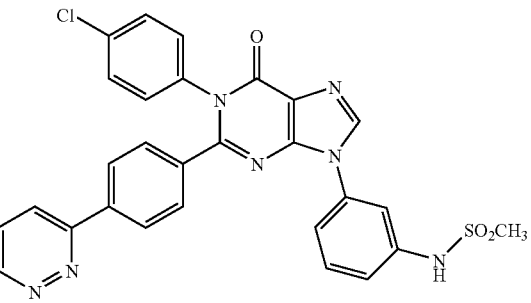

A solution of N-(3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-phenyl)-methanesulfonamide (prepared as described in example 26, 0.500 g, 0.809 mmol) in N,N- dimethylformamide (20 mL) is degassed with argon for 0.5 h. Then 2-iodopyridazine (0.250 g, 1.21 mmol), cesium carbonate (0.527 g, 1.61 mmol), Pd(dppf)$_2$Cl$_2$ (0.059 g, 0.08 mmol) is added and the resulted mixture is degassed with argon for 0.5 h. The reaction mixture is heated to reflux for 3 h. The reaction mixture is poured into with water and extracted with ethyl acetate (3×). The combined organic layer is washed with brine, dried over Na$_2$SO$_4$, concentrated, and purified by column chromatography to afford N-{3-[1-(4-chloro-phenyl)-6-oxo-2-(4-pyridazin-3-yl-phenyl)-1,6-dihydro-purin-9-yl]-phenyl}-methane sulfonamide. $^1$H NMR (DMSO-d$_6$, 400 MHz) δ 10.2 (br, 1H), 9.20 (m, 1H), 8.62 (m, 1H), 8.21 (d, 1H), 8.06 (m, 2H), 7.77 (m, 2H), 7.42-7.57 (m, 8H), 7.25 (d, 1H), 3.05 (s, 3H); LC-MS calculated for C$_{28}$H$_{20}$ClN$_7$O$_3$S (M+H$^+$) 570.1, found 570.0.

Example 57

3-(5-(4-chlorophenyl)-4-oxo-6-(4-(pyrazin-2-yl)phenyl)-4,5-dihydro-1H-pyrazolo[3,4-d]pyrimidin-1-yl)benzenesulfonamide

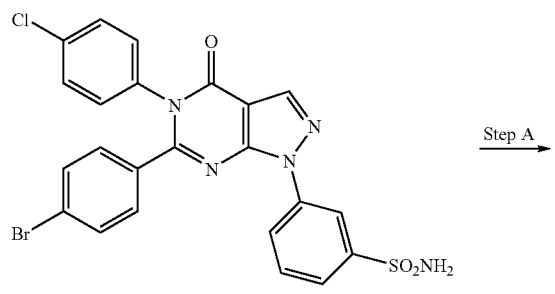

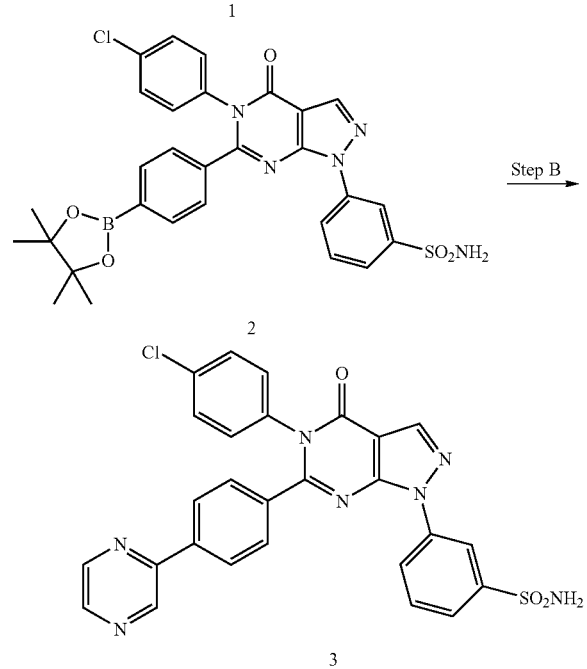

Step A: 3-[6-(4-bromo-phenyl)-5-(4-chloro-phenyl)-4-oxo-4,5-dihydro-pyrazolo[3,4-d]pyrimidin-1-yl]-benzene sulfonamide (1, prepared as described in example 6, 2.00 g, 3.59 mmol) in N,N-dimethylformamide (60 mL) is taken in the round bottomed flask and is degassed with argon for 0.5 h. To the resulting mixture is added bis(pinacolato)diboron (1.09 g, 4.31 mmol), Pd(dppf)$_2$Cl$_2$ (0.29 g, 0.36 mmol), potassium acetate (1.00 g, 10.8 mmol) and the mixture is degassed with argon for 0.5 h. The reaction mixture is then heated at 80° C. for 2 h. The reaction mixture is cooled to rt, diluted with water and extracted with ethyl acetate (3×). The combined organic layer is washed with brine, dried over Na$_2$SO$_4$, concentrated, and purified by column chromatography to provide 3-{5-(4-chloro-phenyl)-4-oxo-6-[4-(4,4,5,5-tetramethyl-[1,3,2]dioxaborolan-2-yl)-phenyl]-4,5-dihydro-pyrazolo[3,4-d]pyrimidin-1-yl}-benzene sulfonamide (2).

Step B: A solution of 3-{5-(4-chloro-phenyl)-4-oxo-6-[4-(4,4,5,5-tetramethyl-[1,3,2]-dioxa-borolan-2-yl)-phenyl]-4,5-dihydro-pyrazolo[3,4-d]pyrimidin-1-yl}-benzene sulfonamide (2, 0.650 g, 1.08 mmol) in N,N-dimethylformamide (10 mL) is degassed with argon for 0.5 h. Then 2-iodopyrazine (0.33 g, 1.616 mmol), cesium carbonate (0.701 g, 2.15 mmol), Pd(dppf)$_2$Cl$_2$ (0.087 g, 0.107 mmol) is added and the resulted mixture is degassed with argon for 0.5 h. The reaction mixture is then heated at 100° C. for 2.5 h. The reaction mixture is cooled to rt and diluted with water and extracted with ethyl acetate (3×). The combined organic layer is washed with brine, dried over Na$_2$SO$_4$, concentrated, and purified by preparative HPLC to afford 3-[5-(4-chloro-phenyl)-4-oxo-6-(4-pyrazin-2-yl-phenyl)-4,5-dihydro-pyrazolo[3,4-d]pyrimidin-1-yl]-benzene sulfonamide (3). $^1$H NMR (DMSO-d$_6$, 400 MHz) δ 9.25 (s, 1H), 8.71 (m, 1H), 8.63 (d, 1H), 8.58 (m, 2H), 8.45 (m, 1H), 8.07 (m, 2H), 7.80 (m, 2H), 7.59 (m, 4H), 7.45 (m, 4H); LC-MS calculated for C$_{27}$H$_{18}$ClN$_7$O$_3$S (M+H$^+$) 556.1, found 555.9.

Example 58

N-{3-[1-(4-Chloro-phenyl)-6-oxo-2-(4-pyrazin-2-yl-phenyl)-1,6-dihydro-purin-9-yl]-phenyl}-methane sulfonamide

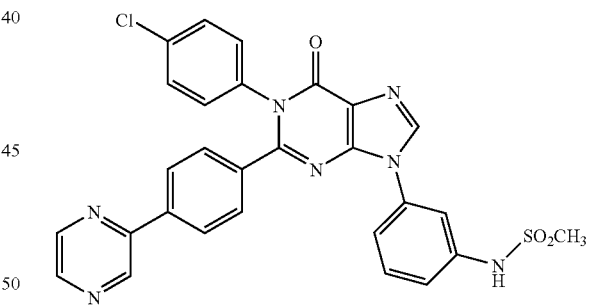

A solution of N-(3-{1-(4-chloro-phenyl)-6-oxo-2-[4-(4,4,5,5-tetramethyl-[1,3,2]dioxaborolan-2-yl)-phenyl]-1,6-dihydro-purin-9-yl}-phenyl)-methane sulfonamide (prepared as described in example 26, 0.5 g, 0.809 mmol) in N,N-dimethylformamide (20 mL) is degassed with argon for 0.5 h. Then 2-iodopyrazine (0.25 g, 1.21 mmol), cesium carbonate (0.527 g, 1.61 mmol), Pd(dppf)$_2$Cl$_2$ (0.059 g, 0.08 mmol) is added and the resulted mixture is degassed with argon for 0.5 h. The reaction mixture is stirred at rt for 18 h. The reaction mixture is poured into water and extracted with ethyl acetate (3×). The combined organic layer is washed with brine, dried over Na$_2$SO$_4$, concentrated, and purified by column chromatography to afford N-{3-[1-(4-chloro-phenyl)-6-oxo-2-(4-pyrazin-2-yl-phenyl)-1,6-dihydro-purin-9-yl]-phenyl}-methane sulfonamide. $^1$H NMR (DMSO-d$_6$, 400 MHz) δ 9.25

(s, 1H), 8.69 (m, 1H), 8.62 (m, 2H), 8.03 (m, 2H), 7.74 (s, 1H), 7.46-7.56 (m, 9H), 7.25 (m, 1H), 3.05 (s, 3H); LC-MS calculated for $C_{28}H_{20}ClN_7O_3S$ (M+H$^+$) 570.1, found 569.9.

Example 59

3-[1-(4-Chloro-phenyl)-6-oxo-2-(4-pyrazin-2-yl-phenyl)-1,6-dihydro-purin-9-yl]-benzene sulfonamide

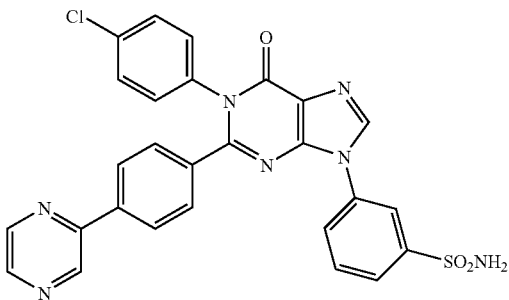 [SMILES: NS(=O)(=O)c1cccc(-n2cnc3c(=O)n(-c4ccc(Cl)cc4)c(-c4ccc(-c5cnccn5)cc4)nc32)c1]

A solution of 3-{5-(4-chloro-phenyl)-4-oxo-6-[4-(4,4,5,5-tetramethyl-[1,3,2]dioxaborolan-2-yl)-phenyl]-4,5-dihydro-pyrazolo[3,4-d]pyrimidin-1-yl}-benzene sulfonamide (prepared as described in example 25, 0.500 g, 0.82 mmol) in N,N-dimethylformamide (20 mL) is degassed with argon for 0.5 h. Then 2-iodopyrazine (0.250 g, 1.24 mmol), cesium carbonate (0.530 g, 1.65 mmol), Pd(dppf)$_2$Cl$_2$ (0.06 g, 0.08 mmol) is added and the resulted mixture is degassed with argon for 0.5 h. The reaction mixture is then heated at 50° C. for 12 h. The reaction mixture is cooled to rt and diluted with water and extracted with ethyl acetate (3×). The combined organic layer is washed with brine, dried over Na$_2$SO$_4$, concentrated, and purified by column chromatography over silica gel (60-120 mesh) to afford 3-[1-(4-chloro-phenyl)-6-oxo-2-(4-pyrazin-2-yl-phenyl)-1,6-dihydro-purin-9-yl]-benzene sulfonamide. $^1$H NMR (DMSO-d$_6$, 400 MHz) δ 9.24 (m, 1H), 8.69 (m, 1H), 8.63 (m, 1H), 8.30 (m, 1H), 8.02-8.08 (m, 2H), 7.94 (m, 1H), 7.82 (m, 1H), 7.43-7.58 (m, 8H), 7.15 (br, 2H); LC-MS calculated for $C_{27}H_{18}ClN_7O_3S$ (M+H$^+$) 556.1, found 555.9.

Example 60

5-(4-Chloro-phenyl)-1-(3-methanesulfonyl-phenyl)-6-(4-pyrimidin-5-yl-phenyl)-1,5-dihydro-pyrazolo[3,4-d]pyrimidin-4-one

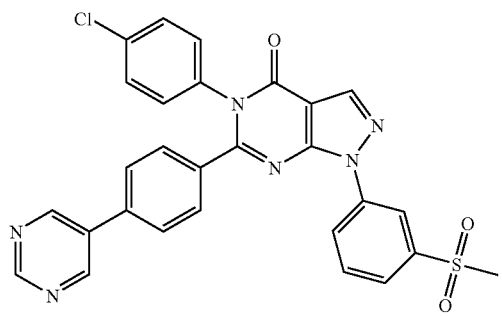 [SMILES: CS(=O)(=O)c1cccc(-n2ncc3c(=O)n(-c4ccc(Cl)cc4)c(-c4ccc(-c5cncnc5)cc4)nc32)c1]

A solution of 5-(4-chloro-phenyl)-1-(3-methanesulfonyl-phenyl)-6-[4-(4,4,5,5-tetramethyl-[1,3,2]dioxaborolan-2-yl)-phenyl]-1,5-dihydro-pyrazolo[3,4-d]-pyrimidin-4-one (prepared as described in example 51, 0.500 g, 0.829 mmol) in N,N-dimethylformamide (20 mL) is degassed with argon for 0.5 h. Then 5-bromopyrimidine (0.200 g, 1.24 mmol), cesium carbonate (0.540 g, 1.66 mmol), Pd(dppf)$_2$Cl$_2$ (0.060 g, 0.082 mmol) is added and the resulted mixture is degassed with argon for 0.5 h. The reaction mixture is then heated at 100° C. for 2 h. The reaction mixture is cooled to rt and diluted with water and extracted with ethyl acetate (3×). The combined organic layer is washed with brine, dried over Na$_2$SO$_4$, concentrated, and purified by column chromatography over silica gel (60-120 mesh) to afford 5-(4-chloro-phenyl)-1-(3-methanesulfonyl-phenyl)-6-(4-pyrimidin-5-yl-phenyl)-1,5-dihydro-pyrazolo[3,4-d]pyrimidin-4-one. $^1$H NMR (DMSO-d$_6$, 400 MHz) δ 9.18 (s, 1H), 9.15 (m, 2H), 8.67 (m, 1H), 8.61 (m, 1H), 8.55 (m, 1H), 7.96 (m, 1H), 7.90 (m, 1H), 7.82 (m, 2H), 7.61 (m, 2H), 7.46 (m, 4H), 3.30 (s, 3H); LC-MS calculated for $C_{28}H_{19}ClN_6O_3S$ (M+H$^+$) 555.1, found 554.9.

Example 61

5-(4-Chloro-phenyl)-1-(3-methanesulfonyl-phenyl)-6-(4-pyrimidin-2-yl-phenyl)-1,5-dihydro-pyrazolo[3,4-d]pyrimidin-4-one

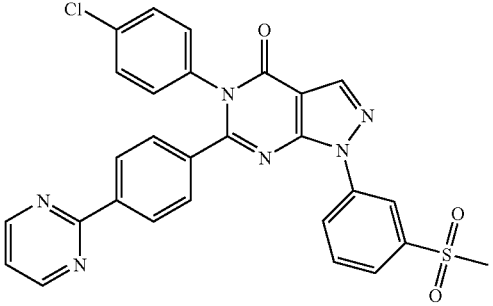 [SMILES: CS(=O)(=O)c1cccc(-n2ncc3c(=O)n(-c4ccc(Cl)cc4)c(-c4ccc(-c5ncccn5)cc4)nc32)c1]

A solution of 5-(4-chloro-phenyl)-1-(3-methanesulfonyl-phenyl)-6-[4-(4,4,5,5-tetramethyl-[1,3,2]dioxaborolan-2-yl)-phenyl]-1,5-dihydro-pyrazolo[3,4-d]-pyrimidin-4-one (prepared as described in example 51, 0.500 g, 0.829 mmol) in N,N-dimethylformamide (30 mL) is degassed with argon for 0.5 h. Then 2-bromopyrimidine (0.197 g, 1.24 mmol), cesium carbonate (0.540 g, 1.66 mmol), Pd(dppf)$_2$Cl$_2$ (0.06 g, 0.082 mmol) is added and the resulted mixture is degassed with argon for 0.5 h. The reaction mixture is heated to 100° C. for 2 h. The reaction mixture is diluted with water and extracted with ethyl acetate (3×). The combined organic layer is washed with brine, dried over Na$_2$SO$_4$, concentrated, and purified by column chromatography over silica gel (60-120 mesh) to afford 5-(4-chloro-phenyl)-1-(3-methanesulfonyl-phenyl)-6-(4-pyrimidin-2-yl-phenyl)-1,5-dihydro-pyrazolo[3,4-d]pyrimidin-4-one. $^1$H NMR (CDCl$_3$, 400 MHz) δ 8.89 (m, 3H), 8.60 (m, 1H), 8.46 (m, 2H), 8.38 (s, 1H), 7.92-7.95 (m, 1H), 7.74 (m, 1H), 7.54 (m, 2H), 7.33-7.36 (m, 3H), 7.13-7.17 (m, 2H); LC-MS calculated for $C_{28}H_{19}ClN_6O_3S$ (M+H$^+$) 555.1, found 554.9.

Example 62

3-[6-[4-(5-Amino-pyridin-2-yl)-phenyl]-5-(4-chloro-phenyl)-4-oxo-4,5-dihydro-pyrazolo[3,4-d]pyrimidin-1-yl]-benzene sulfonamide

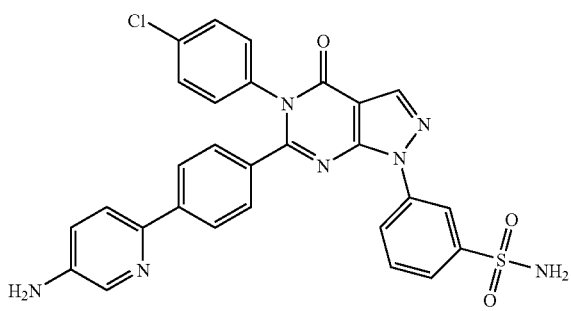 [SMILES: Nc1ccc(-c2ccc(-c3nc4c(cnn4-c4cccc(S(N)(=O)=O)c4)c(=O)n3-c3ccc(Cl)cc3)cc2)nc1]

A mixture of 3-[6-(4-bromo-phenyl)-5-(4-chloro-phenyl)-4-oxo-4,5-dihydro-pyrazolo[3,4-d]pyrimidin-1-yl]-benzene sulfonamide (prepared as described in example 6, 10.00 g, 17.95 mmol), hexane-2,5-dione (6.14 g, 53.9 mmol), and p-toluenesulfonic acid monohydrate (1.000 g, 5.257 mmol) in dry toluene (250 mL) is heated to reflux in a Dean-Stark apparatus for 18 h. The reaction mixture is concentrated and the residue obtained is stirred in ethyl acetate and filtered. About 7.1 g of starting material is recovered. Concentration of the filtrate afforded the crude product. It is then purified by column chromatography (silica gel, 60-120 mesh) to afford the 6-(4-bromo-phenyl)-5-(4-chloro-phenyl)-1-[3-(2,5-dimethyl-pyrrole-1-sulfonyl)-phenyl]-1,5-dihydro-pyrazolo[3,4-d]pyrimidin-4-one.

A solution of 6-(4-bromo-phenyl)-5-(4-chloro-phenyl)-1-[3-(2,5-dimethyl-pyrrole-1-sulfonyl)-phenyl]-1,5-dihydro-pyrazolo[3,4-d]pyrimidin-4-one (1.50 g, 2.36 mmol) in N,N-dimethylformamide (15 mL) in the round bottomed flask is degassed with argon for 0.5 h. To the resulting mixture is added bis(pinacolato)diboron (0.72 g, 2.83 mmol), Pd(dppf)$_2$Cl$_2$ (0.193 g, 0.236 mmol), potassium acetate (0.694 g, 7.08 mmol) and the mixture is degassed with argon for 0.5 h. The reaction mixture is then heated at 80° C. for 2 h. The reaction mixture is cooled to rt, diluted with water and the extracted with ethyl acetate (3×). The combined organic layer is washed with brine, dried over Na$_2$SO$_4$, concentrated, and purified by column chromatography to provide 5-(4-chloro-phenyl)-1-[3-(2,5-dimethyl-pyrrole-1-sulfonyl)-phenyl]-6-[4-(4,4,5,5-tetramethyl-[1,3,2]dioxaborolan-2-yl)-phenyl]-1,5-dihydro-pyrazolo[3,4-d]pyrimidin-4-one.

A solution of 5-(4-chloro-phenyl)-1-[3-(2,5-dimethyl-pyrrole-1-sulfonyl)-phenyl]-6-[4-(4,4,5,5-tetramethyl-[1,3,2] dioxaborolan-2-yl)-phenyl]-1,5-dihydro-pyrazolo[3,4-d]pyrimidin-4-one (0.950 g, 1.393 mmol) in N,N-dimethylformamide (40 mL) is degassed with argon for 0.5 h. Then 5-amino-2-bromopyridine (0.43 g, 2.507 mmol), cesium carbonate (0.907 g, 2.78 mmol), Pd(dppf)$_2$Cl$_2$ (0.122 g, 0.167 mmol) is added and the resultant mixture is degassed with argon for 0.5 h. The reaction mixture is then heated at 100° C. for 6 h. The reaction mixture is cooled to rt and diluted with water and extracted with ethyl acetate (3×). The combined organic layer is washed with brine, dried over Na$_2$SO$_4$, concentrated, and purified by column chromatography (silica gel 60-120 mesh) to afford 6-[4-(5-amino-pyridin-2-yl)-phenyl]-5-(4-chloro-phenyl)-1-[3-(2,5-dimethyl-pyrrole-1-sulfonyl)-phenyl]-1,5-dihydro-pyrazolo[3,4-d]pyrimidin-4-one.

A mixture of 6-[4-(5-amino-pyridin-2-yl)-phenyl]-5-(4-chloro-phenyl)-t-[3-(2,5-dimethyl-pyrrole-1-sulfonyl)-phenyl]-1,5-dihydro-pyrazolo[3,4-d]pyrimidin-4-one (0.410 g, 0.632 mmol), trifluoroacetic acid (4.5 mL) and water (1.5 mL) is heated to reflux for 3 h. The reaction mixture is concentrated to a residue. It is then taken in water, neutralized with triethyl amine and extracted with ethyl acetate (3×). The combined organic layer is washed with brine, dried over Na$_2$SO$_4$, concentrated, and purified by preparative HPLC chromatography to afford 3-[6-[4-(5-amino-pyridin-2-yl)-phenyl]-5-(4-chloro-phenyl)-4-oxo-4,5-dihydro-pyrazolo[3,4-d]pyrimidin-1-yl]-benzene sulfonamide. $^1$H NMR (CD$_3$OD, 400 MHz) δ 8.88 (s, 1H), 8.45 (d, 1H), 8.40 (s, 1H), 7.91-7.96 (m, 4H), 7.66-7.75 (m, 6H), 7.33-7.41 (m, 4H); LC-MS calculated for C$_{28}$H$_{20}$ClN$_7$O$_3$S (M+H$^+$) 570.1, found 570.0.

By repeating the procedures described in the above examples, using appropriate starting materials, the following compounds of Formula I, as identified in Table 1, are obtained.

TABLE 1

| Compound Number | Structure | Physical Data $^1$H NMR 400 MHz (CDCl$_3$) and/or MS (m/z) |
|---|---|---|
| 1 | ![structure] | $^1$H NMR (MeOD) δ (ppm) 8.30(d, 1H), 8.11-8.18(m, 4H), 7.59-7.64(m, 4H), 7.55(t, 1H), 7.32-7.43(m, 5H). HPLC-MS calculated C$_{26}$H$_{17}$ClN$_8$O (M + H$^+$): 493.1, found: 493.1 |

TABLE 1-continued

| Compound Number | Structure | Physical Data $^1$H NMR 400 MHz (CDCl$_3$) and/or MS (m/z) |
|---|---|---|
| 4 | 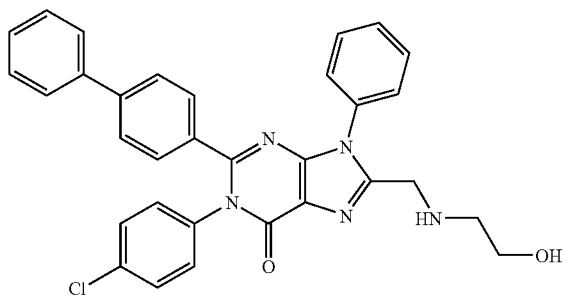 [SMILES: O=c1c2nc(CNCCO)n(-c3ccccc3)c2nc(-c2ccc(-c3ccccc3)cc2)n1-c1ccc(Cl)cc1] | HPLC-MS calculated C$_{32}$H$_{265}$ClN$_5$O$_2$ (M+ H$^+$): 548.2, found: 548.2 |
| 8 | 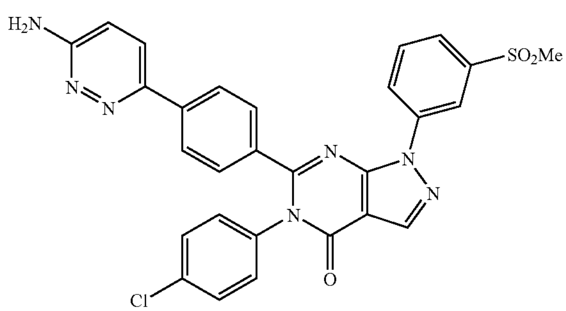 [SMILES: CS(=O)(=O)c1cccc(-n2ncc3c(=O)n(-c4ccc(Cl)cc4)c(-c4ccc(-c5ccc(N)nn5)cc4)nc32)c1] | $^1$H NMR (CDCl$_3$) δ (ppm) 8.97(s, 1H), 8.51 (d, 1H), 8.39(s, 1H), 8.01 (d, 1H), 7.93 (d, 1H), 7.81 (d, 2H), 7.75 (t, 1H), 7.52 (d, 1H), 7.40 (d, 1H), 7.35 (d, 2H), 7.12 (d, 2H), 3.13 (s, 1H). HPLC-MS calculated C$_{28}$H$_{20}$ClN$_7$O$_3$S (M + H$^+$): 570.1, found: 570.1 |
| 9 | 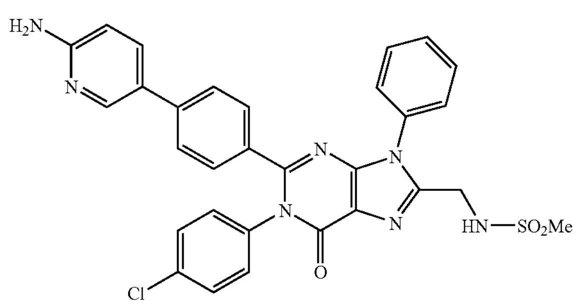 [SMILES: CS(=O)(=O)NCc1nc2c(=O)n(-c3ccc(Cl)cc3)c(-c3ccc(-c4ccc(N)nc4)cc3)nc2n1-c1ccccc1] | HPLC-MS calculated C$_{30}$H$_{24}$ClN$_7$O$_3$S (M + H$^+$): 598.1, found: 598.1 |
| 11 | 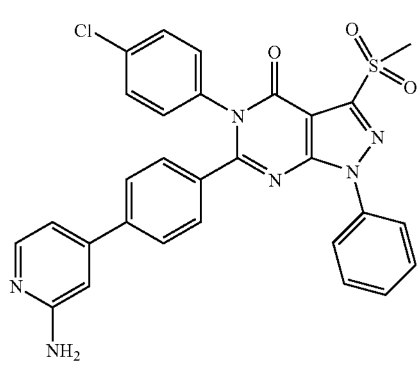 [SMILES: CS(=O)(=O)c1nn(-c2ccccc2)c2nc(-c3ccc(-c4ccnc(N)c4)cc3)n(-c3ccc(Cl)cc3)c(=O)c12] | HPLC-MS calculated for C$_{29}$H$_{21}$ClN$_6$O$_3$S (M + H$^+$) 569.1, found 569.1. |

TABLE 1-continued

| Compound Number | Structure | Physical Data<br>¹H NMR 400 MHz<br>(CDCl₃) and/or MS<br>(m/z) |
|---|---|---|
| 17 | 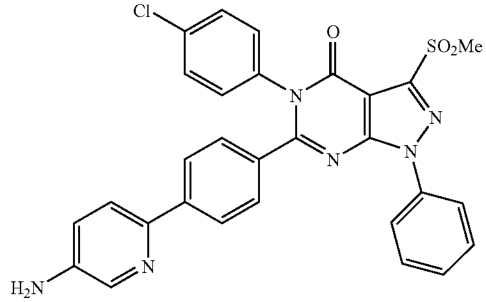 [SMILES: CS(=O)(=O)c1nn(-c2ccccc2)c2nc(-c3ccc(-c4ccc(N)cn4)cc3)n(-c3ccc(Cl)cc3)c(=O)c12] | ¹H NMR (CDCl₃, 400 MHz) δ 8.74 (d, 1H), 8.09 (d, 2H), 7.84 (d, 2H), 7.74 (d, 1H), 7.55 (m, 5H), 7.45 (t, 1H), 7.35 (d, 2H), 7.15 (d, 2H), 3.55 (s, 3H); HPLC-MS calculated for $C_{29}H_{21}ClN_6O_3S$ (M + H⁺) 569.1, found 569.1. |
| 18 | 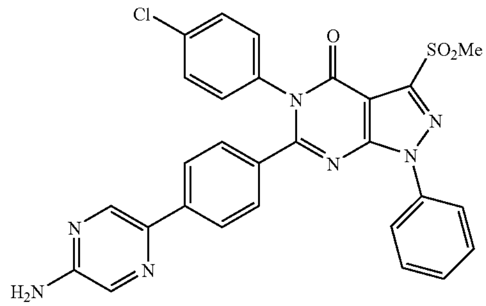 [SMILES: CS(=O)(=O)c1nn(-c2ccccc2)c2nc(-c3ccc(-c4cnc(N)cn4)cc3)n(-c3ccc(Cl)cc3)c(=O)c12] | HPLC-MS calculated for $C_{28}H_{20}ClN_7O_3S$ (M + H⁺) 570.1, found 570.1. |
| 21 | 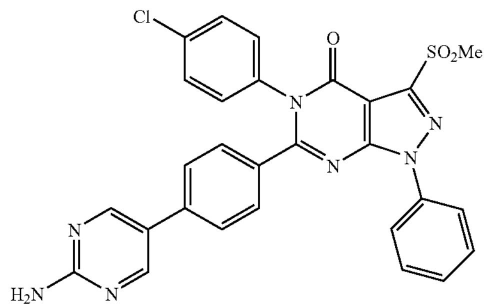 [SMILES: CS(=O)(=O)c1nn(-c2ccccc2)c2nc(-c3ccc(-c4cnc(N)nc4)cc3)n(-c3ccc(Cl)cc3)c(=O)c12] | HPLC-MS calculated for $C_{28}H_{20}ClN_7O_3S$ (M + H⁺) 570.1, found 570.1. |
| 22 | 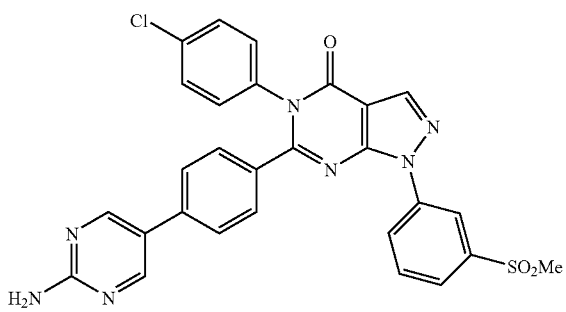 [SMILES: CS(=O)(=O)c1cccc(-n2ncc3c(=O)n(-c4ccc(Cl)cc4)c(-c4ccc(-c5cnc(N)nc5)cc4)nc32)c1] | ¹H NMR (CDCl₃, 400 MHz) δ 8.94 (s, 1H), 8.56 (d, 1H), 8.54 (s, 2H), 8.36 (s, 1H), 7.92 (d, 1H), 7.33 (t, 1H), 7.48 (d, 2H), 7.42 (d, 2H), 7.37 (d, 2H), 7.14 (d, 2H), 5.48 (br, 2H), 3.12 (s, 3H); HPLC-MS calculated for $C_{28}H_{20}ClN_7O_3S$ (M + H⁺) 570.1, found 570.1. |

CB1 Biological Assays

Homogenized membranes are prepared from CHO cell clones stably expressing a human cannabinoid receptor 1 (CB1) or human cannabinoid receptor 2 (CB2). Cells are grown and scrapped from 15 cm tissue culture plates, and then subsequently centrifuged down. Cells are washed once with cold PBS, and resuspended in ≤20 ml of Buffer A (20 mM HEPES, pH 7.4, 10 mM EDTA, EDTA-free complete protease inhibitor cocktail [1 tablet/25 ml]). The cell suspension is homogenized on ice, using a Polytron homogenizer at 25000 rpm at three intervals of 15 seconds each. The homogenate is first centrifuged at 2000 rpm on a tabletop low speed centrifuge for 10 minutes. The supernatant, after passing through a cell strainer, is then centrifuged at 50,000×g for 25 minutes at 4° C. The pellet is resuspended into buffer B (15% glycerol, 20 mM HEPES, pH 7.4, 0.1 mM EDTA, EDTA-free complete protease inhibitor cocktail [1 tablet/10 ml]). Protein concentration of the prep is determined using the BCA Protein Assay kit using BSA as standard. The membranes are aliquoted and kept frozen at −80° C.

[³H]-CP55940 ligand binding assay: Solutions of test compounds ranging from 100 μM to 0.01 nM are prepared in DMSO. The desired amount of membrane prep is diluted with ice-cold assay buffer (50 mM Tris-HCl, 2.5 mM EDTA, 5 mM MgCl$_2$, 0.05% BSA, pH 7.4) and vortexed well. 2 μl or less of compound is distributed into each well of a round-bottom 96-well polystyrene assay plate, followed by addition of 100 μl of diluted membranes (3-10 μg/well) and the mixture is kept on ice until the addition of hot CP55940 (final concentration of 0.5 nM). [³H]-CP55940 is diluted 1:6300 (v/v) with cold assay buffer and 100 μl is added into each well. The reaction is carried out at room temperature for 120 minutes before the membranes are harvested onto a PerkinElmer Unifilter GF/B-96 filter plate using a Packard Filtermate Harvester. After nine washes with wash buffer (50 mM Tris-HCl, 2.5 mM EDTA, 5 mM MgCl$_2$, 0.05% BSA, pH 7.), the filter is dried in a 37° C. oven for 30 minutes. MicroScint-20 is added and the plate sealed for scintillation counting on Top-Count. EC$_{50}$ values are obtained by fitting the data with the sigmoidal dose response curve-fitting tool of GraphPad Prism. Eight or twelve different concentrations are used to generate a concentration response curve (using three data points per concentration).

GTPγS binding assay: Solutions of test compounds ranging from 100 μM to 0.01 nM are prepared in DMSO. The desired amount of membrane prep is diluted with ice-cold assay buffer (20 mM HEPES, pH 7.4, 100 mM NaCl, 10 mM MgCl$_2$, 0.1% Fatty acid-free BSA, 5 μM GDP) and vortexed well. 2 μl or less of compound is distributed into each well of a round-bottom 96-well polystyrene assay plate, followed by addition of 100 μl of diluted membranes (3-10 ng/well) and the mixture is kept on ice until the addition of hot GTPγS. [³⁵S]-GTPγS (Perkin Elmer NEG030H; 1 μCi/μl, 1250 Ci/mmol) is diluted 1:1000 (v/v) with cold assay buffer and 100 μl is added into each well. The reaction is carried out at room temperature for 90 minutes before the membranes are harvested onto PerkinElmer Unifilter GF/B-96 filter plate using a Packard Filtermate Harvester. After several washes with wash buffer (20 mM HEPES, pH 7.4, 100 mM NaCl, 10 mM MgCl$_2$), and a rinse with 95% ethanol, the filter is dried in a 37° C. oven for 30 minutes. MicroScint-20 is added and the plate sealed for scintillation counting on TopCount. EC$_{50}$ values are obtained by fitting the GTP [γ-³⁵S] binding data with the sigmoidal dose response curve-fitting tool of GraphPad Prism. Six or twelve different concentrations are used to generate a concentration response curve (using three data points per concentration).

For each assay, a Cheng-Prusoff correction (Cheng and Prusoff, 1973, Biochem. Pharmacol., 22:3099-3103) is used to convert the EC$_{50}$ to inhibition constant K$_i$. Thus, $$K_i = \frac{EC_{50}}{1 + [L]/K_d}$$

where [L] is the concentration of the radio-ligand used in the assay, and K$_d$ is the equilibrium binding dissociation constant for the radio-ligand.

Food Intake and Body Weight Gain

To evaluate the efficacy of compounds of the invention on inhibition of food intake and body weight gain, genetically obese (Lep$^{ob}$/Lep$^{ob}$) mice and diet-induced obese (DIO) mice are used in acute and sub-chronic models, respectively.

Male ob/ob mice (age 7-8 weeks old, Jackson Labs, Bar Harbor, Me.) are housed in groups of four and fed commercial standard pellet diet (Lab Diet 5001, PMI Nutrition International, LLC). Diet-induced obese mice are generated using 6-7 weeks old C57BL6 mice (Jackson Labs, Bar Harbor, Me.) placed on high fat diet (D12331, Research Diets) for 12-17 weeks. All mice are maintained on a 12-hour light/dark cycle (lights on at 06:00) in a humidity- and temperature-controlled environment with free access to food and water.

The week prior to the start of each study, mice are singly housed and a habituation to treatment is performed to establish baseline food consumption and body weight. Animals are randomized into treatment groups based on their initial body weight and food consumption.

To determine the acute effects of a single administration of a compound of the invention (test compound) on food consumption, ob/ob mice are treated with either vehicle, a known antagonist as a positive control, or with test compound(s). Similarly, to determine more chronic effects of test compound on food consumption and body weight gain, DIO mice are treated with either vehicle, a known antagonist as a positive control, or with test compound(s) for up to 7-35 days. Test compounds are dosed at ranges between 0.1 up to 100 mg/kg. Animals are treated one hour prior to the start of the dark cycle. Food intake and body weight are recorded manually using an electronic balance prior to treatment, 16 hours post-treatment, followed by daily measurements for up to 7-35 days after the start of study. Compound efficacy is determined by comparing food intake and body weight data between vehicle treated, standard positive control treated, and test compound treated mice.

Compounds of Formula I, in free form or in pharmaceutically acceptable salt form, exhibit valuable pharmacological properties, for example, as indicated by the in vitro tests described in this application. Compound of the invention show a K$_i$ of between 1×10$^{-5}$ and 1×10$^{-10}$M, preferably less than 500 nM, more preferably less than 100 nM. Additionally, compounds of the invention show a 10 fold, preferably 20, 50 and 100 fold, selectivity for CB1 over CB2. Additionally, compounds of the invention show a brain:plasma distribution of 1:10 preferably, 1:15, more preferably 1:20. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound selected from Formula Ia:

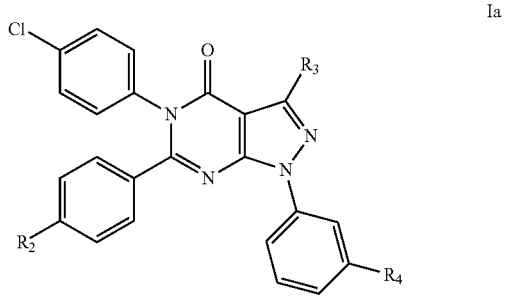

in which:

R$_2$ is selected from halo, pyrazinyl, pyridazinyl, pyrimidinyl, pyridinyl, pyridinyl-N-oxide and phenyl; wherein said pyrimidinyl, pyridinyl, pyridinyl-N-oxide, pyrazinyl and phenyl of R$_2$ is optionally substituted with a group selected from amino;

R$_3$ is selected from hydrogen, methyl-sulfonyl, methyl-sulfoxide and dimethyl-amino-carbonyl; and R$_4$ is selected from, amino-carbonyl, and methyl-sulfonyl.

2. The compound of claim 1 selected from:

6-[4-(6-amino-pyridazin-3-yl)-phenyl]-5-(4-chloro-phenyl)-1-(3-methanesulfonyl-phenyl)-1,5-dihydro-pyrazolo[3,4-d]pyrimidin-4-one;

3-[6-(4-bromo-phenyl)-5-(4-chloro-phenyl)-4-oxo-4,5-dihydro-pyrazolo[3,4-d]pyrimidin-1-yl]-benzamide;
3-[6-[4-(6-amino-pyridin-3-yl)-phenyl]-5-(4-chloro-phenyl)-4-oxo-4,5-dihydro-pyrazolo[3,4-d]pyrimidin-1-yl]-benzamide;
6-[4-(6-amino-pyridin-3-yl)-phenyl]-5-(4-chloro-phenyl)-1-(3-methanesulfonyl-phenyl)-1,5-dihydro-pyrazolo[3,4-d]pyrimidin-4-one;
6-[4-(5-amino-pyridin-2-yl)-phenyl]-5-(4-chloro-phenyl)-1-(3-methanesulfonyl-phenyl)-1,5-dihydro-pyrazolo[3,4-d]pyrimidin-4-one;
6-[4-(5-amino-pyrazin-2-yl)-phenyl]-5-(4-chloro-phenyl)-1-(3-methanesulfonyl-phenyl)-1,5-dihydro-pyrazolo[3,4-d]pyrimidin-4-one;
6-[4-(2-amino-pyrimidin-5-yl)-phenyl]-5-(4-chloro-phenyl)-1-(3-methanesulfonyl-phenyl)-1,5-dihydro-pyrazolo[3,4-d]pyrimidin-4-one;
3-[5-(4-chloro-phenyl)-4-oxo-6-(4-pyrazin-2-yl-phenyl)-4,5-dihydro-pyrazolo[3,4-d]pyrimidin-1-yl1-benzamide;
5-(4-chlorophenyl)-1-(3-(methylsulfonyl)phenyl)-6-(4-(pyrazin-2-yl)phenyl)-1H-pyrazolo[3,4-d]pyrimidin-4(5H)-one;
5-(4-chloro-phenyl)-1-(3-methanesulfonyl-phenyl)-6-(4-pyrimidin-5-yl-phenyl)-1,5-dihydro-pyrazolo[3,4-d]pyrimidin-4-one; and
5-(4-chloro-phenyl)-1-(3-methanesulfonyl-phenyl)-6-(4-pyrimidin-2-yl-phenyl)-1,5-dihydro-pyrazolo[3,4-d]pyrimidin-4-one.

3. A method of treating a disease mediated by the Cannabinoid-1 wherein said disease is an eating disorder associated with excessive food intake, comprising administration of to a patient in need of such treatment of a therapeutically effective amount of a compound of claim 1.

4. The method according to claim 3 wherein the eating disorder associated with excessive food intake is selected from obesity, bulimia nervosa, and compulsive eating disorders.

5. The method according to claim 4 wherein the eating disorder associated with excessive food intake is obesity.

6. A method of preventing obesity in a person at risk for obesity comprising administration to said person of about 0.001 mg to about 100 mg per kg of a compound selected from a compound of claim 1.

7. A composition comprising a pharmaceutically acceptable carrier and a compound selected from a compound of claim 1.

8. A compound selected from Formula Ia:

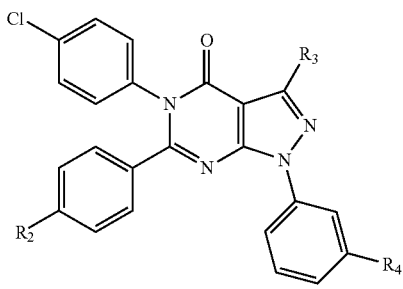

Ia in which:

$R_2$ is selected from halo, pyrazinyl, pyridazinyl, pyrimidinyl, pyridinyl, pyridinyl-N-oxide and phenyl; wherein said pyrimidinyl, pyridinyl, pyridinyl-N-oxide, pyrazinyl and phenyl of $R_2$ is optionally substituted with a radical selected from amino, halo, amino-sulfonyl and phenyl;

$R_3$ is selected from hydrogen, methyl-sulfonyl, methyl-sulfoxide and dimethyl-amino-carbonyl; and $R_4$ is selected from carbamimidoyl, tetrazolyl, amino-sulfonyl, and methyl-sulfonyl-amino.

9. The compound of claim 8 selected from:

3-(6-(4-bromophenyl)-5-(4-chlorophenyl)-4-oxo-4,5-dihydro-1H-pyrazolo[3,4-d]pyrimidin-1-yl)benzenesulfonamide;

3-[6-[4-(6-amino-pyridin-3-yl)-phenyl]-5-(4-chloro-phenyl)-4-oxo-4,5-dihydro-pyrazolo[3,4-d]pyrimidin-1-yl]-benzamidine;

3-[6-[4-(5-amino-pyridin-2-yl)-phenyl]-5-(4-chloro-phenyl)-4-oxo-4,5-dihydro-pyrazolo[3,4-d]pyrimidin-1-yl]-benzamidine;

6-[4-(6-amino-pyridin-3-yl)-phenyl]-5-(4-chloro-phenyl)-1-[3-(1H-tetrazol-5-yl)-phenyl]-1,5-dihydro-pyrazolo[3,4-d]pyrimidin-4-one;

6-[4-(5-amino-pyridin-2-yl)-phenyl]-5-(4-chloro-phenyl)-1-[3-(1H-tetrazol-5-yl)-phenyl]-1,5-dihydro-pyrazolo[3,4-d]pyrimidin-4-one;

N-(3-(6-(4-(6-aminopyridin-3-yl)phenyl)-5-(4-chlorophenyl)-4-oxo-4,5-dihydro-1H-pyrazolo[3,4-d]pyrimidin-1-yl)phenyl)methanesulfonamide;

N-(3-(6-(4-(5-aminopyridin-2-yl)phenyl)-5-(4-chlorophenyl)-4-oxo-4,5-dihydro-1H-pyrazolo[3,4-d]pyrimidin-1-yl)phenyl)methanesulfonamide;

N-(3-(5-(4-chlorophenyl)-4-oxo-6-(4-(pyrimidin-2-yl)phenyl)-4,5-dihydro-1H-pyrazolo[3,4-d]pyrimidin-1-yl)phenyl)methanesulfonamide;

N-{3-[5-(4-chloro-phenyl)-4-oxo-6-(4-pyrimidin-5-yl-phenyl)-4,5-dihydro-pyrazolo[3,4-d]pyrimidin-1-yl]-phenyl}-methane sulfonamide;

3-[5-(4-chloro-phenyl)-4-oxo-6-(4-pyrazin-2-yl-phenyl)-4,5-dihydro-pyrazolo[3,4-d]pyrimidin-1-yl]-benzamidine;

N-(3-(5-(4-chlorophenyl)-4-oxo-6-(4-(pyridazin-3-yl)phenyl)-4,5-dihydro-1H-pyrazolo[3,4-d]pyrimidin-1-yl)phenyl)methanesulfonamide;

N-(3-(5-(4-chlorophenyl)-4-oxo-6-(4-(pyrazin-2-yl)phenyl)-4,5-dihydro-1H-pyrazolo[3,4-d]pyrimidin-1-yl)phenyl)methanesulfonamide;

3-(5-(4-chlorophenyl)-4-oxo-6-(4-(pyrazin-2-yl)phenyl)-4,5-dihydro-1H-pyrazolo[3,4-d]pyrimidin-1-yl)benzenesulfonamide; and 3-[6-[4-(5-amino-pyridin-2-yl)-phenyl]-5-(4-chloro-phenyl)-4-oxo-4,5-dihydro-pyrazolo[3,4-d]pyrimidin-1-yl]-benzene sulfonamide.

* * * * *